US006784188B2

(12) United States Patent
Crooks et al.

(10) Patent No.: US 6,784,188 B2
(45) Date of Patent: *Aug. 31, 2004

(54) UREA SUBSTITUTED IMIDAZOQUINOLINES

(75) Inventors: Stephen L. Crooks, Mahtomedi, MN (US); George W. Griesgraber, Eagan, MN (US); Kyle J. Lindstrom, Houlton, WI (US); Bryon A. Merrill, River Falls, WI (US); Michael J. Rice, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/370,800

(22) Filed: Feb. 20, 2003

(65) Prior Publication Data

US 2004/0019048 A1 Jan. 29, 2004

Related U.S. Application Data

(63) Continuation of application No. 10/028,255, filed on Dec. 21, 2001, now Pat. No. 6,573,273, which is a continuation-in-part of application No. 09/589,236, filed on Jun. 7, 2000, now Pat. No. 6,541,485.
(60) Provisional application No. 60/138,365, filed on Jun. 10, 1999.

(51) Int. Cl.[7] .................. A61K 31/4745; C07D 471/02
(52) U.S. Cl. .......................................... 514/293; 546/82
(58) Field of Search ............................ 514/293; 546/82

(56) References Cited

U.S. PATENT DOCUMENTS

| | | | |
|---|---|---|---|
| 3,314,941 A | 4/1967 | Littell et al. | |
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster | |
| 5,268,376 A | 12/1993 | Gerster | |
| 5,346,905 A | 9/1994 | Gerster | |
| 5,352,784 A | 10/1994 | Nikolaides et al. | |
| 5,367,076 A | 11/1994 | Gerster | |
| 5,389,640 A | 2/1995 | Gerster et al. | |
| 5,395,937 A | 3/1995 | Nikolaides et al. | |
| 5,446,153 A | 8/1995 | Lindstrom et al. | |
| 5,482,936 A | 1/1996 | Lindstrom | |
| 5,693,811 A | 12/1997 | Lindstrom | |
| 5,741,908 A | 4/1998 | Gerster et al. | |
| 5,756,747 A | 5/1998 | Gerster et al. | |
| 5,939,090 A | 8/1999 | Beaurline et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,194,425 B1 | 2/2001 | Gerster et al. | |
| 6,245,776 B1 | 6/2001 | Skwierczynski et al. | |
| 6,331,539 B1 | 12/2001 | Crooks et al. | |
| 6,376,669 B1 | 4/2002 | Rice et al. | |
| 6,451,810 B1 | 9/2002 | Coleman et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,573,273 B1 * | 6/2003 | Crooks et al. .............. 514/293 |
| 2002/0055517 A1 | 5/2002 | Smith | |
| 2002/0058674 A1 | 5/2002 | Hedenstrom et al. | |

FOREIGN PATENT DOCUMENTS

| | | |
|---|---|---|
| EP | 0 394 026 | 10/1990 |
| EP | 1 104 764 | 6/2001 |
| HU | 210 051 B | 1/1995 |
| HU | 218 950 B | 1/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 98/48805 | 11/1998 |
| WO | WO 00/47719 | 8/2000 |
| WO | WO 00/76518 | 12/2000 |
| WO | WO 01/74343 | 10/2001 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46191 | 6/2002 |
| WO | WO 02/46192 | 6/2002 |
| WO | WO 02/46193 | 6/2002 |
| WO | WO 02/46749 | 6/2002 |
| WO | WO 02/102377 | 12/2002 |
| WO | WO 03/020889 | 3/2003 |

OTHER PUBLICATIONS

Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society*, 102, pp 511–513, Dec. 12, 1983.

Brennan, et al, "Automated Bioassay of Interferons in Micro–test Plates", *Biotechniques*, Jun./Jul., 78, 1983.

Testerman, et al., "Cytokine Induction by the Immunomodulators Imiquimod and S–27609", *Journal of Leukocyte Biology*, vol. 58, pp. 365–372, Sep. 1995.

(List continued on next page.)

*Primary Examiner*—Charanjit S. Aulakh
(74) *Attorney, Agent, or Firm*—Dean A. Ersfeld

(57) ABSTRACT

Imidazoquinoline and tetrahydroimidazoquinoline compounds that contain urea, thiourea, acylurea, or sulfonylurea functionality at the 1-position are useful as immune response modifiers. The compounds and compositions of the invention can induce the biosynthesis of various cytokines and are useful in the treatment of a variety of conditions including viral diseases and neoplastic diseases.

13 Claims, No Drawings

OTHER PUBLICATIONS

Bachman, et al, "Synthesis of Substituted Quinolylamines. Derivatives of 4-Amino-7-Chloroquinoline", *J. Org. Chem*, 15, pp 1278–1284 (1950).

Jain, et al, "Chemical and Pharmacological Investigations of Some ω-Substituted Alkylamino-3-aminopyridines", *J. Med. Chem.*, 11, pp 87–92 (1968).

Baranov, et al., *Chem. Abs.* 85, 94371, (1976).

Berényi, et al, "Ring Transformation of Condensed Dihydro-as-triazines", *J. Heterocyclic Chem.*, 18, pp 1537–1540 (1981).

Chollet, et al, "Development of a Topically Active Imiquimod Formulation", *Pharmaceutical Development and Technology*, 4(1), pp 35–43 (1999).

* cited by examiner

UREA SUBSTITUTED IMIDAZOQUINOLINES

CROSS REFERENCE TO RELATED APPLICATIONS

This application is a continuation of U.S. application Ser. No. 10/028,255, filed Dec. 21, 2001, now U.S. Pat. No. 6,573,271, which is a continuation-in-part of U.S. application Ser. No. 09/589,236, filed Jun. 7, 2000, now U.S. Pat. No. 6,541,485, which claims the benefit of U.S. Provisional Application Serial No. 60/138,365, filed Jun. 10, 1999.

FIELD OF THE INVENTION

This invention relates to imidazoquinoline compounds that have a substituent at the 1-position containing urea, thiourea, acylurea or sulfonylurea functionality, to pharmaceutical compositions containing such compounds, and to pharmaceutical compositions containing imidazoquinoline compounds that have carbamate functionality at the 1-position. A further aspect of this invention relates to the use of these compounds as immunomodulators, for inducing cytokine biosynthesis in animals, and in the treatment of diseases, including viral and neoplastic diseases.

BACKGROUND OF THE INVENTION

The first reliable report on the 1H-imidazo[4,5-c]quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1J-imidazo[4,5-c]quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J. Heterocyclic Chem.* 18, 1537–1540 (1981), have reported certain 2-oxoimidazo[4,5-c]quinolines.

Certain 1H-imidazo[4,5-c]quinolin4amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

There continues to be interest in the imidazoquinoline ring system. For example, EP 894 797 describes imidazoquinoline type compounds that bear an amide containing substituent at the 1-position. The specification of this patent teaches that the active compounds of this series require a terminal amine substituent that may be incorporated into a heterocyclic ring. As another example, WO 00/09506 describes imidazopyridine and imidazoquinoline compounds that may have an amide or urea containing substituent at the 1-position. The compounds described in this publication as having utility contain a 1-substituent wherein the amide or urea nitrogen is part of a heterocyclic ring. Despite these attempts to identify compounds that are useful as immune response modifiers, there is a continuing need for compounds that have the ability to modulate the immune response, by induction of cytokine biosynthesis or other mechanisms.

SUMMARY OF THE INVENTION

We have found compounds that are useful in inducing cytokine biosynthesis in animals. Accordingly, this invention provides imidazoquinoline and tetrahydroimidazoquinoline compounds of Formula (I):

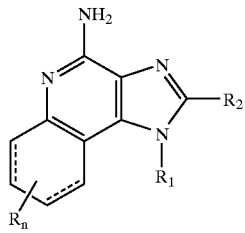

(I)

wherein $R_1$, $R_2$, and R are as defined infra. The invention also provides pharmaceutical compositions containing compounds of formula (Ia), which compounds have the same general structural formula as compounds (I) above.

The compounds of Formulae (I) and (Ia) are useful as immune response modifiers due to their ability to induce cytokine biosynthesis and otherwise modulate the immune response when administered to animals. This makes the compounds useful in the treatment of a variety of conditions, e.g. viral diseases and tumors that are responsive to such changes in the immune response.

The invention further provides pharmaceutical compositions that contain a therapeutically effective amount of a compound of Formula (I) or Ia), methods of inducing cytokine biosynthesis in an animal, treating a viral infection in an animal, and/or treating a neoplastic disease in an animal by administering a compound of Formula (I) or (Ia) to the animal.

In addition, methods of synthesizing the compounds of the invention and intermediates useful in the synthesis of these compounds are provided.

DETAILED DESCRIPTION OF THE INVENTION

As mentioned earlier, we have found that certain compounds induce cytokine biosynthesis in animals. Such compounds are represented by Formulae (I) and (Ia) below.

The invention provides compounds of Formula (I):

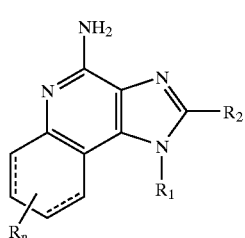

(I)

wherein
  $R_1$ is -alkyl-$NR_3$—CY—$NR_5$—X—$R_4$ or —alkenyl-$NR_3$—CY—$NR_5$—X—$R_4$ wherein
  Y is =O or =S;
  X is a bond, —CO— or —$SO_2$—;
  $R_4$ is aryl, heteroaryl, heterocyclyl, alkyl or alkenyl, each of which may be unsubstituted or substituted by one or more substituents selected from the group consisting of:
   -alkyl;
   -alkenyl;
   -aryl;

-heteroaryl
-heterocyclyl;
-substituted aryl;
-substituted heteroaryl;
-substituted heterocyclyl;
—O-alkyl;
—O-(alkyl)$_{0-1}$-aryl;
—O-(alkyl)$_{0-1}$-substituted aryl;
—O-(alkyl)$_{0-1}$-heteroaryl;
—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-substituted aryl;
—S(O)$_{0-2}$-(alkyl)$_{0-1}$-heteroaryl;
—S(O)$_{0-2}$-(alkyl)$_{0-1}$-substituted heteroaryl;
—S(O)$_{0-2}$-(alkyl)$_{0-1}$-heterocyclyl;
—S(O)$_{0-2}$-(alkyl)$_{0-1}$-substituted heterocyclyl;
-(alkyl)$_{0-1}$-NR$_3$R$_3$;
-(alkyl)$_{0-1}$-NR$_3$—CO—O-alkyl;
-(alkyl)$_{0-1}$-NR$_3$—CO-alkyl;
-(alkyl)$_{0-1}$-NR$_3$—CO-aryl;
-(alkyl)$_{0-1}$-NR$_3$—CO-substituted aryl;
-(alkyl)$_{0-1}$-NR$_3$—CO-heteroaryl;
-(alkyl)$_{0-1}$-NR$_3$—CO-substituted heteroaryl;
—N$_3$;
-halogen;
-haloalkyl;
-haloalkoxy;
—CO-haloalkoxy;
—NO$_2$;
—CN;
—OH; and
—SH; and in the case of alkyl, alkenyl, or heterocyclyl, oxo;
with the proviso that when X is a bond R$_4$ can additionally be hydrogen;
R$_2$ is selected from the group consisting of:
  -hydrogen;
  -alkyl;
  -alkenyl;
  -aryl;
  -substituted aryl;
  -heteroaryl;
  -substituted heteroaryl;
  -alkyl-O-alkyl;
  -alkyl-O-alkenyl; and
  -alkyl or alkenyl substituted by one or more substituents selected from the group consisting of:
    —OH;
    -halogen;
    —N(R$_3$)$_2$;
    —CO—N(R$_3$)$_2$;
    —CO—C$_{1-10}$ alkyl;
    —CO—O—C$_{1-10}$ alkyl;
    —N$_3$;
    -aryl;
    -substituted aryl;
    -heteroaryl;
    -substituted heteroaryl;
    -heterocyclyl;
    -substituted heterocyclyl;
    —CO-aryl;
    —CO-(substituted aryl);
    —CO-heteroaryl; and
    —CO-(substituted heteroaryl);
  each R$_3$ is independently selected from the group consisting of hydrogen and C$_{1-10}$ alkyl;
  R$_5$ is selected from the group consisting of hydrogen and C$_{1-10}$ alkyl, or R$_4$ and R$_5$ can combine to form a 3 to 7 membered heterocyclic or substituted heterocyclic ring;
  n is 0 to 4 and each R present is independently selected from the group consisting of C$_{1-10}$ alkyl, C$_{1-10}$ alkoxy, halogen and trifluoromethyl, or a pharmaceutically acceptable salt thereof.

The invention also provides pharmaceutical compositions comprising a therapeutically effective amount of a compound of Formula (Ia):

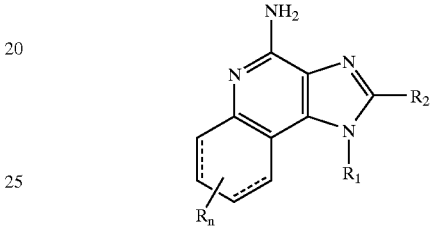

(Ia)

wherein
R$_1$ is -alkyl-NR$_3$—CO—O—R$_4$ or —alkenyl-NR$_3$—CO—O—R$_4$;
R$_4$ is aryl, heteroaryl, heterocyclyl, alkyl or alkenyl, each of which may be unsubstituted or substituted by one or more substituents selected from the group consisting of:
  -alkyl;
  -alkenyl;
  -aryl;
  -heteroaryl;
  -heterocyclyl;
  -substituted aryl;
  -substituted heteroaryl;
  -substituted heterocyclyl;
  —O-alkyl;
  —O-(alkyl)$_{0-1}$-aryl;
  —O-(alkyl)$_{01}$-substituted aryl;
  —O-(alkyl)$_{0-1}$-heteroaryl;
  —O-(alkyl)$_{0-1}$-substituted heteroaryl;
  —O-(alkyl)$_{0-1}$-heterocyclyl;
  —O-(alkyl)$_{0-1}$-substituted heterocyclyl;
  —COOH;
  —CO—O-alkyl;
  —CO-alkyl;
  —S(O)$_{0-2}$-alkyl;
  —S(O)$_{0-2}$-(alkyl)$_{0-1}$-aryl;
  —S(O)$_{0-2}$-(alkyl)$_{0-1}$-substituted aryl;
  —S(O)$_{0-2}$-(alkyl)$_{0-1}$-heteroaryl;
  —S(O)$_{0-2}$-(alkyl)$_{0-1}$-substituted heteroaryl;
  —S(O)$_{0-2}$-(alkyl)$_{0-1}$-heterocyclyl;
  —S(O)$_{0-2}$-(alkyl)$_{0-1}$-substituted heterocyclyl;
  -(alkyl)$_{0-1}$-NR$_3$R$_3$;
  -(alkyl)$_{0-1}$-NR$_3$—CO—O-alkyl;
  -(alkyl)$_{0-1}$-NR$_3$—CO-alkyl;
  -(alkyl)$_{0-1}$-NR$_3$—CO-aryl;
  -(alkyl)$_{0-1}$-NR$_3$—CO-substituted aryl;
  -(alkyl)$_{0-1}$-NR$_3$—CO-heteroaryl;
  -(alkyl)$_{0-1}$-NR$_3$—CO-substituted heteroaryl;

—$N_3$;
-halogen;
-haloalkyl;
-haloalkoxy;
—CO-haloalkoxy;
—$NO_2$;
—CN;
—OH; and
—SH; and in the case of alkyl, alkenyl, or heterocyclyl, oxo;

$R_2$ is selected from the group consisting of:
-hydrogen;
-alkyl;
-alkenyl;
-aryl;
-substituted aryl;
-heteroaryl;
-substituted heteroaryl;
-alkyl-O-alkyl;
-alkyl-O-alkenyl; and
-alkyl or alkenyl substituted by one or more substituents selected from the group consisting of:
  —OH;
  -halogen;
  —$N(R_3)_2$;
  —CO—$N(R_3)_2$;
  —CO—$C_{1-10}$ alkyl;
  —CO—O—$C_{1-10}$ alkyl;
  —$N_3$;
  -aryl;
  -substituted aryl;
  -heteroaryl;
  -substituted heteroaryl;
  -heterocyclyl;
  -substituted heterocyclyl;
  —CO-aryl;
  —CO-(substituted aryl);
  —CO-heteroaryl; and
  —CO-(substituted heteroaryl);
each $R_3$ is independently selected from the group consisting of hydrogen and $C_{1-10}$ alkyl;
n is 0 to 4 and each R present is independently selected from the group consisting of $C_{1-10}$ alkyl, $C_{1-10}$ alkoxy, halogen and trifluoromethyl, or a pharmaceutically acceptable salt thereof, in combination with a pharmaceutically acceptable carrier.

Preparation of the Compounds

Imidazoquinolines of the invention can be prepared according to Reaction Scheme I where R, $R_1$, $R_2$ and n are as defined above.

In step (1) of Reaction Scheme I a 4chloro-3-nitroquinoline of Formula II is reacted with an amine of Formula $R_1NH_2$ where $R_1$ is as defined above to provide a 3-nitroquinolin-4-amine of Formula III. The reaction can be carried out by adding amine to a solution of a compound of Formula II in a suitable solvent such as chloroform or dichloromethane and optionally heating. Many quinolines of Formula II are known compounds (see for example, U.S. Pat. No. 4,689,338 and references cited therein).

In step (2) of Reaction Scheme I a 3-nitroquinolin-4-amine of Formula III is reduced to provide a quinoline-3,4-diamine of Formula IV. Preferably, the reduction is carried out using a conventional heterogeneous hydrogenation catalyst such as platinum on carbon or palladium on carbon. The reaction can conveniently be carried out on a Parr apparatus in a suitable solvent such as isopropyl alcohol or toluene.

In step (3) of Reaction Scheme I a quinoline-3,4-diamine of Formula IV is reacted with a carboxylic acid or an equivalent thereof to provide a 1H-imidazo[4,5-c]quinoline of Formula V. Suitable equivalents to carboxylic acid include acid halides, orthoesters, and 1,1-dialkoxyalkyl alkanoates. The carboxylic acid or equivalent is selected such that it will provide the desired R, substituent in a compound of Formula V. For example, triethyl orthoformate will provide a compound where $R_2$ is hydrogen and triethyl orthoacetate will provide a compound where $R_2$ is methyl. The reaction can be run in the absence of solvent or in an inert solvent such as toluene. The reaction is run with sufficient heating to drive off any alcohol or water formed as a by product of the reaction.

In step (4) of Reaction Scheme I a 1H-imidazo[4,5-c]quinoline of Formula V is oxidized to provide a 1H-imidazo[4,5-c]quinoline-5N-oxide of Formula VI using a conventional oxidizing agent that is capable of forming N-oxides. Preferred reaction conditions involve reacting a solution of a compound of Formula V in chloroform with 3-chloroperoxybenzoic acid at ambient conditions.

In step (5) of Reaction Scheme I a 1H-imidazo[4,5-c]quinoline-5N-oxide of Formula VI is aminated to provide a 1H-imidazo[4,5-c]quinolin-4-amine of Formula VII, which is a subgenus of Formula I. Step (5) involves (i) reacting a compound of Formula VI with an acylating agent and then (ii) reacting the product with an aminating agent. Part (i) of step (5) involves reacting an N-oxide of Formula VI with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (5) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide of Formula VI in an inert solvent such as dichloromethane, adding the aminating agent to the solution, and then slowly adding the acylating agent. The product or a pharmaceutically acceptable salt thereof can be isolated using conventional methods.

Alternatively, step (5) may be carried out by (i) reacting an N-oxide of Formula VI with an isocyanate and then (ii) hydrolyzing the resulting product. Part (i) involves reacting the N-oxide with an isocyanate wherein the isocyanato group is bonded to a carbonyl group. Preferred isocyanates include trichloroaectyl isocyanante and aroyl isocyanates such as benzoyl isocyanate. The reaction of the isocyanate with the N-oxide is carried out under substantially anhydrous conditions by adding the isocyanate to a solution of the N-oxide in an inert solvent such as chloroform or dichloromethane. Part (ii) involves hydrolysis of the product from part (i). The hydrolysis can be carried out by conventional methods such as healing in the presence of water or a lower alkanol optionally in the presence of a catalyst such as an alkali metal hydroxide or lower alkoxide.

Reaction Scheme I

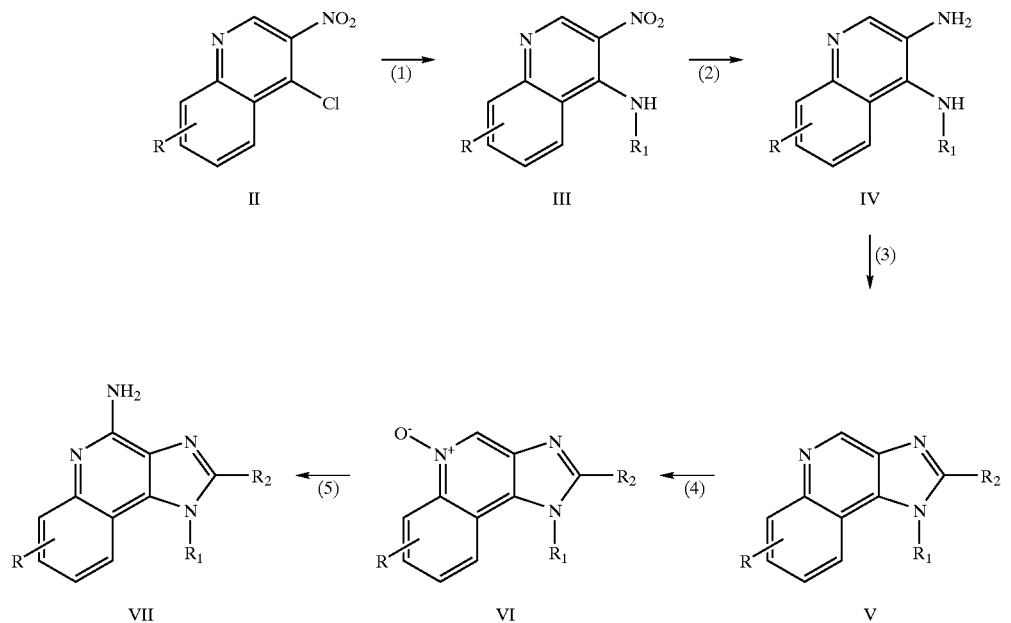

Compounds of the invention where the $R_1$ substituent contains a urea or a thiourea can also be prepared according to Reaction Scheme II where R, $R_2$, $R_4$ and n are as defined above and Y is O or S and m is an integer from 1 to 20.

In Reaction Scheme II an aminoalkyl substituted 1H-imidazo[4,5-c]quinolin-4-amine of Formula VIII is reacted with an isocyanate or thioisocyanate of Formula IX to provide a compound of Formula X which is a subgenus of Formula I. The reaction can be carried out by adding a solution of the (thio)isocyanate in a suitable solvent such as dichloromethane to a solution of a compound of Formula VIII, optionally at a reduced temperature. Many 1H-imidazo [4,5-c]quinolin-4-amines of Formula VIII are known compounds (see for example U.S. Pat. No. 6,069,149 (Nanba)); others can be readily prepared using known synthetic methods. Many isocyanates and thioisocyanates of Formula IX are commercially available; others can be readily prepared using known synthetic methods. The product or a pharmaceutically acceptable salt thereof can be isolated using conventional methods.

Reaction Scheme II

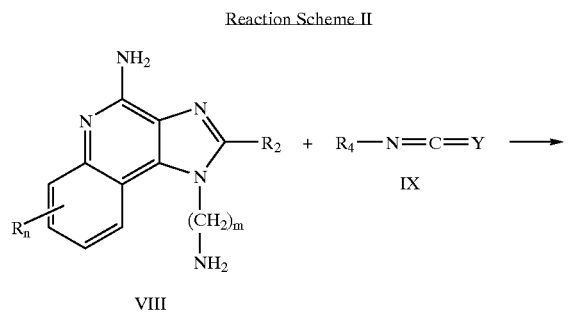

-continued

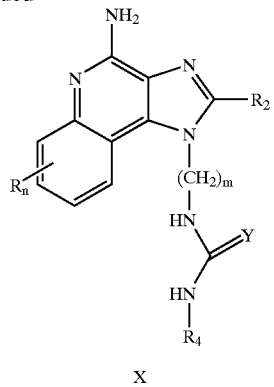

X

Compounds of the invention where the $R_1$ substituent contains a urea can also be prepared according to Reaction Scheme III where R, $R_2$, $R_4$, $R_5$ and n are as defined above and m is an integer from 1 to 20.

In Reaction Scheme III an aminoalkyl substituted 1H-imidazo[4,5-c]quinolin-4-amine of Formula VIII is reacted with a carbamoyl chloride of Formula XI to provide a compound of Formula XII which is a subgenus of Formula I. The reaction can be carried out by adding a solution of the carbamoyl chloride in a suitable solvent such as pyridine to a solution of a compound of Formula VIII at ambient temperature. Some carbamoyl chlorides of Formula XI are commercially available; others can be readily prepared using known synthetic methods. The product or a pharmaceutically acceptable salt thereof can be isolated using conventional methods.

Reaction Scheme III

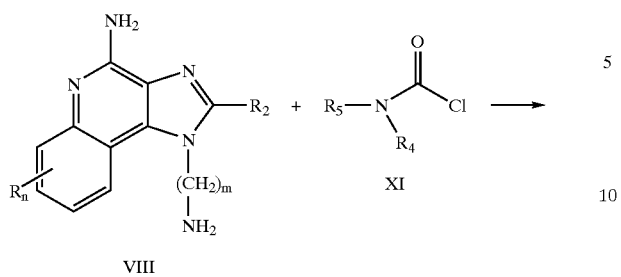

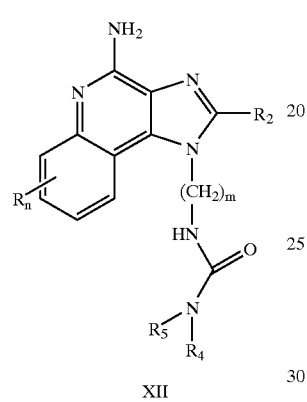

Compounds of the invention where the $R_1$ substituent contains a carbamate can also be prepared according to Reaction Scheme IV where R, $R_2$, R4, n and m are as defined above.

In Reaction Scheme IV an aminoalkyl substituted 1H-imidazo[4,5-c]quinolin-4-amine of Formula VIII is reacted with an chloroformate of Formula XIII to provide a compound of Formula XIV which is a subgenus of Formula Ia. The reaction can be carried out by adding a solution of the chloroformate in a suitable solvent such as dichloromethane or pyridine to a solution of a compound of Formula VIII optionally at a reduced temperature. Many chloroformates of Formula XIII are commercially available; others can be readily prepared using known synthetic methods. The product or a pharmaceutically acceptable salt thereof can be isolated using conventional methods.

Reaction Scheme IV

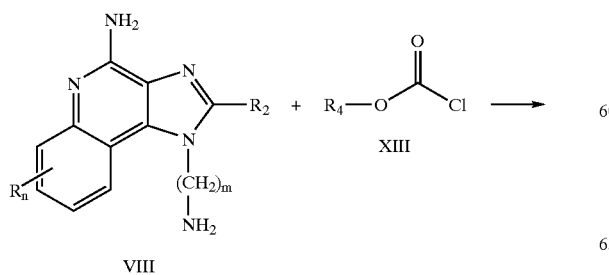

Compounds of the invention where the $R_1$ substituent contains an acyl urea can also be prepared according to Reaction Scheme V where R, $R_2$, $R_4$, n and m are as defined above In Reaction Scheme V an aminoalkyl substituted 1H-imidazo[4,5-c]quinolin4-amine of Formula VIII is reacted with an acyl isocyanate of Formula XV to provide a compound of Formula XVI which is a subgenus of Formula I. The reaction can be carried out by adding a solution of the acyl isocyanate in a suitable solvent such as dichloromethane to a solution of a compound of Formula VIII at a reduced temperature. Some acyl isocyanates of Formula XV are commercially available; others can be readily prepared using known synthetic methods. The product or a pharmaceutically acceptable salt thereof can be isolated using conventional methods.

Reaction Scheme V

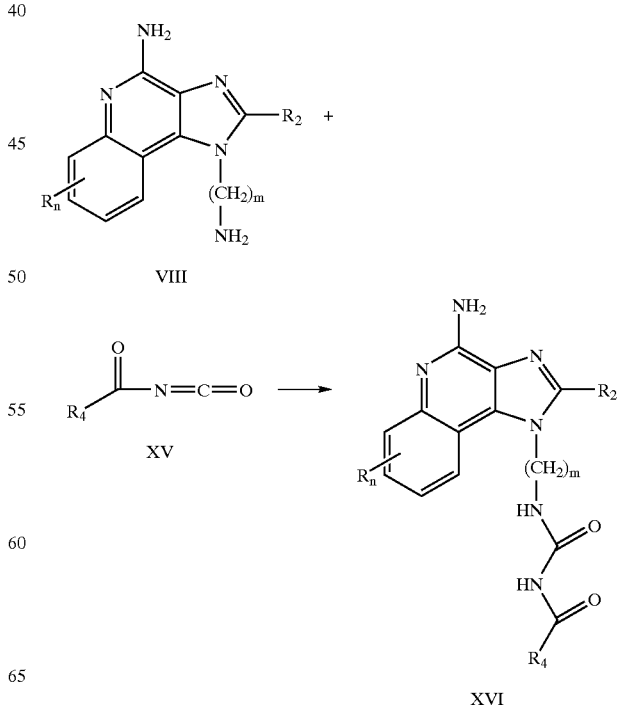

Compounds of the invention where the $R_1$ substituent contains a sulfonyl urea can also be prepared according to Reaction Scheme VI where R, $R_2$, $R_4$, n and m are as defined above In Reaction Scheme VI an aminoalkyl substituted 1H-imidazo[4,5-c]quinolin4-amine of Formula VIII is reacted with a sulfonyl isocyanate of Formula XVII to provide a compound of Formula XVIII which is a subgenus of Formula I. The reaction can be carried out by adding a solution of the sulfonyl isocyanate in a suitable solvent such as dichloromethane to a solution of a compound of Formula VIII, optionally at a reduced temperature. Some sulfonyl isocyanates of Formula XVII are commercially available; others can be readily prepared using known synthetic methods. The product or a pharmaceutically acceptable salt thereof can be isolated using conventional methods.

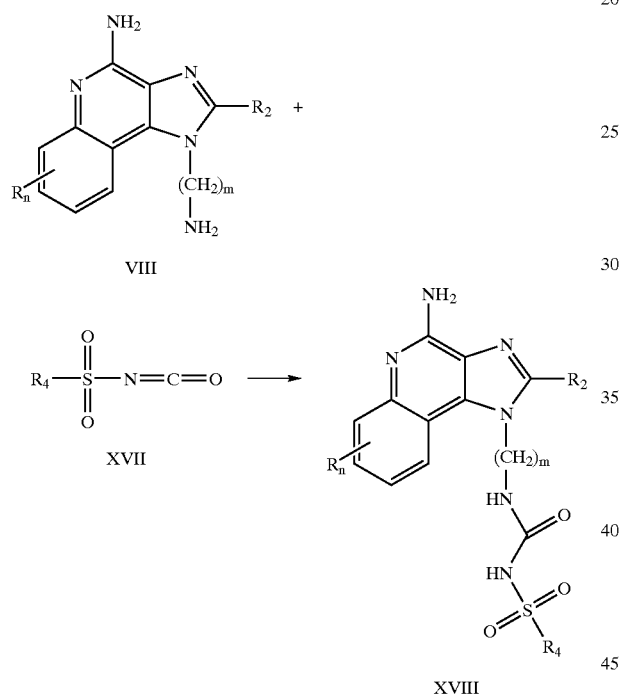

Tetrahydroimidazoquinolines of the invention can be prepared according to Reaction Scheme VII where $R_2$, $R_3$, $R_4$, $R_5$, X, Y and m are as defined above.

In step (I) of Reaction Scheme VII an aminoalkyl substituted 1H-imidizo[4,5-c]quinolin-4-amine of Formula XIX is reduced to provide an aminoalkyl substituted 6,7,8,9-tetrahydro-1H-imidazo[4,5-c]quinolin-4-amine of Formula XX. Preferably the reduction is carried out by suspending or dissolving the compound of Formula XIX in trifluoroacetic acid, adding a catalytic amount of platinum (IV) oxide, and then subjecting the mixture to hydrogen pressure. The reaction can conveniently be carried out on a Parr apparatus. The product or a salt thereof can be isolated using conventional methods.

Step (2) of Reaction Scheme VII can be carried out using the methods described in Reaction Schemes II, III, IV, V and VI to provide a compound of Formula XXI which is a subgenus of Formula I.

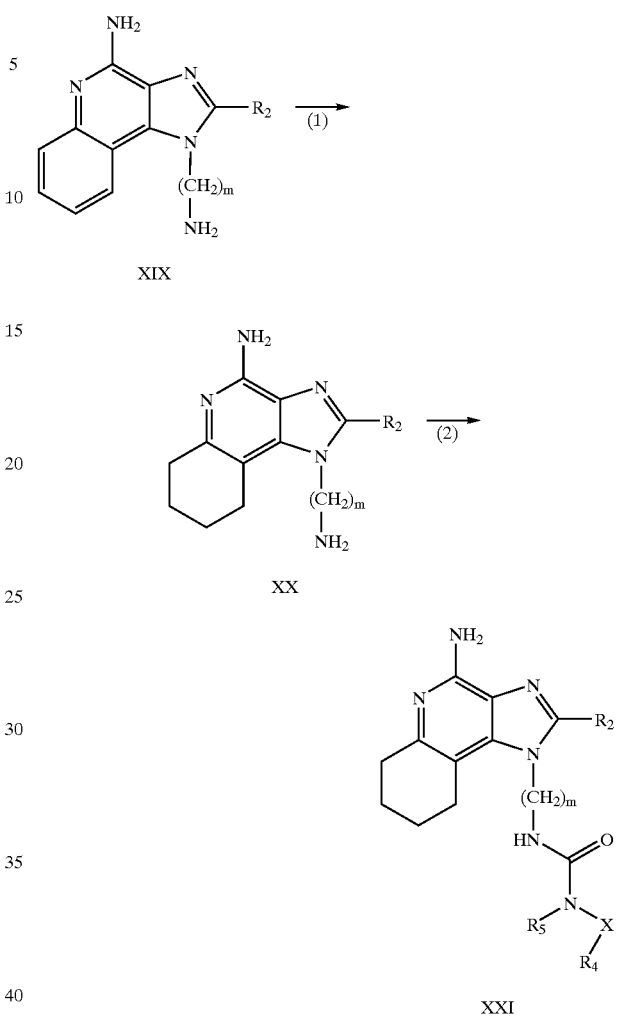

Tetrahydroimidazoquinolines of the invention can also be prepared according to Reaction Scheme VIII where R, $R_2$, $R_3$, $R_4$, $R_5$, X, Y, n and m are as defined above.

In step (I) of Reaction Scheme VIII a 6,7,8,9-tetrahydro-1H-imidazo[4,5-c]quinolinyl tert-butylcarbamate of Formula XXII is hydrolyzed to provide an aminoalkyl substituted 6,7,8,9-tetrahydro-1H-imidazo[4,5-c]quinolin-4-amine of Formula XXIII. The reaction can be carried out by dissolving the compound of Formula XXII in a mixture of trifluoroacetic acid and acetonitrile and stirring at ambient temperature. Alternatively, the compound of Formula XXII can be combined with dilute hydrochloric acid and heated on a steam bath. Tetrahydro-1H-imidazo[4,5-c]quinolinyl tert-butylcarbamates of Formula XXII can be prepared using the synthetic route disclosed in U.S. Pat. No. 5,352,784 (Nikolaides). The product or a salt thereof can be isolated using conventional methods.

Step (2) of Reaction Scheme VIII can be carried out using the methods described in Reaction Schemes II, III, IV, V and VI to provide a compound of Formula XXIV which is a subgenus of Formula I.

Reaction Scheme VIII

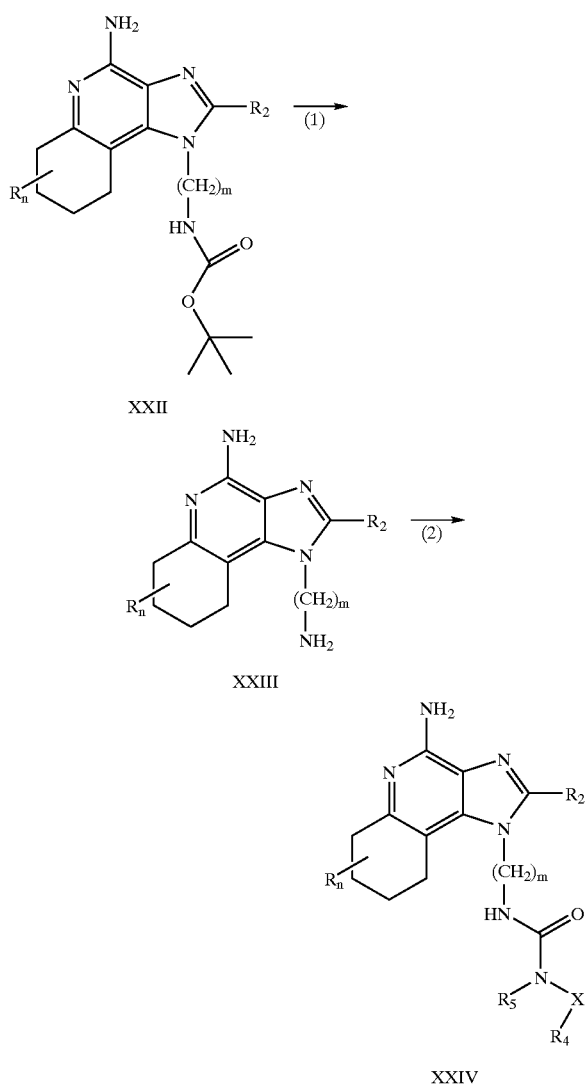

Some compounds of Formula I can be readily prepared from other compounds of Formula I. For example, compounds wherein the $R_4$ substituent contains a chloroalkyl group can be reacted with an amine to provide an $R_4$ substituent substituted by a secondary or teriary amino group; compounds wherein the $R_4$ substituent contains a nitro group can be reduced to provide a compound wherein the $R_4$ substituent contains a primary amine.

As used herein, the terms "alkyl", "alkenyl", "alkynyl" and the prefix "-alk" are inclusive of both straight chain and branched chain groups and of cyclic groups, i.e. cycloalkyl and cycloalkenyl. Unless otherwise specified, these groups contain from 1 to 20 carbon atoms, with alkenyl and alkynyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl and adamantyl.

The term "haloalkyl" is inclusive of groups that are substituted by one or more halogen atoms, including groups wherein all of the available hydrogen atoms are replaced by halogen atoms. This is also true of groups that include the prefix "haloalk-". Examples of suitable haloalkyl groups are chloromethyl, trifluoromethyl, and the like. The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g. O, S, N). Suitable heteroaryl groups include furyl, thienyl, pyridyl, quinolinyl, tetrazolyl, imidazo, pyrazolo, oxazolo, thiazolo and the like.

"Heterocyclyl" includes non-aromatic rings or ring systems that contain at least one ring hetero atom (e.g., O, S, N). Exemplary heterocyclic groups include pyrrolidinyl, tetrahydrofuranyl, morpholinyl, thiomorpholinyl, piperdinyl, piperazinyl, thiazolidinyl, imidazolidinyl and the like.

Unless otherwise specified, the terms "substituted aryl", "substituted heteroaryl" and "substituted heterocyclyl" indicate that the rings or ring systems in question are further substituted by one or more substituents independently selected from the group consisting of alkyl, alkoxy, alkylthio, hydroxy, halogen, haloalkyl, haloalkylcarbonyl, haloalkoxy (e.g., trifluoromethoxy), nitro, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrite, alkoxycarbonyl, alkanoyloxy, alkanoylthio, and in the case of heterocyclyl, oxo.

In structural formulas representing compounds of the invention certain bonds are represented by dashed lines. These lines mean that the bonds represented by the dashed line can be present or absent. Accordingly, compounds of Formula I can be either imidazoquinoline compounds or tetrahydroimidazoquinoline compounds.

The invention is inclusive of the compounds described herein in any of their pharmaceutically acceptable forms, including isomers such as diastereomers and enantiomers, salts, solvates, polymorphs, and the like.

Pharmaceutical Compositions and Biological Activity

Pharmaceutical compositions of the invention contain a therapeutically effective amount of a compound of the invention in combination with a pharmaceutically acceptable carrier.

The term "a therapeutically effective amount" means an amount of the compound sufficient to induce a therapeutic effect, such as cytokine induction, antitumor activity and/or antiviral activity. Although the exact amount of active compound used in a pharmaceutical composition of the invention will vary according to factors known to those of skill in the art, such as the physical and chemical nature of the compound as well as the nature of the carrier and the intended dosing regimen, it is anticipated that the compositions of the invention will contain sufficient active ingredient to provide a dose of about 100 ng/kg to about 50mg/kg, preferably about 10 µg/kg to about 5mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in a treatment regimen, or the compounds of the invention may be administered in combination with one another or with other active agents, including additional immune response modifiers, antivirals, antibiotics, and so on.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines that maybe induced by the administration of compounds according to the invention generally include interferon (IFN) and/or tumor necrosis factor-α (TNF-α) as well as certain interleukins (IL). Cytokines whose biosynthesis may be induced by compounds of the invention include IFN-α, TNF-α, IL-1, 6, 10 and 12, and a variety of other cytokines. Among other effects, cytokines inhibit virus production and tumor cell growth, making the compounds useful in the treatment of tumors and viral diseases.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th 1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th 1 response and/or downregulation of the Th2 response is desired. In view of the ability of compounds of Formula Ia to inhibit the Th2 immune response, the compounds are expected to be useful in the treatment of conditions that are associate with overstimulation of a Th2 response such as atopic diseases, e.g., atopic dermatitis; asthma; allergy; allergic rhinitis; systemic lupus erythematosis; as a vaccine adjuvant for cell mediated immunity; and possibly as a treatment for recurrent fungal diseases, periodontitis and chlamydia.

The immune response modifying effects of the compounds make them useful in the treatment of a wide variety of conditions. Because of their ability to induce the production of cytokines such as IFN-α and/or TNF-α, and IL-12, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Type I and Type II; molluscum contagiosum; HIV; CMV; VZV; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis camii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include eczema; eosinophilia; essential thrombocythacmia; leprosy; multiple sclerosis; Ommen's syndrome; discoid lupus; Bowen's disease; Bowenoid papulosis; and to enhance or stimulate the healing of wounds, including chronic wounds.

Accordingly, the invention provides a method of inducing cytokine biosynthesis in an animal comprising administering an effective amount of a compound of Formula Ia to the animal. An amount of a compound effective to induce cytokine biosynthesis is an amount sufficient to cause one or more cell types, such as monocytes, macrophages, dendritic cells and B-cells to produce an amount of one or more cytokines such as, for example, IFN-β, TNF-β, IL-1,6,10 and 12 that is increased over the background level of such cytokines. The precise amount will vary according to factors known in the art but is expected to be a dose of about 100 ng/kg to about 50mg/kg, preferably about 10 μg/kg to about 5mg/kg. The invention also provides a method of treating a viral infection in an animal comprising administering an effective amount of a compound of Formula Ia to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of 100 ng/kg to about 50mg/kg, preferably about 10 μg/kg to about 5mg/kg. An amount effective to treat a neoplastic condition is an amount that will cause a reduction in tuor size or in the number of tumor foci. Again, the precise amount will vary according to factors known in the art but is expected to be a dose of about 100 mg/kg to about 50 mg/kg. Preferably about 10 mg/kg to about 5 mg/kg.

The invention is further described by the following examples, which are provided for illustration only and are not intended to be limiting in any way.

EXAMPLE 1

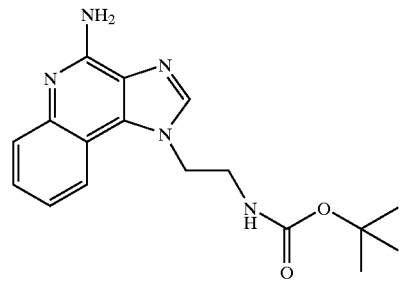

Tert-Butyl N-[2-(4-Amino-1H-imidazo[4,5-c]quinolin-1-yl)ethyl]carbamate

Part A

Triethylamine (66.8 g, 0.33 mol) was added to a solution of tert-butyl N-(2-aminoethyl)carbamate (55.0 g, 0.34 mol) in anhydrous dichloromethane (500 mL). 4-Chloro-3-nitroquinoline (68.2 g, 0.33 mol) was slowly added and the reaction exothermed. The reaction mixture was allowed to stir at ambient temperature overnight. The resulting precipitate was isolated by filtration to provide product as a yellow solid. The filtrate was washed with water, dried over magnesium sulfate and then concentrated under vacuum. The resulting residue was slurried with hexane and filtered to provide additional product as a yellow solid. The two crops were combined to provide 101 g of tert-butyl N-[2-(3-nitroquinolin-4-yl)aminoethyl]carbamate as a yellow solid, m.p. 157–158.

Part B

Platinum on carbon (1 g of 10%) and sodium sulfate (2 g) were added to a slurry of tert-butyl N-[2-(3-nitroquinolin-4-yl)aminoethyl]carbamate (100 g, 0.30 mol) in toluene (500 mL). The mixture was placed under a hydrogen atmosphere at 50 psi (3.4×10⁴ pascals) on a Parr apparatus at ambient temperature overnight. The reaction mixture was filtered. The filtrate was concentrated to provide 73 g of tert-butyl N-[2-(3-aminoquinolin-4-yl)aminoethyl] carbamate as a dark gold oil.

Part C

Triethyl orthoformate (11.3 g, 73.4 mmol) was added to a solution of tert-butyl N-[2-(3-aminoquinolin-4-yl) aminoethyl]carbamate (21 g, 69.4 mmol) in anhydrous toluene (250 mL). The reaction mixture was heated at reflux for 5 hours and then allowed to slowly cool to ambient temperature. The resulting precipitate was isolated by filtration and dried to provide 17.6 g of tert-butyl N-[2-(1H-imidazo [4,5-c]quinolin-1-yl)ethyl]carbamate as a light tan solid, m.p. 154–155° C.

Part D

3-Chloroperoxybenzoic acid (17.4 g, 60.6 mmol) was added in small portions to a solution of tert-butyl N-[2-(1H-imidazo[4,5-c]quinolin-1-yl)ethyl]carbamate (17.2 g, 55.1 mmol) in chloroform (250 mL). The reaction was maintained at ambient temperature overnight and then quenched with 5% sodium carbonate solution. The layers were separated. The organic layer was dried over magnesium sulfate and then concentrated under vacuum to provide 15.0 g of 1-[2-(tert-butylcarbamyl)ethyl]-1H-imidazo[4,5-c] quinoline-SN-oxide as an off white solid, m.p. 213–215° C.

Part E

Trichloroacetyl isocyanate (9.5 g, 50.2 mmol) was slowly added to a stirred solution of 1-[2-(tert-butylcarbamyl) ethyl]-1H-imidazo[4,5]quinoline-5N-oxide (15.0 g, 45.7 mmol) in chloroform (200 mL). After 2 hours the reaction was quenched with concentrated ammonium hydroxide (100 mL). Water (100 mL) was added and the layers were separated. The aqueous layer was extracted with chloroform. The organic layers were combined, dried over magnesium sulfate and then concentrated under vacuum to provide a white solid. This material was slurried in warm methyl acetate and then filtered to provide 15 g of tert-butyl N-[2-(4-amino-1H-imidazo[4,5-c]quinolin-1-yl)ethyl] carbamate as a white solid, m.p. 215° C. ¹H NMR (500 MHz, DMSO-d₆) δ 8.13 (t, J=8.0 Hz, 1H), 8.03 (s, 1H), 7.61 (d, J=8.0 Hz, 1H), 7.44 (t, J=8.0 Hz, 1H), 7.23 (t, J=8.0 Hz, 1H), 7.06 (t, J=6.0 Hz, 1H), 6.56 (broad s, 2H), 4.63 (t, J=7.0 Hz, 2H), 3.43 (q, J=6.0 Hz, 2H), 1.32 (s, 9H); MS (EI) m/e 327.1696 (327.1695 calcd for $C_{17}H_{21}N_5O_2$)

EXAMPLE 2 culated for $C_{18}H_{24}N_4O_4$: %C, 59.99; %H, 6.71; %N, 15.55; Found: %C, 59.68; %H, 6.59; %N, 15.74.

Part B

Using the general method of Example 1 Part B, tert-butyl N-(4-[(3-nitroquinolin-4-yl)amino]butyl)carbamate (162.6 g, 0.451 mol) was hydrogenated to provide 149 g of tert-butyl N-(4-[(3-aminoquinolin-4-yl)amino]butyl)carbamate as a dark gold gum.

Part C

Using the general method of Example 1 Part C, tert-butyl N-(4-[(3-aminoquinolin-4-yl)amino]butyl)carbamate (149 g, 0.451 mol) was reacted with triethyl orthoformate to provide crude product This material was recrystallized from isopropyl alcohol to provide 84 g of tert-butyl N-[4-(1H-imidazo[4,5-c]quinolin-1-yl)butyl]carbamate as a crystalline solid.

Part D

Using the general method of Example 1 Part D, tert-butyl N-[4(1H-imidazo[4,5-c]quinolin-1-yl)butyl]carbamate (84.0 g, 0.247 mol) was oxidized to provide 87.9 g of 1-[[4-(tert-butylcarbamyl)butyl]-1H-imidazo[4,5-c] quinoline-5N-oxide as a green/yellow foam.

Part E

Concentrated ammonium hydroxide (250 mL) was added to a vigorously stirred solution of 1-[4-(tert-butylcarbamyl) butyl]-1H-imidazo[4,5-c]quinoline-5N-oxide (87.9 g, 0.247 mol) in dichloromethane (750 mL). Tosyl chloride (47.0 g, 0.247 mol) was added in small portions over a period of 30 minutes. The reaction mixture was allowed to stir at ambient temperature overnight then it was filtered to remove a tan precipitate. The filtrate layers were separated. The aqueous layer was extracted with dichloromethane (4×50 mL). The dichloromethane fractions were combined, dried over sodium sulfate and then concentrated under vacuum to provide a pale tan solid. This material was recrystallized from isopropyl alcohol to provide 75.7 g of tert-butyl N-(2-(4amino-1H-imidazo[4,5-c]quinolin-1-yl)butyl] carbamate as a pale yellow solid, m.p. 171–173° C. ¹H NMR (500 MHz, CDCl₃) δ 8.19 (s, 1H), 8.03 (d, J=8.0 Hz, 1H), 7.62 (d, J=8.0 Hz, 1H), 7.44 (t, J=8.0 Hz, 1H), 7.26 (d, J=8.0 Hz, 1H), 6.83 (t, J=6.0 Hz, 1H), 6.60 (broad s, 2H), 4.59 (t, J=7.0 Hz, 2H), 2.95 (q, J=6.0 Hz, 2H), 1.83 (quintet, J=7.0 Hz, 2H), 1.42 (quintet, J=7.0 Hz, 2H), 1.33 (s, 9H). MS (EI) m/e 355.2001 (355.2008 calcd for $C_{19}H_{25}N_5O_2$).

EXAMPLE 3

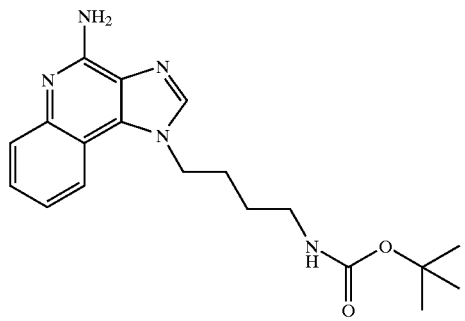

Tert-Butyl N-[2-(4-Amino-1H-imidazo[4,5-c]quinolin-1-yl)butyl]carbamate

Part A

Using the general method of Example 1 Part A, tert-butyl N-(4-aminobutyl)carbamate (254 g, 1.35 mol) was reacted with 4chloro-3-nitroquinoline hydrochloride (331 g, 1.35 mmol) to provide 486 g of tert-butyl N-(4-[(3-nitroquinolin-4yl)amino]butyl)carbamate as yellow solid. Analysis: Cal-

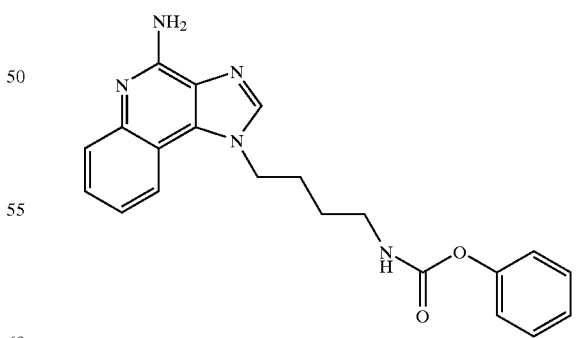

Phenyl N-[4-(4-amino-1H-imidazo[4,5-c]quinolin-1-yl)butyl]carbamate

A solution of 1-(4-aminobutyl)-1H-imidazo[4,5-c] quinolin-4-amine (9.3 mg, 36 μmol) in 10 mL of dichloromethane was cooled to −5° C. and a solution of phenyl chloroformate (7 mg, 45 μmol) in 1.5 mL of dichloromethane was added, with argon bubbling to facilitate mixing. The mixture was then allowed to warm to room temp. while being vortexed for 10 min. Aminomethylpolystyrene (ca. 80 mg, 1 meq/g, 100–200 mesh, Bachem) was added to quench excess chloroformate, and the mixture was refluxed and vortexed for several hours. The mixture was chromatographed through a short plug of silica gel with 10:1 dichloromethane-methanol as eluant to isolate the product as a solid.

$^1$H NMR (500 MHz, DMSO-$d_6$) δ 8.28 (s, 1H), 8.06 (d, J=7.6 Hz, 1H), 7.76 (t, J=5.6 Hz, 1H), 7.63 (d, J=8.2 Hz, 1H), 7.45 (t, J=7 Hz, 1H), 7.34 (t, J=8.2 Hz, 2H), 7.27 (t, J=7.5 Hz, 1H), 7.18 (t, J=7.3 Hz, 1H), 7.00 (d, J=8.6 Hz, 2H), 6.65 (bs, 2H), 4.64 (t, J=7 Hz, 2H), 3.10 (q, J=6 Hz, 2H), 1.92 (quintet, J=7 Hz, 2H), 1.52 (quintet, J=7 Hz, 2 H), 2H). Ms (APCI) m/e 376.15 (M+H).

EXAMPLE 4

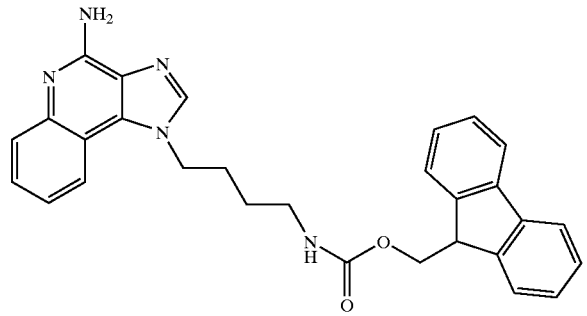

9H-9-Fluorenylmethyl N-[4-(4-amino-1H-imidazo[4,5-c]quinolin-1-yl)butyl]carbamate To a solution of 1-(4aminobutyl)-1H-imidazo[4,5-c]quinolin-4-amine (9.3 mg, 36 μmol) in 10 mL of dichloromethane at ambient temperature was added 9-fluorenylmethyl chloroformate (8 mg, 30 μmol) as a solid. The mixture was vortexed at room temperature for about 1 min., becoming slightly cloudy. Aminomethylpolystyrene (ca. 90 mg, 0.64 meq/g, 100–200 mesh, Bachem) was added to quench excess chloroformate, and after a few minutes the mixture was filtered through a short plug of silica gel, eluting with 10:1 dichloromethane-methanol to isolate the product as a solid. $^1$H NMR (500 MHz, DMSO-$d_6$) δ 8.27 (s, 1H), 8.08 (d, J=8.1 Hz, 1H), 7.87 (d, J=7.6 Hz, 2H), 7.65 (m, 3H), 7.50 (t, J=7.6 Hz, 1H), 7.40 (t, J=7.3 Hz, 2H), 7.3 (m, 4H), 7.15 (bs, 2H), 4.62 (t, J=7H, 2H), 4.27 (d, J=7 Hz, 2H), 4.17 (t, J=7 Hz, 1H), 3.03 (q, J=7 Hz, 2H), 1.84 (quintet, J=7 Hz, 2H), 1.45 (quintet, J=7 Hz, 2H). MS (APCI) m/e 478.28 (M+H).

EXAMPLE 5

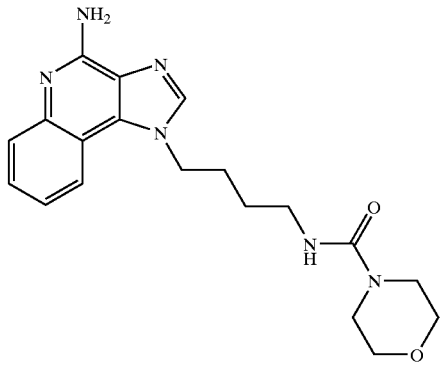

$N^1$-[4-(4-Amino-1H-imidazo[4,5-c]quinolin-1-yl)butyl]-4-morpholinecarboxamide

4-Morpholinecarbonyl chloride (0.15 ml, 1.3 mmol) was added to a stirring solution of 1-(4-aminobutyl)-1H-imidazo[4,5-c]quinolin-4-amine (0.3 g, 1.2 mmol) and pyridine (70 ml). The reaction was maintained at room temperature overnight. The solvent was removed in vacuo and the residue was purified by flash column chromatography (silica gel, 9:1 dichloromethane\methanol). The fractions containing product were combined, washed with saturated aqueous sodium bicarbonate, dried (MgSO$_4$), filtered, and concentrated to provide 0.86 g of $N^4$-[4-(4-amino-1H-imidazo[4,5-c]quinolin-1-yl)butyl]morpholinecarboxamide as a tan powder, m.p. 177.0–179.5° C. $^1$H NMR (300 MHz, DMSO-$d_6$) δ 5 8.22 (s, 1H), 8.04 (d, J=7.1 Hz, 1H), 7.64 (d, J=7.5 Hz, 1H), 7.47 (t, J=7.1 Hz, 1H), 7.28 (t, J=7.1 Hz, 1H), 6.72 (broad s, 2H), 6.52 (t, J=5.4 Hz, 1H), 4.61 (t, J=6.9 Hz, 2H), 3.48 (t J=4.6 Hz, 4H), 3.18 (t, J=4.6 Hz, 4H), 3.05 (m, 2H), 1.84 (m, 2H), 1.44 (m, 2H); MS (EI) m/e 368.1966 (368.1961 calcd for $C_{19}H_{24}N_6O_2$).

EXAMPLE 6

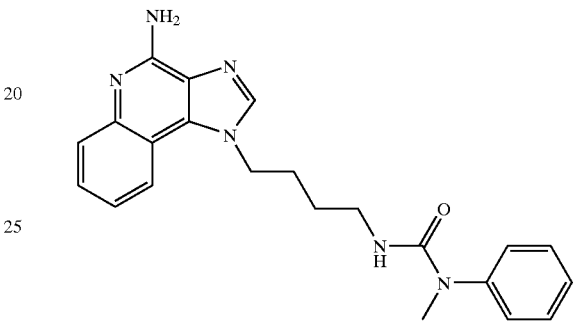

$N^1$-[4-(4-Amino-1H-imidazo[4,5-c]quinolin-1-yl]butyl]-N-methyl-N-phenylurea

According to the general method of Example 5, 1-(4-aminobutyl)-1H-imidazo[4,5-c]quinolin-4-amine and N-methyl-N-phenylcarbamoyl chloride were combined to provide $N^1$-[4-(4-amino-1H-imidazo[4,5-c]quinolin-1-yl) butyl]-N-methyl-N-phenylurea as a tan powder, m.p. 87.0–88.0 ° C. $^1$H NMR (300 MHz, DMSO-$d_6$) δ 8.19 (s, 1H), 8.04 (d, J=8.1 Hz, 1H), 7.63 (dd, J=8.1, 1.2 Hz, 1H), 7.45 (dt, J=8.1, 1.2 Hz, 1H), 7.31–7.24 (m, 3H), 7.18–7.09 (m, 3H), 6.62 (s, 2H), 5.95 (broad s, 1H), 4.59 (t, J=6.9H, 2H), 3.07 (s, 3H), 3.03 (m, 2H), 1.82 (quintet, J=7.2 Hz, 2H), 1.42 (quintet, J=7.2 Hz, 2H); MS (EI) m/e 388.2023 (388.2012 calcd for $C_{22}H_{24}N_6O$).

EXAMPLE 7

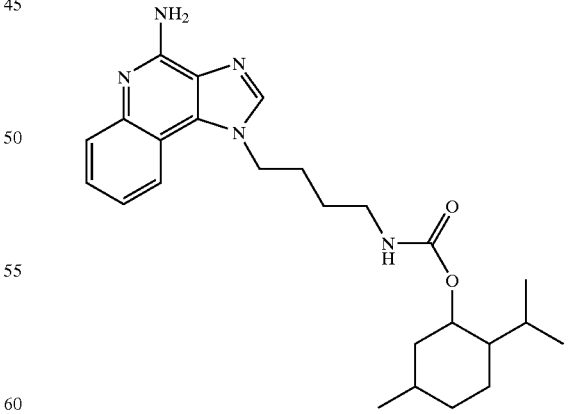

(1R,2S,5R)-2-[sopropyl-5-methylcyclohexyl N-[3-(4-amino-1H-imidazo[4,5-c]quinolin-1-yl)butyl]carbamate (−)-Menthyl chloroformate (0.675 ml, 3.15 mmol) was added dropwise to a stirring solution of 1-(4-aminobutyl)-1H-imidazo[4,5-c]quinolin-4-amine (0.80 g, 3.14 mmol) and pyridine (200 ml). The reaction was maintained at room temperature overnight. The solvent was removed in vacuo and the residue was purified by flash column chromatography (silica gel, 95:5 dichloromethane\methanol). The fractions containing product were combined, washed with saturated aqueous sodium bicarbonate, dried (MgSO$_4$), filtered, and concentrated to provide 0.32 g of (1R,2S,5R)2-isopropyl-5-methylcyclohexyl N-[3-(4-amino-1H-imidazo[4,5-c]quinolin-1-yl)butyl]carbamate as a tan powder, m.p. 84.0–86.0° C. $^{13}$C NMR (75 MHz, DMSO-d$_6$) δ 156.5, 152.5, 145.3, 143.1, 131.9, 128.5, 127.0, 126.5, 121.5, 120.8, 115.2, 73.0, 47.2, 46.5, 41.7, 34.1, 31.2, 27.5, 26.8, 26.1, 23.4, 22.3, 20.8, 16.6; MS (EI) m/e 437.2797 (437.2791 calcd for C$_{25}$H$_{35}$N$_5$O$_2$).

EXAMPLE 8

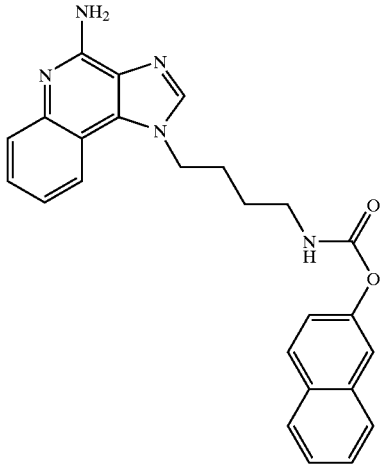

2-Naphthyl N-[4-(4-amino-1H-imidazo[4,5-c]quinolin-1-yl)butyl]carbamate

According to the general method of Example 7, 1-(4-aminobutyl)-1H-imidazo[4,5c]quinolin-4-amine and chloroformic acid 2-naphthyl ester were combined to provide 2-naphthyl N-[4-(4-amino-1H-imidazo[4,5-c]quinolin-1-yl)butyl]carbamate as a white powder, m.p. 154.0–155.0° C. $^1$H NMR (300 MHz, DMSO-d$_6$) δ 8.23 (s, 1H), 8.08 (d, J=7.4 Hz, 1H), 7.94–7.86 (m, 4H), 7.64 (dd, J=8.3, 1.0 Hz, 1H), 7.56–7.43 (m, 4H), 7.30 (m, 1H), 7.20 (dd, J=8.8, 2.3 Hz, 1H), 6.61 (broad s, 2H), 4.65 (t, J=6.9 Hz, 2H), 3.14 (q, J=6.4 Hz, 2H), 1.94 (m, 2H), 1.56 (m, 2H); MS (EI) m/e 426.1927 (426.1930 calcd for C$_{25}$H$_{23}$N$_5$O$_2$).

EXAMPLE 9

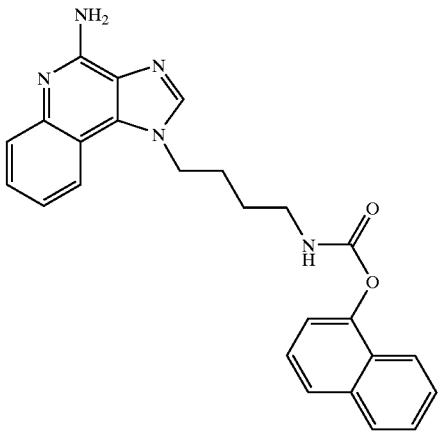

1-Naphthyl N-[4-(4-amino-1H-imidazo[4,5-c]quinolin-1-yl)butyl]carbamate

According to the general method of Example 7, 1-(4-aminobutyl)-1H-imidazo[4,5-c]quinolin-4-amine and chloroformic acid 1-naphthyl ester were combined to provide 1-naphthyl N-[4-(4-amino-1H-imidazo[4,5-c]quinolin-1-yl)butyl]carbamate as a tan powder, m.p. 89.0–92.0° C. $^1$H NMR (300 MHz, DMSO-d$_6$) δ 8.25 (s, 1H), 8.10 (d, J=7.4 Hz, 1H), 8.05 (t, J=5.8 Hz, 1H), 7.96 (d, J=7.6 Hz, 1H), 7.79 (d, J=8.2 Hz, 1H), 7.66–7.45 (m, 6H), 7.30 (m, 1H), 7.19 (d, J=7.5 Hz, 1H), 6.72 (broad s, 2H), 4.67 (t, J=6.9 Hz, 2H), 3.17 (q, J=6.3 Hz, 2H), 1.96 (m, 2H), 1.59 (m, 2H); MS (EI) m/c 426.1929 (426.1930 calcd for C$_{25}$H$_{13}$N$_5$O$_2$).

EXAMPLE 10

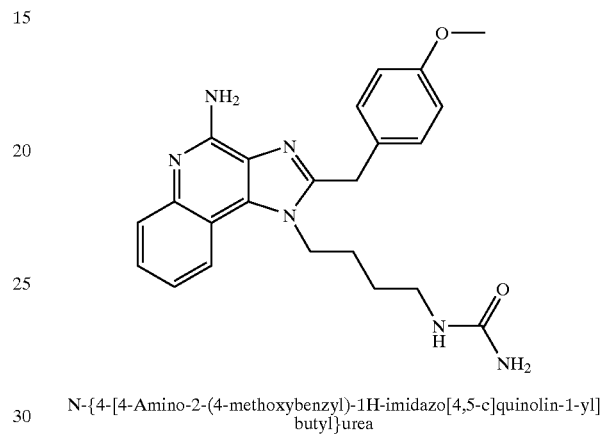

N-{4-[4-Amino-2-(4-methoxybenzyl)-1H-imidazo[4,5-c]quinolin-1-yl]butyl}urea

Part A tert-Butyl N-{4-[2-(4-methoxybenzyl)-1H-imidazo[4,5-c]quinolin-1-yl]butyl}carbamate was reacted according to the general method of Example 1 parts D and E to provide tert-butyl N-aminocarbonyl-N-(4-[4-amino-2-(4-methoxybenzyl)-1H-imidazo[4,5-c]quinolin-1-yl]butyl carbamate as a solid. $^1$H NMR (300 MHz, DMSO-d$_6$) δ 7.93 (d, J=8.1 Hz, 1H), 7.86 (broad s, 1H), 7.61 (dd, J=8.3, 1.1 Hz, 1H), 7.41 (m, 1H), 7.24–7.17 (m, 4H), 6.87 (d, J=8.7 Hz, 2H), 6.55 (broad s, 2H), 4.45 (broad s, 2H 2H), 3.71 (s,3H),3.49 (m, 2H), 1.49 (m, 4H), 1.31 (s, 9H).

Part B

The tert-butyl carbamoyl group was removed from tert-butyl N-aminocarbonyl-N-{4-[4-amino-2-(4-methoxybenzyl)-1H-imidazo[4,5-c]quinolin-1-yl]butyl}carbamate by heating the compound in a solution of HCl and ethanol. The reaction was neutralized (NH$_4$OH) to provide N-{4-[4-amino-2-(4-methoxybenzyl)-1H-imidazo[4,5-c]quinolin-1-yl]butyl}urea as an off white solid, m.p. 196° C. (decomposition). $^1$H NMR (300 MHz, DMSO-d$_6$) δ 7.96 (d, J=7.9 Hz, 1H), 7.61 (d, J=8.3 Hz, 1H), 7.43 (t, J=7.6 Hz, 1H), 7.25 (m, 3H), 6.89 (d, J=8.6 Hz, 2H), 6.58 (broad s, 2H), 5.92 (broad s, 1H), 5.36 (broad s, 2H), 4.41 (m, 2H), 4.32 (s, 2H), 3.72 (s, 3H), 2.93 (d, J=5.8 Hz, 2H), 1.48 (m, 4H); MS (CI) m/e 419

EXAMPLE 11

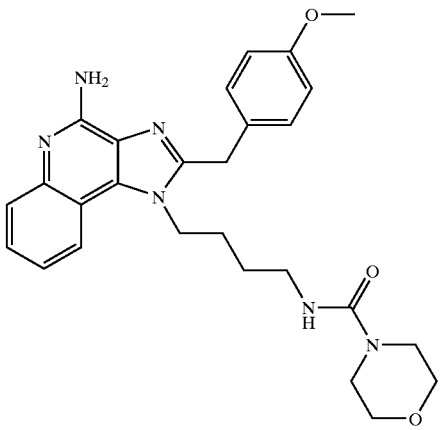

N1-{4-[4-Amino-2-(2-methoxybenzyl)-1H-imidazo[4,5-c]quinolin-1-yl]butyl}-4-morpholinecarboxamide According to the general method of Example 5, 1-(4-aminobutyl)-2-(4-methoxybenzyl)-1H-imidazo[4,5-c]quinolin-4-amine and 4-morpholinecarbonyl chloride were combined to provide N4-{4-[4-amino-2-(2-methoxybenzyl)-1H-imidazo[4,5-c]quinolin-1-yl]butyl}-4-morpholinecarboxamide. $^1$H NMR (300 MHz, CDCl$_3$) δ 7.85–7.81 (m, 2H), 750 (m, 1H), 7.30 (m, 2H), 7.17 (d, J=8.6 Hz, 2H), 6.86 (d, J=8.6 Hz, 2H), 5.62 (broad s, 2H), 4.36 (m, 2H), 4.31 (s, 2H), 3.78 (s, 3H), 3.64 (t, J=4.9 Hz, 3.25 (t, J=4.9 Hz, 4H), 3.18 (m, 2H), 1.70 (m, 2H), 1.54 (m, 2H); MS (EI) m/e 488.2533 (488.2536 calcd for $C_{27}H_{32}N_6O_3$).

EXAMPLE 12

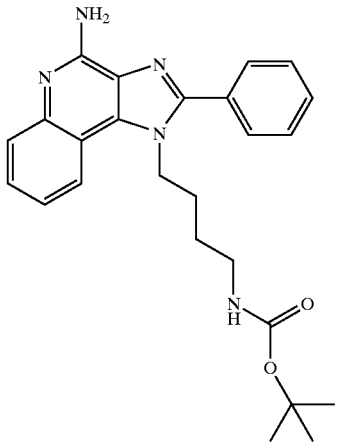

tert-Butyl N-[4-(4-Amino-2-phenyl-1H-imidazo[4,5-c]quinolin-1-l)butyl]carbamate

Part A

A solution of benzoyl chloride (5.3 g, 37.7 mmol) in dichloromethane (100 mL) was slowly added to a solution of tert-butyl N-14-[(3-aminoquinolin4-yl)amino]butyl) carbamate (12.5 g, 37.7 mmol) in dichloromethane (250 mL) at ambient temperature. The reaction mixture was maintained at ambient temperature overnight. The resulting precipitate was isolated by filtration and dried to provide 11.0 g of tert-butyl N-(4-{[3-(benzoylamino)quinolin-4-yl] amino}butyl)carbamate hydrochloride as a white solid.

Part B

Triethylamine (7.26 g, 71.7 mmol) was added to a solution of the material from Part A in ethanol (200 mL) and heated at reflux for 2 days. The reaction mixture was concentrated to provide an orange syrup. HPLC mass spec analysis showed that the syrup contained the desired product and starting material. The syrup was taken up in dichloromethane (100 mL) and then cooled in an ice bath. Triethylamine (5 mL) and benzoyl chloride (1.9 mL) were added. The reaction mixture was maintained at ambient temperature for 2 days at which time analysis by HPLC indicated that the reaction was not complete. The reaction mixture was concentrated under vacuum. The residue was taken up in isopropyl alcohol (150 mL). Triethylamine (5 mL) was added and the reaction mixture was heated at reflux overnight. The reaction mixture was concentrated under vacuum. The residue was purified by flash chromatography (silica gel; eluting with 10% methanol in dichloromethane). The fractions containing product were combined and concentrated under vacuum. The residue was recrystallized from acetonitrile to provide 6.7 g of tert-butyl N-[4-(2-phenyl-1H-imidazo[4,5-c]quinolin-1-yl)butyl]carbamate as a solid, m.p. 158–159° C.

Part C

3-Chloroperoxybenzoic acid (1.05 eq of 65%) was slowly added in small portions to a solution of tert-butyl N-[4-(2-phenyl-1H-imidazo[4,5-c]quinolin-1-yl)butyl]carbamate (6.56 g, 15.75 mmol) in dichloromethane (120 mL). After 3 hours the reaction was quenched with 1% aqueous sodium bicarbonate (200 mL). The layers were separated. The aqueous layer was extracted with dichloromethane (2×50 mL). The organic fractions were combined, dried over magnesium sulfate and then concentrated under vacuum to provide a pale orange syrup. The syrup was triturated with diethyl ether to provide 6.8 g of 1-[4-(tert-butylcarbamyl) butyl]-2-phenyl-1H-imidazo[4,5-c]quinoline-5N-oxide as a pale tan solid, m.p. 178–181° C.

Part D

A solution of 1-[4-(tert-butylcarbamyl)butyl]-2-phenyl-1H-imidazo[4,5-c]quinoline-5N-oxide (6.8 g, 15.75 mmol) in dichloromethane (100 mL) was chilled in an ice bath. Concentrated ammonium hydroxide (30 mL) was added. Tosyl chloride (3.0 g, 15.75 mmol) was added in small portions over a period of 30 minutes. The reaction mixture was allowed to warm to ambient temperature overnight. The reaction was quenched with water (350 mL). The layers were separated. The aqueous layer was extracted with dichloromethane. The organic fractions were combined, dried over magnesium sulfate and then concentrated under vacuum to provide a tan solid. This material was purified by flash chromatography (silica gel eluting with 10% methanol in dichloromethane) to provide 4.8 g of product. A small portion was recrystallized from toluene to provide tert-butyl N-[4-(4-amino-2-phenyl-1H-imidazo[4,5-c]quinolin-1-yl) butyl]carbamate as a solid, m.p. 182–183° C. Analysis: Calculated for $C_{25}H_{29}N_5O_2$: %C, 69.58; %H, 6.77; %N. 16.22; Found: %C, 69.86; %H, 6.95; %N, 15.80.

EXAMPLE 13

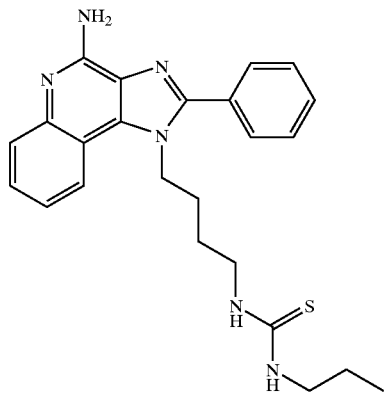

N-[4-(4-Amino-2-phenyl-1H-imidazo[4,5-c]quinolin-1-yl)butyl]-N'-propylthiourea

Part A

The tert-butyl N-[4-(4-amino-2-phenyl-1H-imidazo[4,5-c]quinolin-1-yl)butyl]carbamate (4.3 g, 10.0 mmol) was dissolved in methanol (15 mL) and 1 N hydrochloric acid (100 mL) and then heated at reflux for 2 hours. The reaction mixture was concentrated under vacuum to a volume of about 50 mL. Addition of concentrated ammonium hydroxide to pH 12 did not produce a precipitate. The pH was adjusted to 7 with 1 N hydrochloric acid. The mixture was extracted with dichloromethane and then with ethyl acetate. The aqueous layer was concentrated to dryness. The residue was dissolved in water (50 mL) and then extracted continuously with refluxing chloroform for 36 hours. The chloroform extract was concentrated under vacuum to provide a light tan solid. This material was recrystallized from acetonitrile to provide 2.5 g of 1-(4-aminobutyl)-2-phenyl-1H-imidazo[4,5-c]quinolin4-amine as an off white solid, m.p. 175–177° C. Analysis: Calculated for $C_{20}H_{21}N_5$: %C, 72.48; %H, 6.39; %N, 21.13; Found: %C, 72.72; %H, 6.32; %N, 20.71.

Part B

A solution of propyl isothiocyanate (0.78 g, 7.72 mmol) in chloroform (5 mL) was added at ambient temperature to a solution of 1-(4-aminobutyl)-2-phenyl-1H-imidazo[4,5-c]quinolin-4-amine (0.256 g, 7.72 mmol) in a mixture of chloroform (25 mL) and pyridine (5 mL). The reaction mixture was maintained at ambient temperature over the weekend. The reaction was quenched with ethanol and then concentrated under vacuum to provide a pale orange syrup. This material was purified by flash chromatography (silica gel, eluting with 10% methanol in dichloromethane). The pure fractions were combined and concentrated under vacuum to provide 0.22 g of N-[4-(4-amino-2-phenyl-1H-imidazo[4,5-c]quinolin-1-yl)butyl]-N'-propylthiourea as a white solid, m.p. 113–116° C. Mass spec M+1=433.2.

EXAMPLE 14

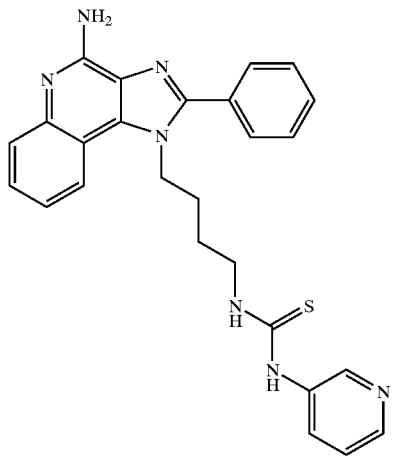

N-[4-(4-Amino-2-phenyl-1H-imidazo[4,5-c]quinolin-1-yl)butyl]-N'-(3-pyridyl)thiourea A solution of pyridine-3-isothiocyanate (0.136 g, 1.0 mmol) in chloroform (5 mL) was added at ambient temperature to a solution of 1-(4-aminobutyl)-2-phenyl-1H-imidazo[4,5-c]quinolin-4-amine (0.331 g, 1.0 mmol) in a mixture of chloroform (25 mL) and pyridine (5 mL). The reaction mixture was maintained at ambient temperature over the weekend. The reaction was quenched with ethanol and then concentrated tinder vacuum to provide an off-white solid. This material was purified by flash chromatography (silica gel, eluting with 10% methanol in dichloromethane). The pure fractions were combined and concentrated under vacuum to provide 0.2 g of N-[4-(4-amino-2-phenyl-1H-imidazo[4,5-c]quinolin-1-yl)butyl]-N'-(3-pyridyl)thiourea as a white solid, m.p. 118–120° C. Mass spec M+1=468.3. Analysis: Calculated for $C_{26}H_{25}N_7S$: %C, 66.79; %H, 5.39; %N, 20.97; Found: %C, 64.29; %H, 5.46; %N, 20.06.

EXAMPLE 15

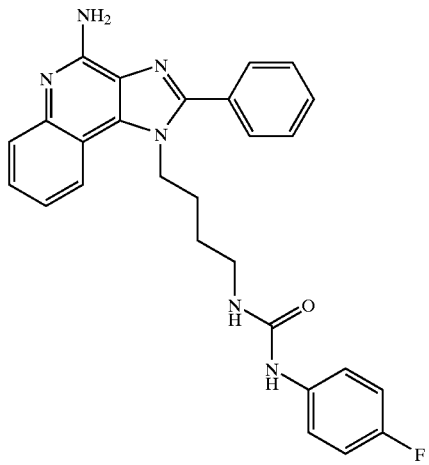

N-[4-(4-amino-2-phenyl-1H-imidazo[4,5-c]quinolin-1-yl)butyl]-N'-(4-fluorophenyl)urea A solution of 4fluorophenylisocyanate (0.137 g, 1.0 mmol) in chloroform (5 mL) was added at ambient temperature to a solution of 1-($^4$-aminobutyl)2-phenyl-1H- imidazo[4,5c]quinolin-4-amine (0.331 g, 1.0 mmol) in a mixture of chloroform (25 mL) and pyridine (5 mL). The reaction mixture was maintained at ambient temperature over the weekend. The reaction was quenched with ethanol. The resulting pale yellow precipitate (identified as the bis-adduct) was isolated by filtration. The filtrate was concentrated under vacuum to provide an off-white solid. This material was purified by flash chromatography (silica gel, eluting with 10% methanol in dichloromethane). The pure fractions were combined and concentrated under vacuum to provide 0.22 g of N-[4-(4-amino-2-phenyl-1H-imidazo[4,5-c]quinolin-1-yl)butyl]-N'-(4-fluorophenyl)urea as a white solid, m.p. 145–150° C. Mass spec M+1=469.2. Analysis: $C_{27}H_{25}FN_6O$: %C, 69.21; %H, 5.37; %N, 17.94; Found: %C, 66.70; %H, 5.33; %N, 17.03.

EXAMPLES 16–52

The compounds shown in the table below were made according to the synthetic method of Reaction Scheme II above.

A solution of 1-(4-aminobutyl)-1H-imidazo[4,5c]quinolin-4-amine (36 µmol) in 10 mL of dichloromethane in a screw-capped test tube was cooled down to −5° C. The isocyanate (45 µmol) was added as a 0.3 M solution in dichloromethane. Argon was bubbled through the mixture during addition and for an additional 15 seconds, and the mixture was allowed to stand at −5° C. overnight. To this mixture was added approximately 90 mg of an aminomethyl polystyrene resin (0.62 meq/g, 100–200 mesh), and the mixture was warmed to reflux and shaken at about 600 rpm for 3 hours. The mixtures were filtered through Poly-Prep columns (BioRad #731-1550) to remove resin. Three different purification methods were used. In Method A the filtrate was loaded onto a silica gel column. The column was eluted with 10:1 dichloromethane:methanol and the fractions containing product were combined and dried in vacuo. In Method C the filtrates were dried in vacuo and purified by semi-preparative hplc on a Gilson system (Rainin Microsorb C18 column, 21.4×250 mm, 8 micron particle size, 60A pore, 10 mL/min., gradient elution from 2–95% B in 25 min., hold at 95% B for 5 min., where A=0.1% trifluoroacctic acid/water and B=0.1% Trifluoroacetic acid/acetonitrile, peak detection at 254 nm for triggering fraction collection). The semi-prep hplc fractions were analyzed by LC-APCI/MS and the appropriate fractions were lyophilized to provide the compounds as trifluoroacetate salts. In Method B the compounds were purified by Method C and then the trifluoroacetate salts were dissolved in ca. 3–5 mL of 2:1 dichloromethane-methanol and shaken with ca. 80 mg (300 µmol) of diisopropylaminomethyl-polystyrene resin (Argonaut PS-DIEA, 3.86 mmol/g) for 1–2 h to liberate the free amine, and then filtered and dried in vacuo. The compounds were generally amorphous solids.

| Example No. | Structure | Purification | APCI-MS m/e | 500 MHz $^1$H NMR |
|---|---|---|---|---|
| 16 | 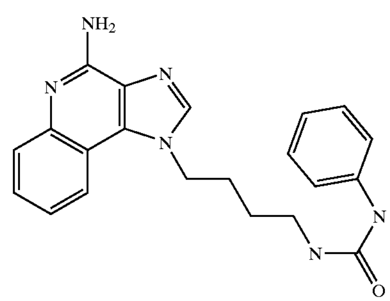 | A | 375.19 | (DMSO-$d_6$) δ 8.38(s, 1H), 8.22(s, 1H), 8.05(d, J=7.9Hz, 1H), 7.61(d, 7.9Hz, 1H), 7.43(t, J=7.6Hz, 1H), 7.36(d, J=7.3Hz, 2H), 7.24(t, J=7.3Hz, 1H), 7.20(t, J=7.9Hz, 2H), 6.87(t, J=7.3Hz, 1H), 6.60(bs, 2H), 6.14(t, J=5.8Hz, 1H), 4.63(t, J=7Hz, 2H), 3.15(q, J=6Hz, 2H), 1.88(quintet, J=7Hz, 2H), 1.49 (quintet, J=7Hz, 2H) |
| 17 | 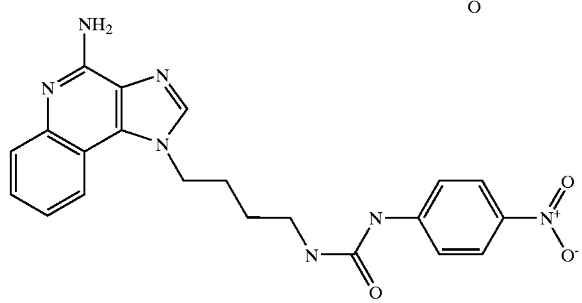 | B | 420.16 | (DMSO-$d_6$) δ 9.37(s, 1H), 8.42(s, 1H), 8.16(d, J=7.8Hz, 1H), 8.12(d, J=9.3Hz, 2H), 7.74(d, J=8.3Hz, 1H), 7.59(m, 3H), 7.43(t, J=6Hz, 1H), 6.58(t, J=5.4Hz, 1H), 4.68(t, J=7Hz, 2H), 3.15 (q, J=6Hz, 2H), 1.89(quintet, J=7.5Hz, 2H), 1.52(quintet, J=7Hz, 2H) |
| 18 | 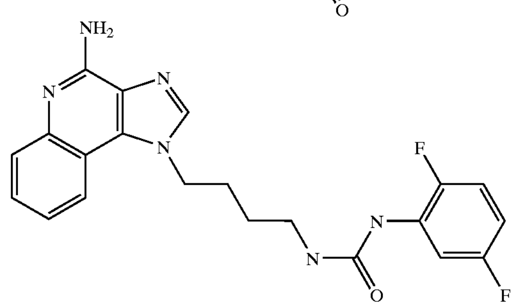 | C | 411.17 | |

-continued

| Example No. | Structure | Purification | APCI-MS m/e | 500 MHz $^1$H NMR |
|---|---|---|---|---|
| 19 | 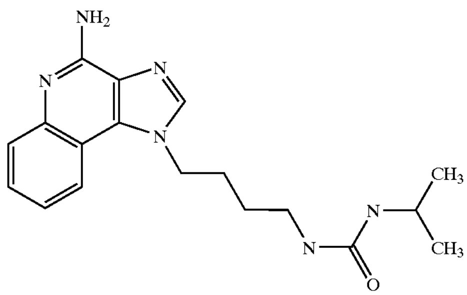 | B | 341.22 | (DMSO-$d_6$) δ 8.40(s, 1H), 8.15(d, J=7.8Hz, 1H), 7.75(d, J=8.1Hz, 1H), 7.62(t, J=7Hz, 1H), 7.46(s, J=7Hz, 1H), 5.71(t, J=7Hz, 1H), 5.60(d, J=8Hz, 1H), 4.65(t, J=6.5Hz, 2H), 3.61(sextet, J=7.5Hz, 1H), 3.01(q, J=6Hz, 2H), 1.84 (quintet, J=7.5Hz, 2H), 1.42(quintet, J=7Hz, 2H), 0.97(d, J=6.5Hz, 6H) |
| 20 | 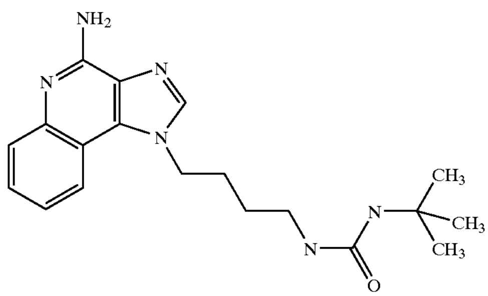 | B | 355.24 | (DMSO-$d_6$) δ 8.42(s, 1H), 8.17(d, J=8.3Hz, 1H), 7.76(d, J=8.3Hz, 1H), 7.64(t, J=8.5Hz, 1H), 7.48(s, 1H), 5.66(t, J=6Hz, 1H), 5.54(s, 1H), 4.66 (t, J=7Hz, 2H), 2.98(q, J=6Hz, 2H), 1.84(quintet, J=8Hz, 2H), 1.41(quintet, J=8Hz, 2H), 1.17(s, 9H) |
| 21 | 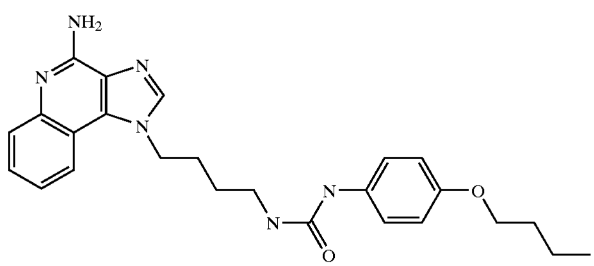 | B | 447.21 | (DMSO-$d_6$) δ 8.43(s, 1H), 8.3(br s, 1H), 8.26(s, 1H), 8.17(d, J=7.8Hz, 1H), 7.75(d, J=8.3Hz, 1H), 7.61(t, J=8.1Hz, 1H), 7.44(t, J=7.8Hz, 1H), 7.23(d, J=6.8Hz, 2H), 6.78(d, J=6.8Hz, 2H), 6.12(t, J=6.1Hz, 1H), 4.68(t, J=7Hz, 2H), 3.88(t, J=6.5Hz, 2H), 3.11(q, J=6Hz, 2H), 1.88(quintet, J=7Hz, 2H), 1.66(quintet, J=8Hz, 2H), 1.49(quintet, J=7Hz, 2H), 1.41(quintet, J=7Hz, 2H), 0.92(t, J=7Hz, 3H) |
| 22 | 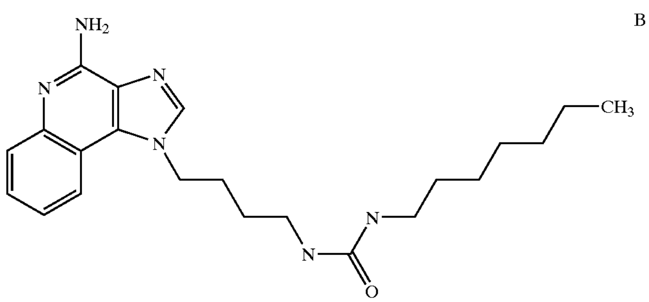 | B | 447.00 | (DMSO-$d_6$) δ 8.39(s, 1H), 8.28(bs, 1H), 8.15(d, J=7.8Hz, 1H), 7.75(d, J=7.8Hz, 1H), 7.61(t, J=7.8Hz, 1H), 7.45(t, J=7.6Hz, 1H), 5.81(t, J=6Hz, 1H), 5.75(t, J=6Hz, 1H), 4.65(t, J=7.5Hz, 2H), 3.02(q, J=6.5Hz, 2H), 2.92(q, J=6.0Hz, 2H), 1.84 (quintet, J=7.5Hz, 2H), 1.43(quintet, J=7Hz, 2H), 1.30(quintet, J=7Hz, 2H), 1.22(bs, J=8Hz, 8H), 0.84(t, J=7.5Hz, 3H) |
| 23 | 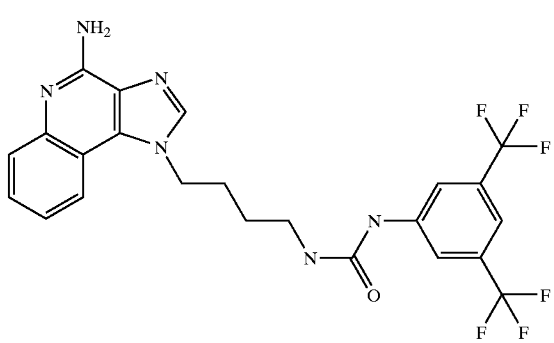 | B | 511.11 | (DMSO-$d_6$) δ 9.6–8.6(b, 2H), 9.35(s, 1H), 8.55(s, 1H), 8.24(d, J=8.0Hz, 1H), 8.06(s, 2H), 7.82(d, J=8.0Hz, 1H), 7.69(t, J=8.0Hz, 1H), 7.55(t, J=8.0Hz, 1H), 7.54(s, 1H), 6.70 (t, J=6.0, 1H), 4.72(t, J=7.5Hz, 2H), 3.15(q, J=6.0Hz, 2H), 1.90(quintet, J=7.0Hz, 2H), 1.54(quintet, J=7.5Hz, 2H) |

-continued

| Example No. | Structure | Purification | APCI-MS m/e | 500 MHz $^1$H NMR |
|---|---|---|---|---|
| 24 | 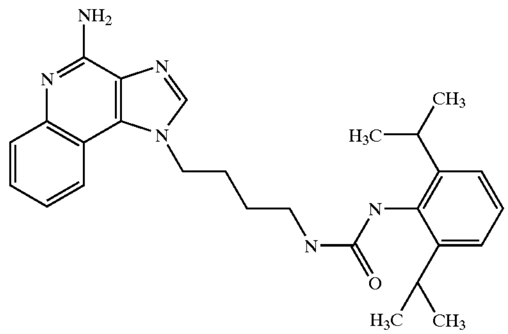 | B | 459.35 | (DMSO-d$_6$) δ 8.32(bs, 1H), 8.28(bs, 1H), 8.13(d, J=8.8Hz, 1H), 7.70(d, J=7.6Hz, 1H), 7.55(t, J=6.8Hz, 1H), 7.38(t, 1H), 7.34(bs, 1H), 7.17(t, J=8Hz, 1H), 7.06(d, J=8Hz, 2H), 6.1(bs, 2H), 4.66(t, J=7.5Hz, 2H), 3.10(bs, 2H), 3.04(quintet, J=7Hz, 1H), 1.88(bm, 2H), 1.48(bm, 2H), 1.02(d, J=7Hz, 12H) |
| 25 | 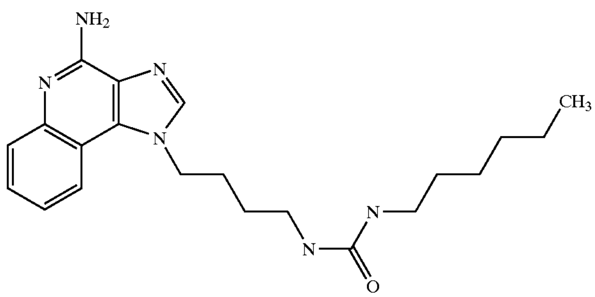 | C | 383.22 | (DMSO-d$_6$) δ 8.52(s, 1H), 8.22(d, J=8Hz, 1H), 7.83(d, J=8Hz, 1H), 7.72(t, J=8Hz, 1H), 7.58(t, J=8Hz, 1H), 5.80(t, J=5Hz, 1H), 5.75(t, J=5.5Hz, 1H), 4.68(t, J=7.0Hz, 2H), 3.02(q, J=6.5Hz, 2H), 2.92(q, J=6Hz, 2H), 1.84(quintet, J=7Hz, 2H), 1.44 (quintet, J=7Hz, 2H), 1.29(t, J=7Hz, 2H), 1.2(m, 6H), 0.84(t, J=7Hz, 3H) |
| 26 | 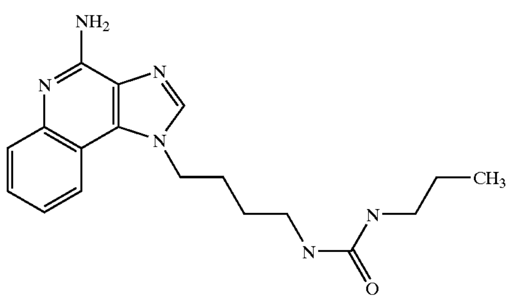 | C | 341.21 | (DMSO-d$_6$) δ 8.52(s, 1H), 8.23(d, J=8Hz, 1H), 7.83(d, J=8Hz, 1H), 7.72(t, J=7.5Hz, 1H), 7.57(t, J=7Hz, 1H), 5.80(t, J=6.5Hz, 1H), 5.77(t, J=6Hz, 1H), 4.68(t, J=7.5Hz, 2H), 3.02(q, J=6.5Hz, 2H), 2.89(q, J=6.5Hz, 2H), 1.84(quintet, J=7.5Hz, 2H), 1.43(quintet, J=8Hz, 2H), 1.31 (sextet, J=7Hz, 2H), 0.78(t, J=7.5Hz, 3H) |
| 27 | 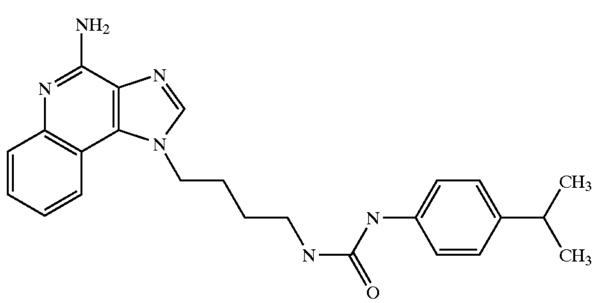 | C | 417.18 | (DMSO-d$_6$) δ 9.6–8.6(b, 2H), 8.55(s, 1H), 8.33(bs, 1H), 8.24(d, J=7.5Hz, 1H), 7.83(d, J=7.5Hz, 1H), 7.72(t, J=7.5Hz, 1H), 7.56(t, J=7.5Hz, 1H), 7.25(d, J=8.0Hz, 2H), 7.06(d, J=8Hz, 2H), 6.17(t, J=5.5Hz, 1H), 4.71(t, J=7.0Hz, 2H), 3.12(q, J=5.5Hz, 2H), 2.79(quintet, J=7.0Hz, 1H), 1.89 (quintet, J=7.0Hz, 2H), 1.51(quintet, J=7.0Hz, 2H), 1.16(d, J=7.0Hz, 6H) |
| 28 | 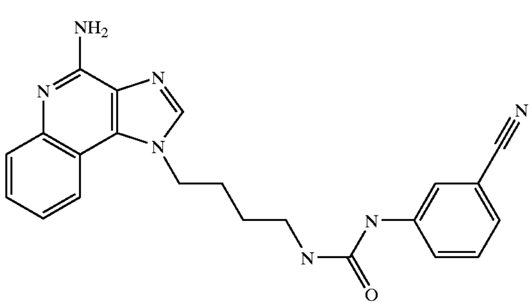 | B | 400.18 | (DMSO-d$_6$) δ 8.88(s, 1H), 8.32(s, 1H), 8.22(bs, 1H), 8.11(d, J=8Hz, 1H), 7.91(t, J=1.7Hz, 1H), 7.68(d, J=8Hz, 1H), 7.55(d, J=9.5Hz, 1H), 7.51(t, J=8.1Hz, 1H), 7.41(t, J=8.3Hz, 1H), 7.34(t, J=7.1Hz, 1H), 6.41(t, J=7Hz, 1H), 4.66(t, J=6.5Hz, 2H), 3.13(q, J=6Hz, 2H), 1.89 (quintet, J=7.5Hz, 2H), 1.50(quintet, J=7Hz, 2H) |

| Example No. | Structure | Purification | APCI-MS m/e | 500 MHz ¹H NMR |
|---|---|---|---|---|
| 29 | 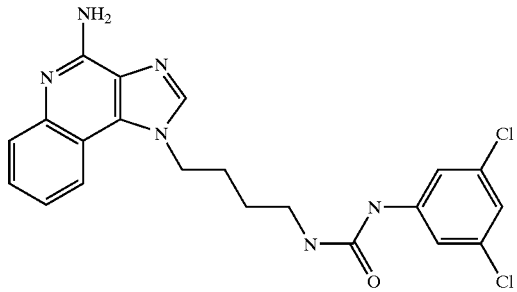 | B | 443.10 | (DMSO-d$_6$) δ 8.97(s, 1H), 8.46(s, 1H), 8.19(d, J=7.8Hz, 1H), 7.77(d, J=8.3Hz, 1H), 7.63(t, J=8.1Hz, 1H), 7.48(t, J=7.3Hz, 1H), 7.44(s, 2H), 7.05(t, J=1.7Hz, 1H), 6.49(t, J=5.6Hz, 1H), 4.69(t, J=7Hz, 2H), 3.12(q, J=6.5Hz, 2H), 1.88(quintet, J=8Hz, 2H), 1.50(quintet, J=7Hz, 2H) |
| 30 | 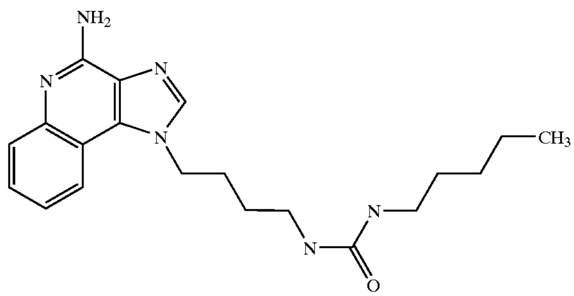 | B | 369.24 | (DMSO-d$_6$) δ 8.80(b, 2H), 8.52(s, 1H), 8.23(d, J=7.5Hz, 1H), 7.84(d, J=8.0Hz, 1H), 7.73(t, J=8.0Hz, 1H), 7.58(t J=7.5Hz, 1H), 5.80(t, J=5.5Hz, 1H), 5.75(t, J=5.5Hz, 1H), 4.68(t, J=7.0Hz, 2H), 3.02(q, J=5.5Hz, 2H), 2.92(q, J=5.5Hz, 2H), 1.84 (quintet, J=7.0Hz, 2H), 1.44(quintet, J=7.0Hz, 2H), 1.30(quintet, J=7.0Hz, 2H), 1.23(quintet, J=7.0Hz, 2H), 1.18(sextet, J=7.0Hz, 2H), 0.83(t, J=7.0Hz, 3H) |
| 31 | 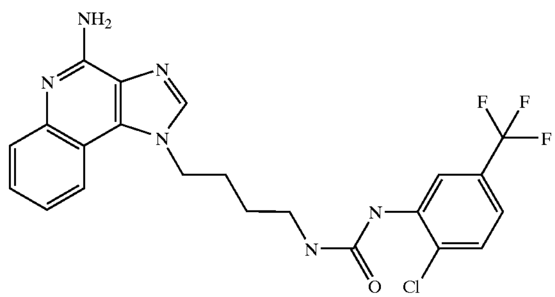 | B | 477.08 | (DMSO-d$_6$) δ 9.6–8.6(b, 2H), 8.60(d, J=2.0Hz, 1H), 8.56(s, 1H), 8.26(s, 1H), 8.25(d, J=8Hz, 1H), 7.82 (d, J=8.0Hz, 1H), 7.69(t, j=8.0Hz, 1H), 7.64(d, J=8.0Hz, 1H), 7.55(t, J=8.0Hz, 1H), 7.28(dd, J=8.0, 2.0Hz, 1H), 7.23(t, J=5.5Hz, 1H), 4.72(t, J=7.0Hz, 2H), 3.16(q, J=5.5Hz, 2H), 1.92(quintet, J=7Hz, 2H), 1.54(quintet, J=7.0Hz, 2H) |
| 32 | 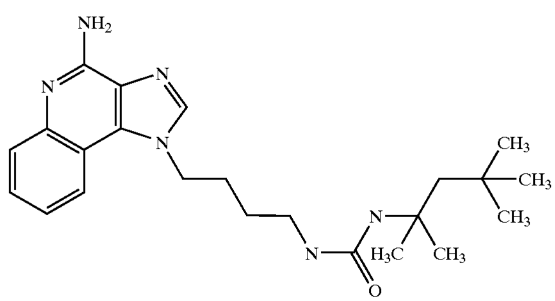 | B | 411.23 | (DMSO-d$_6$) δ 9.6–8.6(b, 2H), 8.53(s, 1H), 8.24(d, J=8.5Hz, 1H), 7.84(d, J=8.5Hz, 1H), 7.74(t, J=8.5Hz, 1H), 7.59(t, J=8.5Hz, 1H), 5.63(t, J=6.0Hz, 1H), 5.44(s, 1H), 4.70(t, J=7.0Hz, 2H), 2.98(q, J=6.0Hz, 2H), 1.83(quintet, J=7.0Hz, 2H), 1.59(s, 2H), 1.40(quintet, J=7.0Hz, 2H), 1.19(s, 6H), 0.84(s, 9H) |
| 33 | 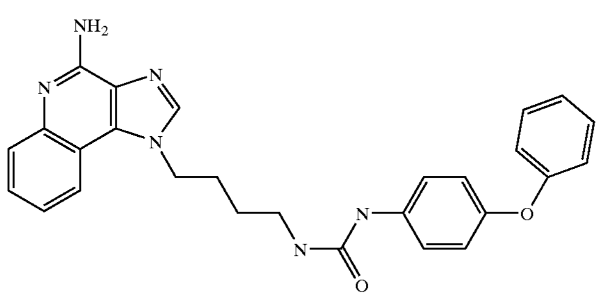 | C | 467.21 | |

| Example No. | Structure | Purification | APCI-MS m/e | 500 MHz ¹H NMR |
|---|---|---|---|---|
| 34 | 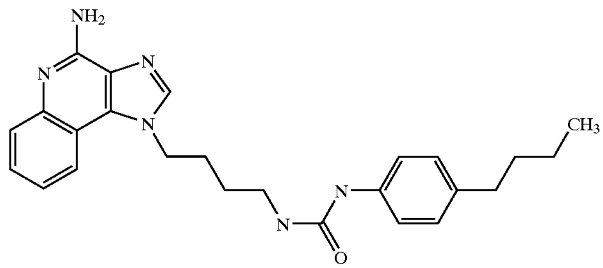 | C | 431.26 | |
| 35 | 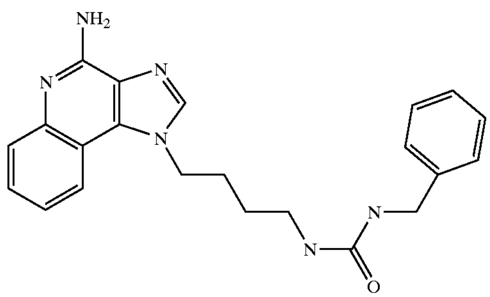 | C | 389.20 | |
| 36 | 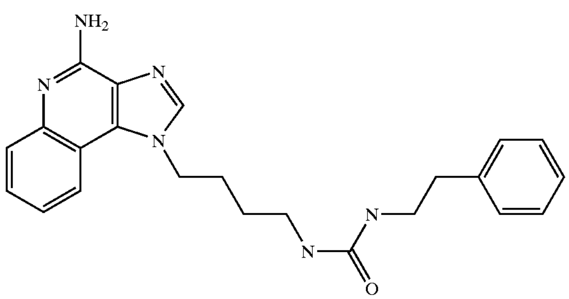 | C | 403.22 | |
| 37 | 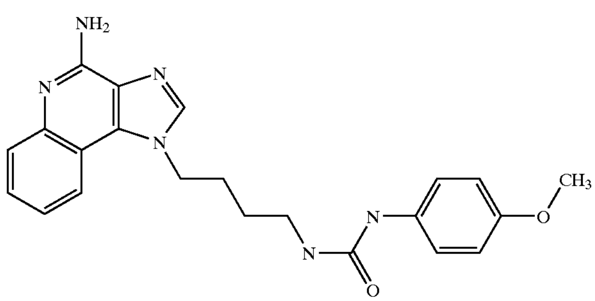 | C | 405.19 | |
| 38 | 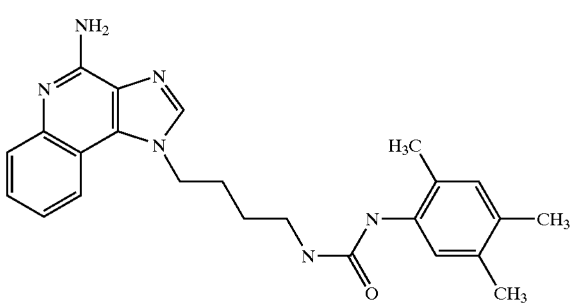 | C | 417.24 | |

-continued

| Example No. | Structure | Purification | APCI-MS m/e | 500 MHz ¹H NMR |
|---|---|---|---|---|
| 39 | 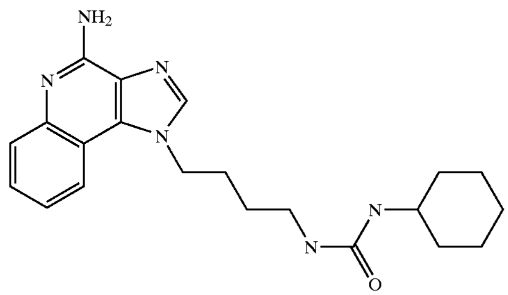 | C | 381.26 | |
| 40 | 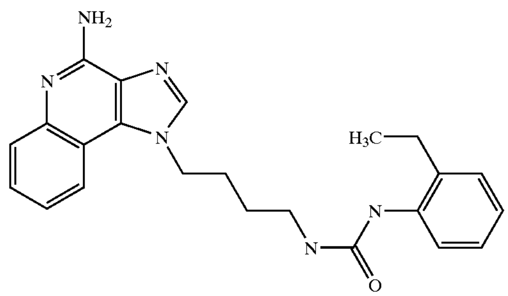 | C | 403.23 | |
| 41 | 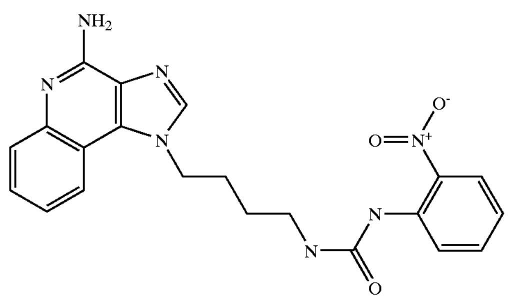 | C | 420.18 | |
| 42 | 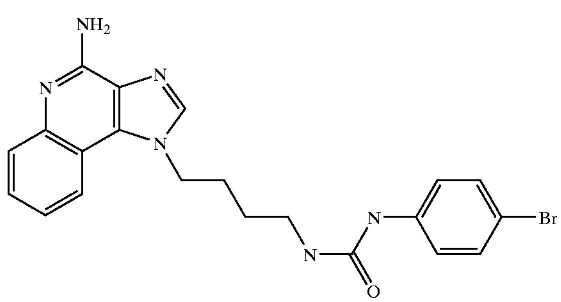 | C | 453.09 | |
| 43 | 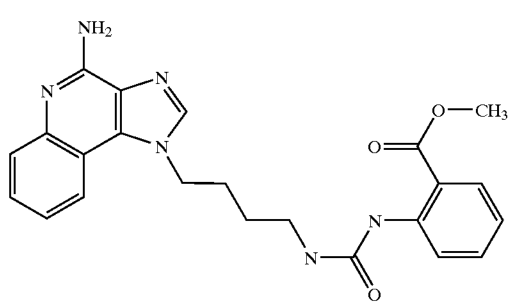 | C | 433.18 | |

-continued

| Example No. | Structure | Purification | APCI-MS m/e | 500 MHz ¹H NMR |
|---|---|---|---|---|
| 44 | 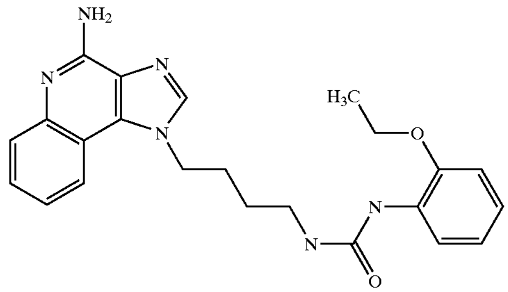 | C | 419.18 | |
| 45 | 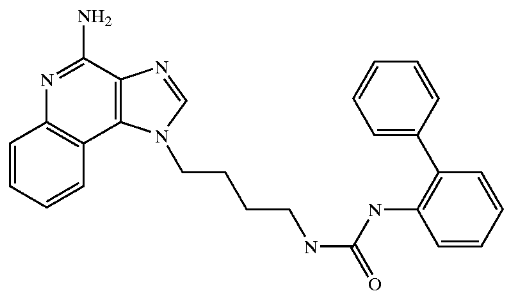 | C | 451.17 | |
| 46 | 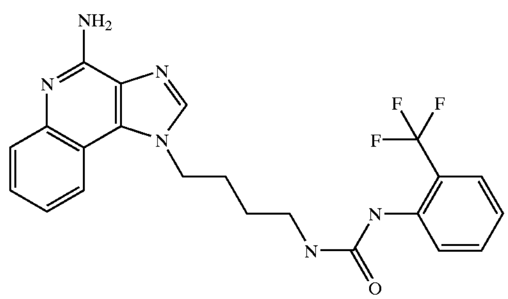 | C | 443.14 | |
| 47 | 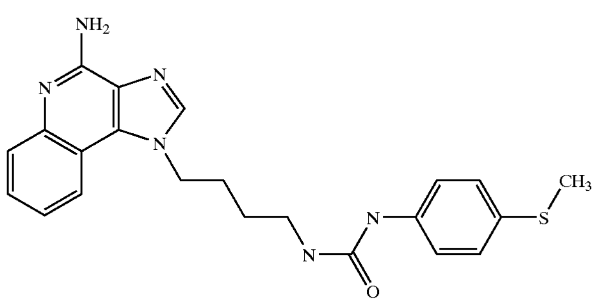 | C | 421.14 | |
| 48 | 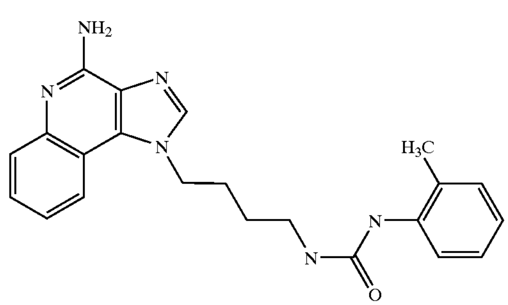 | C | 389.18 | |

| Example No. | Structure | Purification | APCI-MS m/e | 500 MHz ¹H NMR |
|---|---|---|---|---|
| 49 | 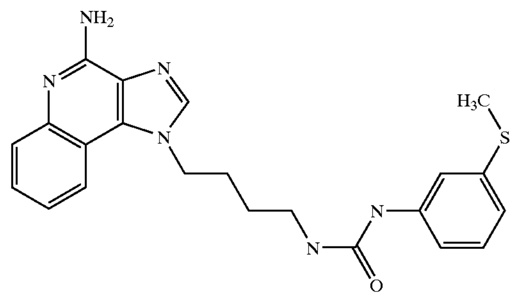 | C | 421.14 | |
| 50 | 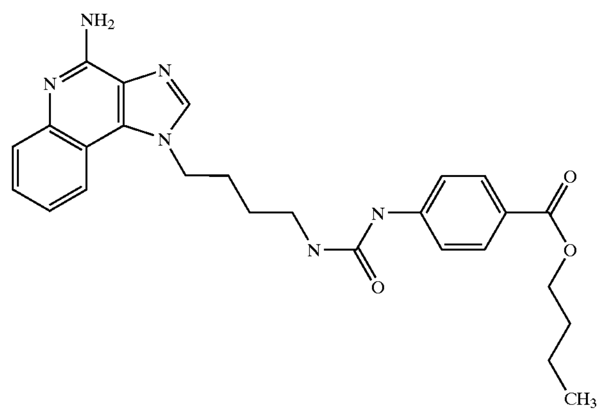 | C | 475.20 | |
| 51 | 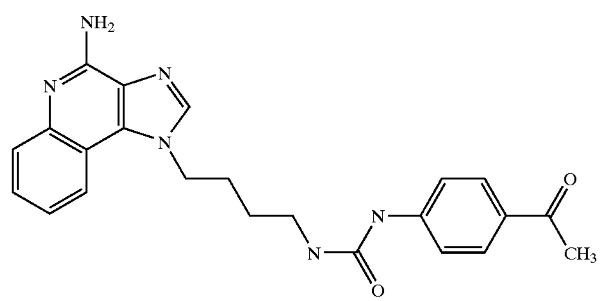 | C | 417.20 | |
| 52 | 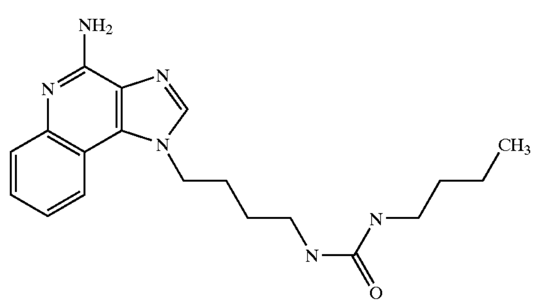 | C | 355.21 | |

EXAMPLES 53–66

The examples in the table below were prepared according to the synthetic method of Reaction Scheme II above using the following general method. 1-(2-Aminoethyl)-2-butyl-1H-imidazo[4,5-c]quinolin-4-amine (50 mg), dichloromethane (2 mL) and the isocyanate were placed in a 2 dram (7.4 mL) vial. The vial was placed on a shaker for about 2–16 hours at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired urea.

| Example # | Structure of the Free Base | mass |
|---|---|---|
| 53 | (4-amino-2-butyl-imidazoquinoline with ethyl-NH-C(O)-NH-adamantyl substituent) | 461.2 |
| 54 | (4-amino-2-butyl-imidazoquinoline with ethyl-NH-C(O)-NH-(4-phenoxyphenyl) substituent) | 495.1 |
| 55 | (4-amino-2-butyl-imidazoquinoline with ethyl-NH-C(O)-NH-benzyl substituent) | 417.1 |
| 56 | (4-amino-2-butyl-imidazoquinoline with ethyl-NH-C(O)-NH-propyl substituent) | 369.2 |
| 57 | (4-amino-2-butyl-imidazoquinoline with ethyl-NH-C(O)-NH-ethyl substituent) | 355 |
| 58 | (4-amino-2-butyl-imidazoquinoline with ethyl-NH-C(O)-NH-isopropyl substituent) | 369.2 |
| 59 | (4-amino-2-butyl-imidazoquinoline with ethyl-NH-C(O)-NH-butyl substituent) | 383.3 |
| 60 | (4-amino-2-butyl-imidazoquinoline with ethyl-NH-C(O)-NH-phenyl substituent) | 403.2 |

| Example # | Structure of the Free Base | mass |
|---|---|---|
| 61 | | 417.2 |
| 62 | | 417.2 |
| 63 | | 417.2 |
| 64 | | 428.2 |
| 65 | | 431.2 |
| 66 | | 431.2 |

EXAMPLES 67–69

The examples in the table below were prepared using the following method. 1-(2-Aminoethyl)-2-ethoxymethyl-1H-imidazo[4,5-c]quinolin4-amine hydrochloride (50 mg), dichloromethane (2 mL) and diisopropylethylamine (1.2 eq) were placed in a 2 dram (7.4 mL) vial. The vial was placed on a shaker for about 1 hour al ambient temperature. The appropriate (thio)isocyanate was added and the vial was shaken at ambient temperature for about 4 hours. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired (thio)urea.

| Example # | Structure of the Free Base | Mass |
|---|---|---|
| 67 | 4-amino-2-(ethoxymethyl)-1H-imidazo[4,5-c]quinoline with 1-N-(2-(3-propylureido)ethyl) substituent | 371.1 |
| 68 | 4-amino-2-(ethoxymethyl)-1H-imidazo[4,5-c]quinoline with 1-N-(2-(3-phenylureido)ethyl) substituent | 405.1 |
| 69 | 4-amino-2-(ethoxymethyl)-1H-imidazo[4,5-c]quinoline with 1-N-(2-(3-cyclohexylthioureido)ethyl) substituent | 427.1 |

EXAMPLES 70–99

The examples in the table below were prepare according to the synthetic method of Reaction Scheme II above by reacting 1-(4-aminobutyl)-2-butyl-1H-imidazo[4,5-c]quinolin-4-amine with the appropriate isocyanate using the general method of Examples 53–66 above.

| Example # | Structure of the Free Base | Mass |
|---|---|---|
| 70 | 4-amino-2-butyl-1H-imidazo[4,5-c]quinoline with 1-N-(4-(3-allylureido)butyl) substituent | 395.2 |
| 71 | 4-amino-2-butyl-1H-imidazo[4,5-c]quinoline with 1-N-(4-(3-ethylureido)butyl) substituent | 397.3 |

-continued
| Example # | Structure of the Free Base | Mass |
|---|---|---|
| 72 | 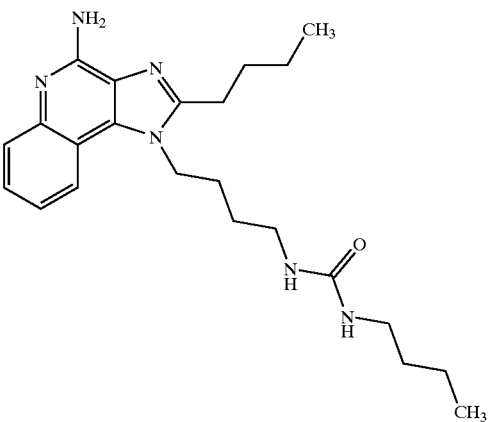 | 411.3 |
| 73 | 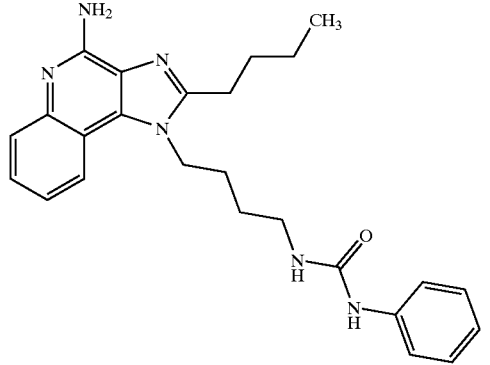 | 431.2 |
| 74 | 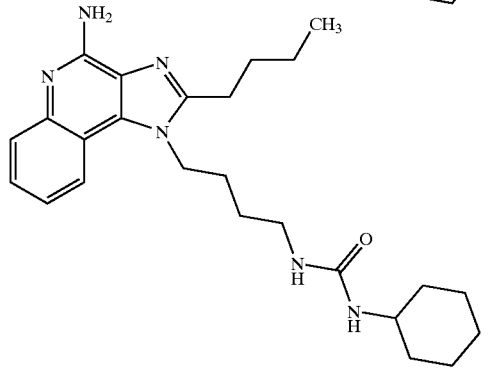 | 437.3 |
| 75 | 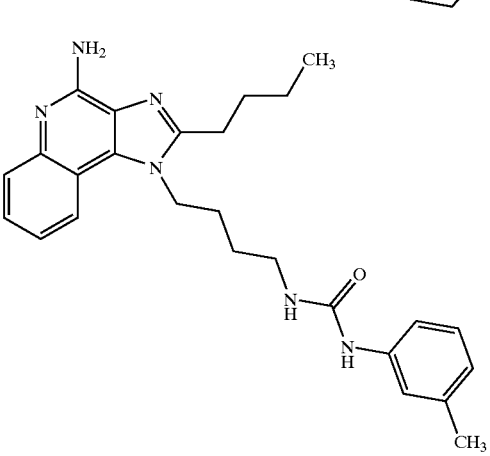 | 445.2 |

-continued

| Example # | Structure of the Free Base | Mass |
|---|---|---|
| 76 | | 445.20 |
| 77 | | 445.2 |
| 78 | | 449.2 |
| 79 | | 449.2 |

| Example # | Structure of the Free Base | Mass |
|---|---|---|
| 80 | 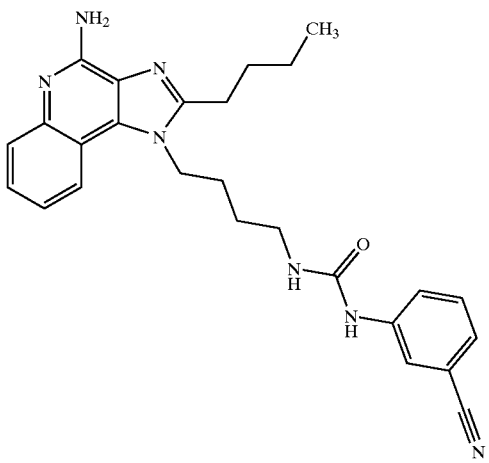 | 456.2 |
| 81 | 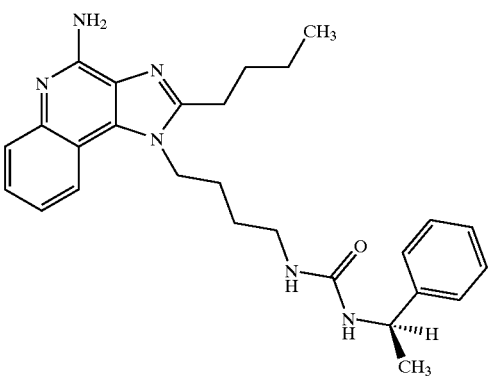 | 459.3 |
| 82 | 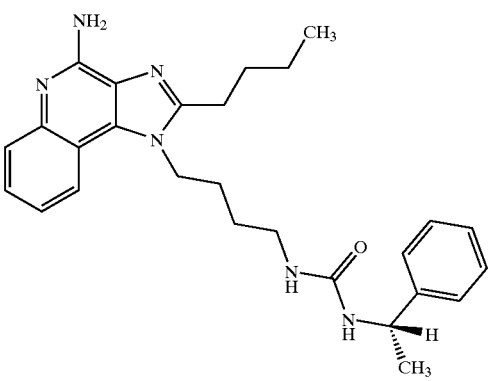 | 459.3 |

-continued
| Example # | Structure of the Free Base | Mass |
|---|---|---|
| 83 | 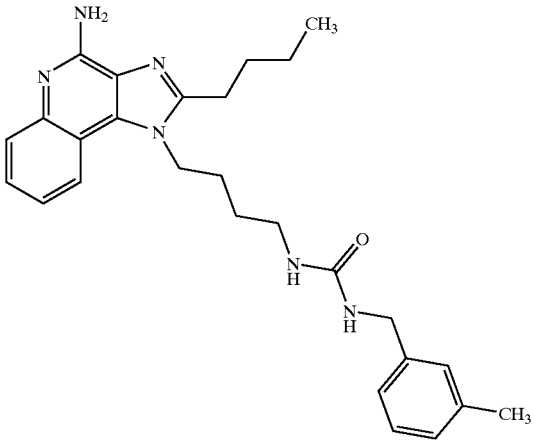 | 459.3 |
| 84 | 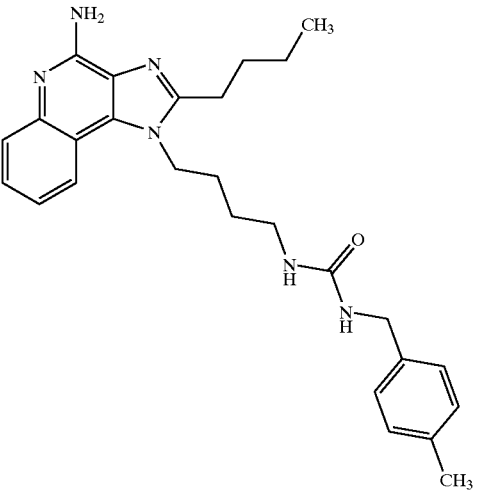 | 459.3 |
| 85 | 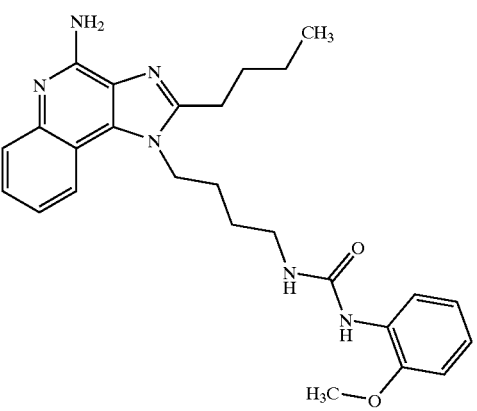 | 461.3 |

-continued
| Example # | Structure of the Free Base | Mass |
|---|---|---|
| 86 | 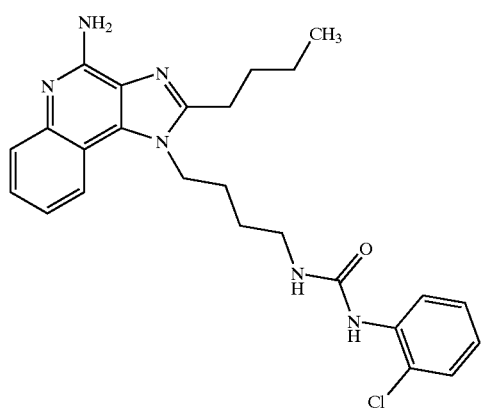 | 465.2 |
| 87 | 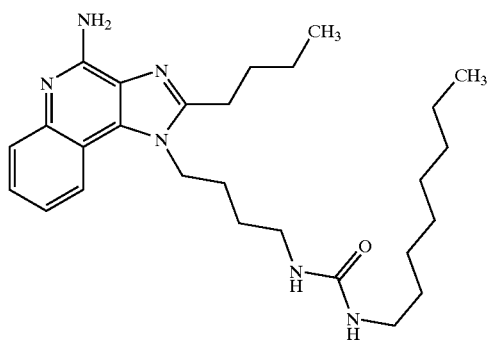 | 467.3 |
| 88 | 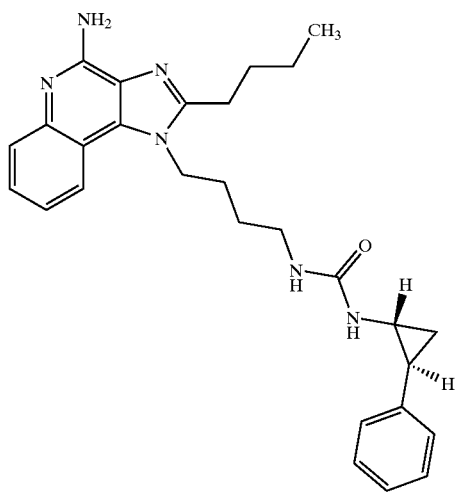 | 471.3 |

| Example # | Structure of the Free Base | Mass |
|---|---|---|
| 89 | 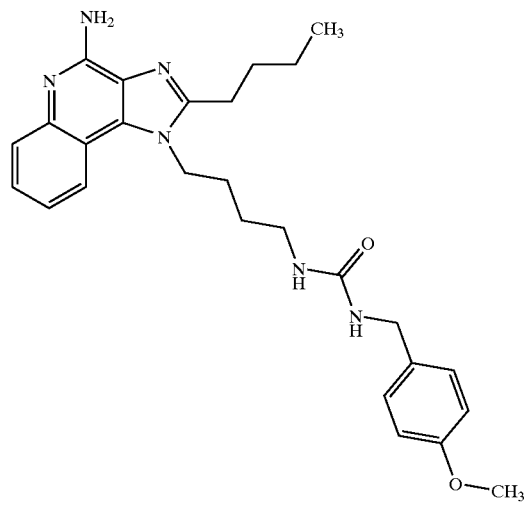 | 475.3 |
| 90 | 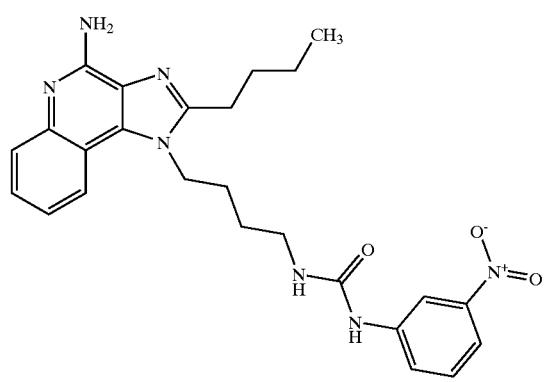 | 476.2 |
| 91 | 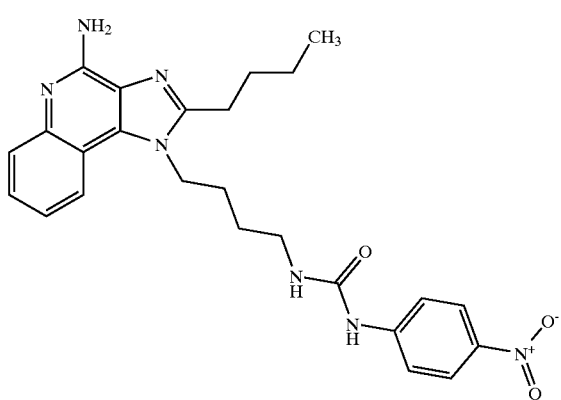 | 476.2 |

| Example # | Structure of the Free Base | Mass |
|---|---|---|
| 92 | 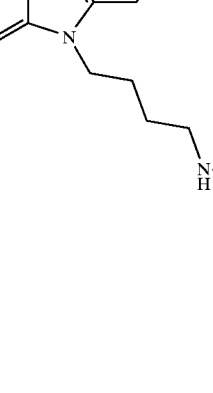 | 479.2 |
| 93 | 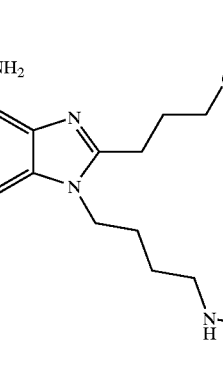 | 499.2 |
| 94 | 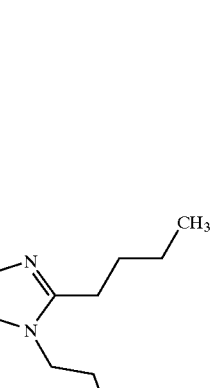 | 499.2 |

-continued
| Example # | Structure of the Free Base | Mass |
|---|---|---|
| 95 | 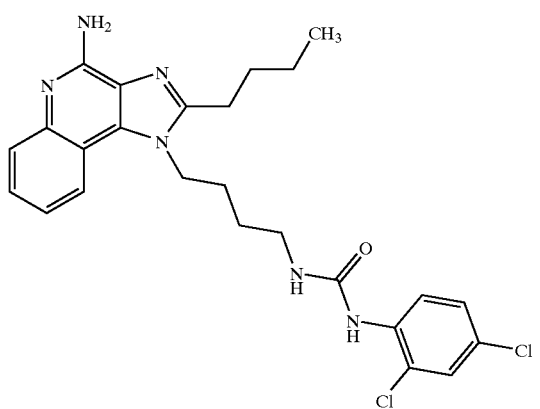 | 499.2, 501.1 |
| 96 | 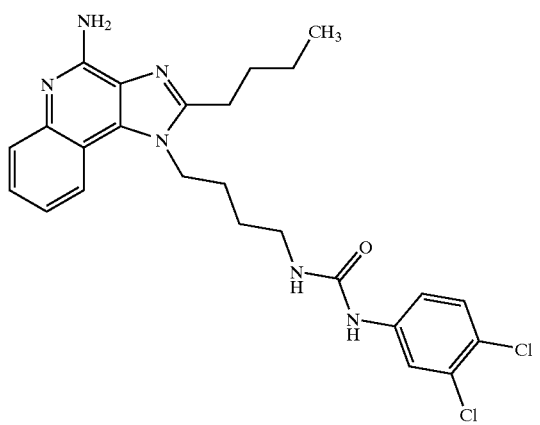 | 499.2, 501.1 |
| 97 | 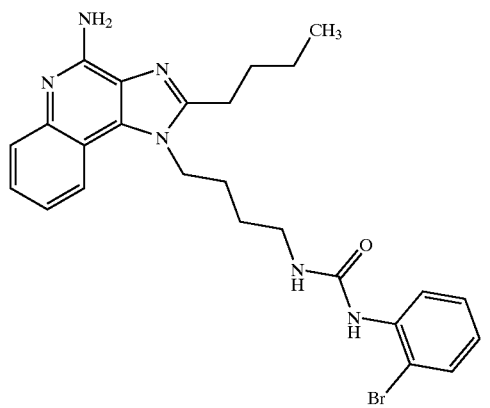 | 509, 511.1 |

-continued

| Example # | Structure of the Free Base | Mass |
|---|---|---|
| 98 | *[imidazoquinoline with 2-butyl, 1-(4-(3-(3-bromophenyl)ureido)butyl), 4-amino substituents]* | 509, 511.1 |
| 99 | *[imidazoquinoline with 2-butyl, 1-(4-(3-(4-bromophenyl)ureido)butyl), 4-amino substituents]* | 509, 511.1 |

EXAMPLES 100–119

The examples in the table below were prepare according to the synthetic method of Reaction Scheme II above by reacting 1-(4aminobutyl)-2-(2-methoxyethyl)-1H-imidazo[4,5-c]quinolin-4-amine with the appropriate isocyanate using the general method of Examples 53–66 above.

| Example # | Structure of the Free Base | Mass |
|---|---|---|
| 100 | *[imidazoquinoline with 2-(2-methoxyethyl), 1-(4-(3-(adamantyl)ureido)butyl), 4-amino substituents]* | 491.3 |

-continued

| Example # | Structure of the Free Base | Mass |
|---|---|---|
| 101 | | 385.2 |
| 102 | | 399.2 |
| 103 | | 413.2 |
| 104 | | 433.2 |

-continued
| Example # | Structure of the Free Base | Mass |
|---|---|---|
| 105 | 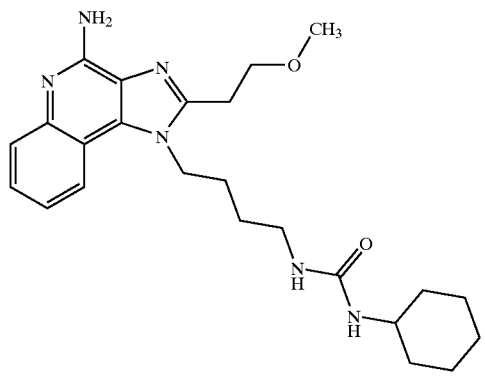 | 439.2 |
| 106 | 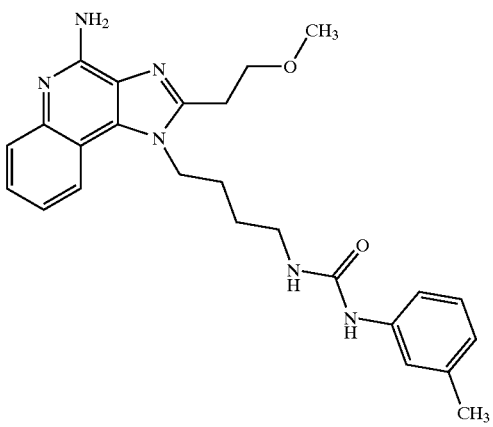 | 447.2 |
| 107 | 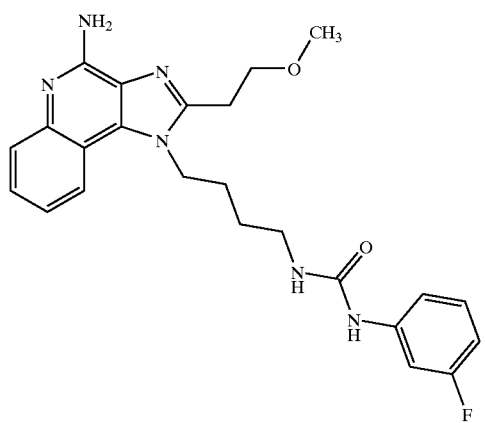 | 451.1 |

-continued

| Example # | Structure of the Free Base | Mass |
|---|---|---|
| 108 | 4-amino-2-(2-methoxyethyl)-1-[4-[3-(3-cyanophenyl)ureido]butyl]-1H-imidazo[4,5-c]quinoline | 458.2 |
| 109 | 4-amino-2-(2-methoxyethyl)-1-[4-[3-(4-cyanophenyl)ureido]butyl]-1H-imidazo[4,5-c]quinoline | 458.2 |
| 110 | 4-amino-2-(2-methoxyethyl)-1-[4-[3-((R)-1-phenylethyl)ureido]butyl]-1H-imidazo[4,5-c]quinoline | 461.2 |

-continued
| Example # | Structure of the Free Base | Mass |
|---|---|---|
| 111 | 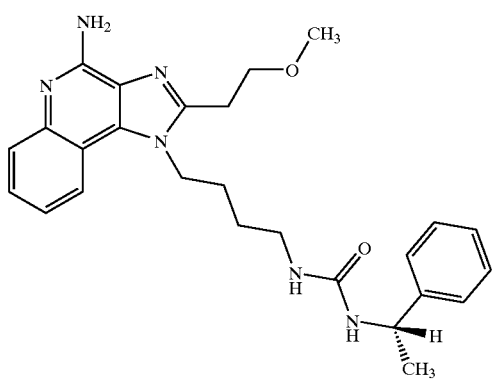 | 461.2 |
| 112 | 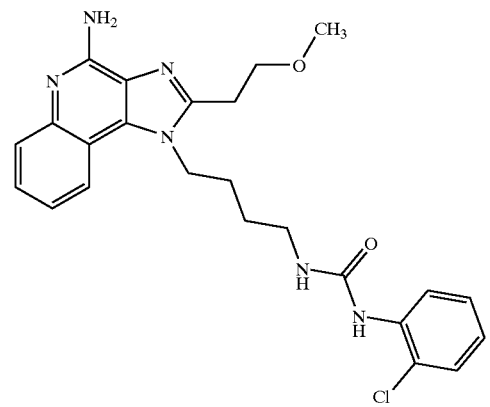 | 467.1 |
| 113 | 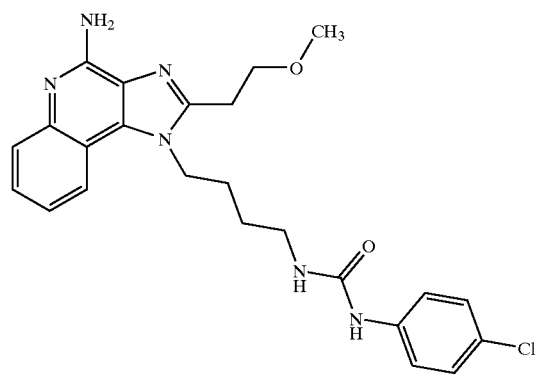 | 467.1 |

-continued
| Example # | Structure of the Free Base | Mass |
|---|---|---|
| 114 | 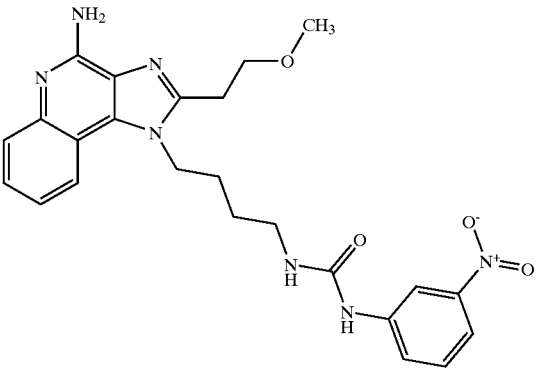 | 478.1 |
| 115 | 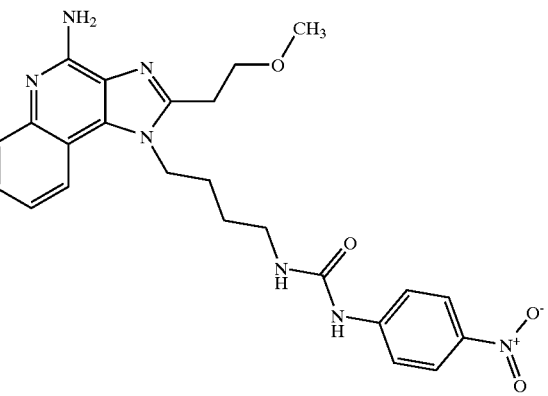 | 478.1 |
| 116 | 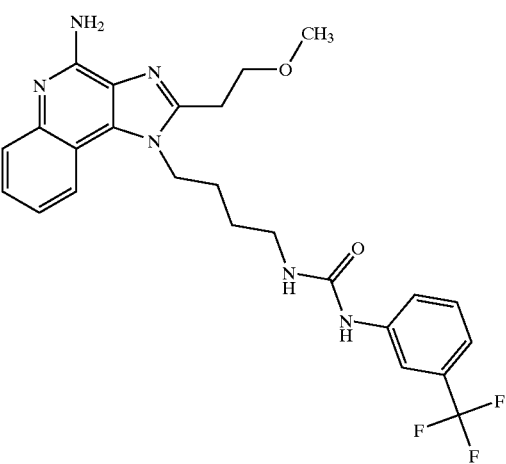 | 501.2 |

-continued

| Example # | Structure of the Free Base | Mass |
|---|---|---|
| 117 | | 501.2 |
| 118 | | 501.0, 503.1 |
| 119 | | 511, 513.1 |

EXAMPLES 120–122

The examples in the table below were prepared according to the synthetic method of Reaction Scheme III above using the following method. 1-(4-Aminobutyl)-2-(2-methoxyethyl)-1H-imidazo[4,5-c]quinolin-4-amine (50 mg), diisopropylethylamine (34 μL), dichloromethane (2 mL) and the carbamyl chloride (1.1 eq) were placed in a 2 dram (7.4 mL) vial. The vial was placed on a shaker for about 2 hours at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 m5min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired urea.

| Example # | Structure of the Free Base | Mass |
|---|---|---|
| 120 | | 447.3 |
| 121 | | 427.2 |
| 122 | | 411.3 |

EXAMPLES 123–124

The examples in the table below were prepare according to the synthetic method of Reaction Scheme II above by reacting 1-(4-aminobutyl)-2-(4-methoxyphenylmethyl)-1H-imidazo[4,5-c]quinolin-4-amine with the appropriate isocyanate using the general method of Examples 53–66 above.

| Example # | Structure of the Free Base | Mass |
|---|---|---|
| 123 | | 461.3 |
| 124 | | 495.3 |

EXAMPLES 125–131

The examples in the table below were prepared according to the synthetic method of Reaction Scheme II above using the following method. 1-(4Aminobutyl)-2-(2-methoxyethyl)-1H-imidazo[4,5-c]quinolin4-amine (50 mg), dichloromethane (2 mL) and the thioisocyanate (1.1 eq) were placed in a 2 dram (7.4 mL) vial. The vial was placed on a sonicator for about 30–60 minutes at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired thiourea.

| Example # | Structure of the Free Base | Mass |
|---|---|---|
| 125 | | 450.1 |
| 126 | | 542.2 |
| 127 | | 415.1 |
| 128 | | 449.1 |

-continued

| Example # | Structure of the Free Base | Mass |
|---|---|---|
| 129 | | 413.1 |
| 130 | | 429.2 |
| 131 | | 499.2 |

EXAMPLES 132–137

The examples in the table below were prepared according to the synthetic route shown in Reaction Scheme VII above.

Part A

The tetrahydroquinoline amine starting materials were prepared as follows.

A catalytic amount of platinum (IV) oxide was added to a solution of 1-(4-aminobutyl)-2-butyl-1H-imidazo[4,5-c]quinolin-4-amine (2.2 g, 7.06 mmol) in trifluoroacetic acid (200 mL). The reaction mixture was hydrogenated at 50 psi (3.44×10⁵ Pa) on a Parr apparatus for 6 days The reaction mixture was filtered to remove the catalyst and the filtrate was concentrated under vacuum. The residue was combined with 1 N hydrochloric acid (100 mL) and heated on a steam bath for 2 hours. The mixture was cooled, made basic with ammonium hydroxide and then extracted with dichloromethane. The extract was concentrated under vacuum to provide of 1-(4-aminobutyl)-2-butyl-6,7,8,9-tetrahydro-1H-imidazo[4,5-c]quinolin4-amine as a solid, m.p. 63–67° C.

A catalytic amount of platinum (IV) oxide was added to a solution of 1-(4-aminobutyl-2-methoxyethyl-1H-amino-[4,5-c]quinolin-4-amine (7.7 g, 24.5 mmol) in trifluoroacetic acid (250 mL). The reaction mixture was hydrogenated at 50 psi (3.44×10⁵ Pa) on a Parr apparatus. The progress of the reaction was monitored by LC/MS. Additional catalyst was added 7, 11, and 17 days after the start of the reaction. After 25 days the reaction was complete. The reaction mixture was filtered through a layer of Celite® filter aid to remove the catalyst and the filtrate was concentrated under vacuum. The residue was combined with 1 N hydrochloric acid (100 mL) and stirred overnight. The mixture was made basic (pH =11) with ammonium hydroxide and then extracted with dichloromethane (3×300 mL). The extracts were combined and concentrated under vacuum to provide 3.5 g of 1-(4-aminobutyl)-6,7,8,9-tetrahydro2-methoxyethyl-1H-imidazo[4,5-c]quinolin-4-amine as a solid.

Part B

The tetrahydroimidazoquinoline amines from Part A were reacted with the appropriate isocyanate or sulfonyl isocyanate using the general method of Examples 53–66 above to provide the trifluoroacetate salt of the desired urea or sulfonyl urea.

| Example # | Structure of the Free Base | Mass |
|---|---|---|
| 132 | | 493.20 |
| 133 | | 449.2 |
| 134 | | 389.2 |

-continued

| Example # | Structure of the Free Base | Mass |
|---|---|---|
| 135 | 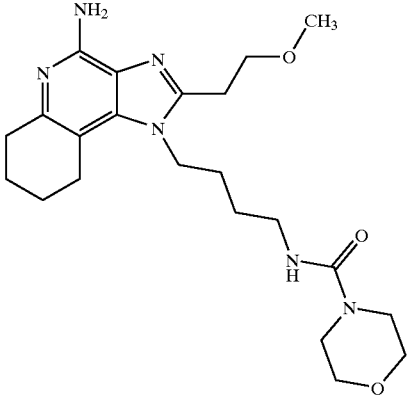 | 431.2 |
| 136 | 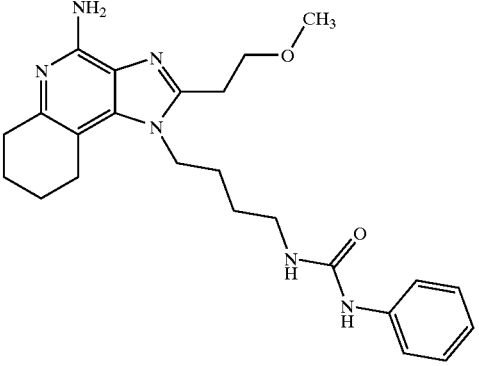 | 437.2 |
| 137 | 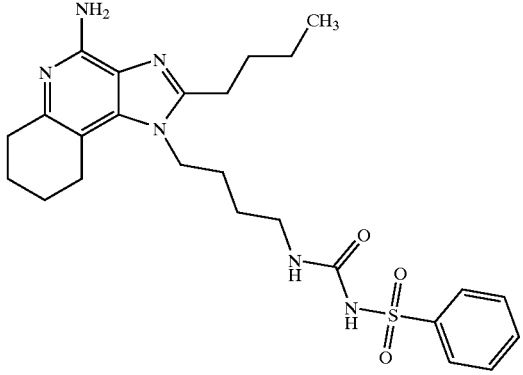 | 499.1 |

EXAMPLES 138–140

The examples in the table below were prepared according to the synthetic method of Reaction Scheme VI above using the following procedure. The 1H-imidazo[4,5-c]quinolin-4-amine (50 mg), dichloromethane (2 mL) and the sulfonyl-isocyanate (1.3 eq) were placed in a 2 dram (7.4 mL) vial. The vial was placed on a shaker at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonylurea.

| Example # | Structure of the Free Base | Mass |
|---|---|---|
| 138 | | 495.2 |
| 139 | | 485.0 |
| 140 | | 501.0, 503.0 |

EXAMPLE 141

$N^1$-{4-[4-Amino-2-(2-methoxyethyl)-1H-imidazo[4,5-c]quinolin-1-yl]butyl}-$N^3$-benzoylurea Trifluoroacetate

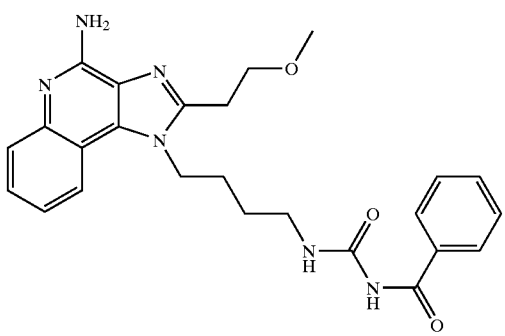

$N^1$-{4-[4-Amino-2-(2-methoxyethyl)-1H-imidazo[4,5-c]quinolin-1-yl]butyl}-$N^3$-benzoylurea Trifluoroacetate This compound was prepared according to the synthetic method of Reaction Scheme V above. The 1-(4-aminobutyl)-2-(2-methoxyethyl)-1H-imidazo[4,5-c]quinolin-4-amine (50 mg), dichloromethane (2 mL) and benzoylisocyanate (1.1 eq) were placed in a 2 dram (7.4 mL) vial. The vial was placed on a shaker for 2 hours at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 L/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired compound. MS (APCI) m/e 461.2 (M+H).

EXAMPLE 142

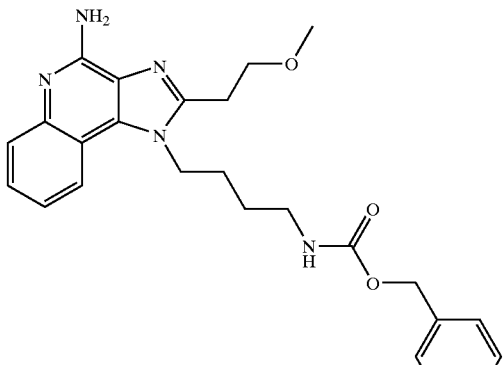

N-{4-[4-Amino-2-(2-methoxyethyl)-1H-imidazo[4,5-c]quinolin-1-yl]butyl}
carbamate Trifluoroacetate This compound was prepared according to the synthetic method of Reaction Scheme IV above. The 1-(4-aminobutyl)-2-(2-methoxyethyl)-1H-imidazo[4,5-c]quinolin-4amine (50 mg), diisopropylethylamine (1.2 eq.), dichloromethane (2 mL) and benzyl chloroformate (1.1 eq) were placed in a 2 dram (7.4 mL) vial. The vial was placed on a shaker for 2 hours at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired compound. MS (APCI) m/e 448.2 (M+H).

EXAMPLE 143

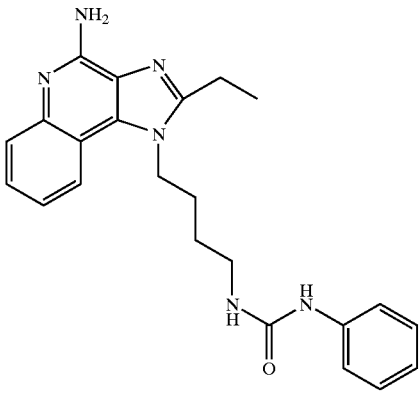

N-[4-(4-amino-2-ethyl-1H-imidazo[4,5-c]quinolin-1-yl)butyl]-N'-
phenylurea

Triethylamine (0.59.mL, 4.3 mmol) was added to a solution of 1-(4-aminobutyl)-2-ethyl-1H-imidazo[4,5-c]quinolin-4-amine (1.00 g, 3.5 mmol) in chloroform (100 mL). The solution was stirred in an ice bath for 5 min. Phenyl isocyanate (0.38 mL, 3.5 mmol) was slowly added. The resulting precipitate was isolated by filtration, washed with chloroform (4×30 mL), and then dried in an Abderhalden drying apparatus overnight to provide 1.11 g of N-[4-(4-amino-2-ethyl-1H-imidazo[4,5-c]quinolin-1-yl) butyl]-N'-phenylurea as a white solid, m.p. 179.7–181.4° C. Analysis: Calculated for $C_{23}H_{26}N_6O$.. 0.6 $H_2O$: %C, 66.84; %H, 6.63; %N, 20.33; Found: %C, 67.20; %H, 6.61; %N, 20.46.

EXAMPLE 144

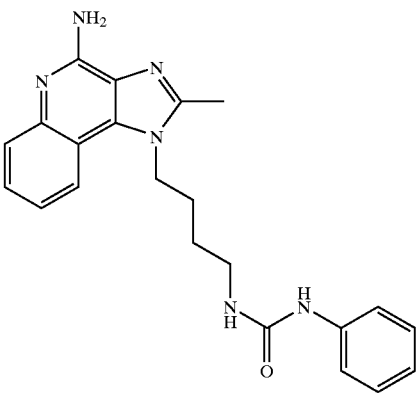

N-[4-(4-amino-2-methyl-1H-imidazo[4,5-c]quinolin-1-yl)butyl]-N'-
phenylurea

Using the general method of Example 143, 1-(4-aminobutyl)-2-methyl-1H-imidazo[4,5-c]quinolin-4-amine (500 mg, 1.9 mmol) was reacted with phenyl isocyanate to provide 123 mg of N-[4-(4-amino-2-methyl-1H-imidazo[4,5-c]quinolin-1-yl)butyl]-N'-phenylurea as a light brown solid, m.p. 171.5–172.5° C. Analysis: Calculated for $C_{22}H_{24}N_6O$. 0.60$H_2O$: %C 66.18; %H, 6.36; %N, 21.05; Found: %C, 66.05; %H, 6.43; %N, 20.61.

EXAMPLE 145

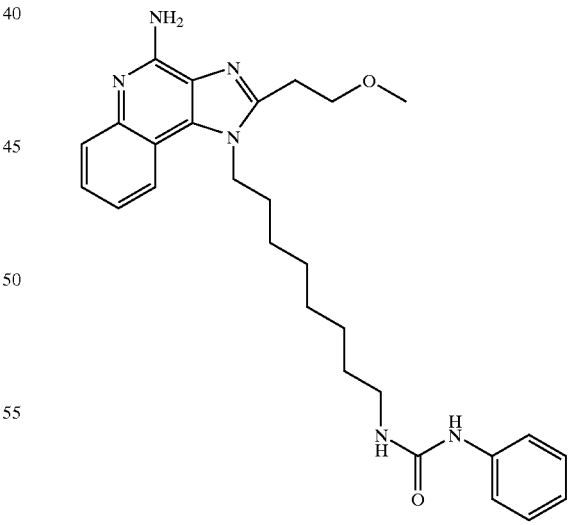

N-{8-[4-amino-2-(2-methoxyethyl)-1H-imidazo[4,5-c]quinolin-1-yl]octyl}-
N'-phenylurea Under a nitrogen atmosphere a mixture of 1-(8-aminooctyl)-2-(2-methoxyethyl)-1H-imidazo[4,5-c]quinolin-4-amine (1.5 g, 4.06 mmol) and dichloromethane (50 mL) was cooled to 0° C. Phenyl isocyanate was added dropwise. The reaction mixture was allowed to slowly warm to ambient temperature overnight. The reaction mixture was concentrated under reduced pressure. The crude product was purified by column chromatography (110 g silica gel eluting with 9:1 dichloromethane:methanol). The resulting orange solid was triturated with hexanes, isolated by filtration and then dried. This material was recrystallized from propyl acetate with a small amount of methanol, isolated by filtration, washed with hexanes, and then dried in a vacuum oven at 60° C. for 2 days to provide 0.6 g of N-{8-[4-amino-2-(2-methoxyethyl)-1H-imidazo[4,5-c]quinolin-1-yl]octyl}-N'-phenylurea as an off white powder, m.p. 136–142° C. Analysis: Calculated for $C_{28}H_{36}N_6O_2$: %C, 68.83; %H, 7.43; %N, 17.20; Found: %C, 68.27; %H, 7.44; %N, 16.85.

$^1$H NMR (300 MHz, DMSO-$d_6$) δ 8.36 (s, 1H), 8.01 (d, J=7.8 Hz, 1H), 7.61 (dd, J=8.3, 1.0 Hz, 1H), 7.44–7.35 (m, 3H), 7.29–7.17 (m, 3H), 6.87 (t, J=7.3 Hz, 1H), 6.52 (s, 2H), 6.08 (m, 1H), 4.51 (t, J=7.8 Hz, 2H), 3.82 (m, 2H), 3.29 (s, 3H), 3.18 (t, J=6.4 Hz, 2H), 3.05 (mn, 2H), 1.81 (m, 2H), 1.42–1.29((m, 10H);

$^{13}$C NMR (75 MHz, DMSO-$d_6$) δ 155.5, 152.0, 151.0, 145.0, 141.0, 132.6, 128.9, 126.8, 126.7, 126.6, 121.5, 121.2, 120.7, 117.9, 115.1, 70.5,58.5, 45.3, 30.1, 29.0, 27.5, 26.6, 26.2.

MS m/z489(M+H).

EXAMPLE 146

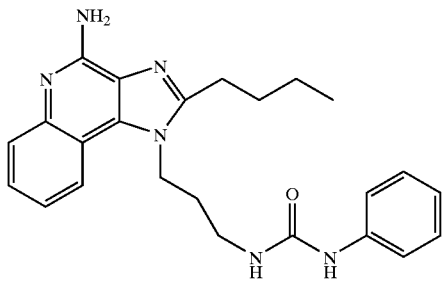

N-[3-(4-amino-2-butyl-1H-imidazo[4,5-c]quinolin-1-yl)propyl]-N'-phenylurea

Part A

Tert-butyl 3-(2-butyl-1H-imidazo[4,5-c]quinolin-1-yl)propylcarbamate (~80 g) was dissolved in 1,4-dioxane (400 mL) with gentle heating. Hydrochloric acid (55 mL of 4.0 M in 1,4-dioxane) was added in a single portion and the reaction was heated to reflux. The reaction was monitored by HPLC. Additional acid (150–200 mL) was added and the reaction mixture was refluxed until the reaction was complete. The reaction mixture was cooled to ambient temperature. A solid was isolated by filtration to give ~72 g of 3-(2-butyl-1H-imidazo[4,5-c]quinolin-1-yl)propylamine hydrochloride. This material was combined with that from a previous experiment and then dissolved in water (400 mL). The solution was neutralized with solid potassium carbonate. At pH 7 a solid precipitated. The solid was isolated by filtration and then dissolved in water (1500 mL). The pH was adjusted to pH 10 with solid potassium carbonate. The solution was extracted with chloroform until HPLC analysis showed that no amine remained in the aqueous layer. The organic layers were combined and then concentrated under reduced pressure to provide 45 g of 3-(2-butyl-1H-imidazo[4,5-c]quinolin-1-yl)propylamine.

Part B

A solution of phenyl isocyanate (1.00 g, 7.79 mmol) in dichloromethane (10 mL) was added dropwise over 5 minutes with stirring to a solution of 3-(2-butyl-1H-imidazo[4,5-c]quinolin-1-yl)propylamine (2.00 g, 7.08 mmol) in dichloromethane (50 mL). The resulting precipitate was isolated by filtration to provide 2.50 g of N-[3-(2-butyl-1H-imidazo[4,5-c]quinolin-1-yl)propyl]-N'-phenylurea.

Part C

3-Chloroperoxybenzoic acid (1.72 g of ~60%) was added in small portions over a period of 15 minutes to a suspension of the material from Part B in chloroform (75 mL). A solution was obtained during the addition. The reaction mixture was allowed to stir overnight and then it was filtered to provide 1.2 g of N-[3-(2-butyl-5-oxido-1H-imidazo[4,5-c]quinolin-1-yl)propyl]-N'-phenylurea as a light blue solid. The filtrate was combined with 1% aqueous sodium bicarbonate (100 mL). The layers were separated. The aqueous layer was extracted with chloroform (3×70 mL) and then filtered to provide 1.05 g of N-[3-(2-butyl-5-oxido-1H-imidazo[4,5-c]quinolin-1-yl)propyl]-N'-phenylurea as an off white solid.

Part D

Concentrated ammonium hydroxide (35 mL) was added with stirring to a solution of N-[3-(2-butyl-5-oxido-1H-imidazo[4,5-c]quinolin-1-yl)propyl]-N'-phenylurea (2.25 g, 5.39 mmol) in dichloromethane (100 mL). Tosyl chloride (1.13 g,5.93 mmol) was added in small portions over a period of 30 minutes. After 1 hour the layers were separated. The aqueous layer was extracted with dichloromethane (2×25 mL). The organics were combined and extracted with water (3×50 mL). The aqueous layers were combined and filtered to provide 1.64 g of an off white solid. This material was recrystallized sequentially from 1,2-dichloroethane, isopropyl alcohol and methanol to provide 960 mg of N-[3-(4-amino-2-butyl-1H-imidazo[4,5-c]quinolin-1-yl)propyl]-N'-phenylurea as light tan needles, m.p. 191–192° C. Analysis: Calculated for $C_{24}H_{28}N_6O$: %C, 69.21; %H, 6.78; %N, 20.18; Found: %C; 68.94; %H, 6.77; %N, 19.90.

EXAMPLE 147

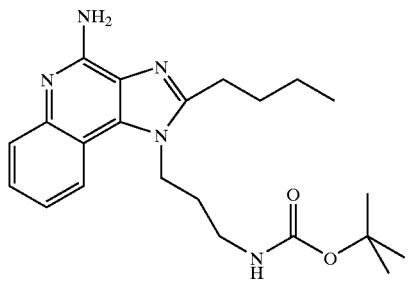

tert-butyl 3-(4-amino-2-butyl-1H-imidazo[4,5-c]quinolin-1-yl)propylcarbamate

Part A

Using the general method of Example 146 Part C, tert-butyl 3-(2-butyl-1H-imidazo[4,5-c]quinolin-1-yl)propylcarbamate (27.0 g) was oxidized to provide 39 g of tert-butyl 3-(2-butyl-5-oxido-1H-imidazo[4,5-c]quinolin-1-yl)propylcarbamate as a light gray solid.

Part B

Using the general method of Example 146 Part D, tert-butyl 3-(2-butyl-5-oxido-1H-imidazo[4,5-c]quinolin-1-yl)propylcarbamate (28.13 g) was aminated to provide 26.75 g of crude product. A small portion was recrystallized from toluene and then further purified by column chromatography (silica gel eluting with 5% methanol in dichloromethane). The purified material was recrystallized from acetonitrile to provide 0.15 g of tert-butyl 3-(4-amino-2-butyl-1H-imidazo[4,5-c]quinolin-1-yl)propylcarbamate as white solid, m.p. 192.7–193.4° C. Analysis: Calculated for $C_{22}H_{31}N_5O_2$: %C, 66.47; %H, 7.86; %N, 17.62; Found: %C, 66.49; %H, 7.94; %N, 17.76.

EXAMPLE 148

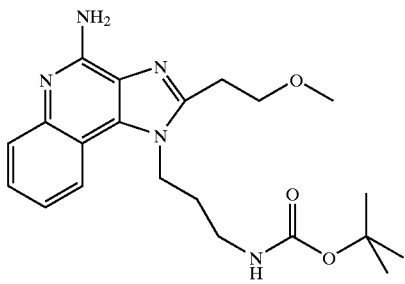

tert-butyl 3-[4-amino-2-(2-methoxyethyl)-1H-imidazo[4,5-c]quinolin-1-yl]propylcarbamate Part A Using the general method of Example 146 Part C, tert-butyl 3-[2-(2-methoxyethyl)-1H-imidazo[4,5-c]quinolin-1-yl]propylcarbamate (~80 g) was oxidized to provide tert-butyl 3-[2-(2-methoxyethyl)-5-oxido-1H-imidazo[4,5-c]quinolin-1-yl]propylcarbamate.

Part B

Using the general method of Example 146 Part D, the material from Part A was aminated to provide crude product. A small portion was recrystallized from acetonitrile to provide 1.27 g of tert-butyl 3-[4-amino-2-(2-methoxyethyl)-1H-imidazo[4,5-c]quinolin-1-yl]propylcarbamate as a solid, m.p. 174.2–175.8° C. Analysis: Calculated for $C_{21}H_{29}N_5O_3$: %C, 63.14; %H, 7.32; %N, 17.53; Found: %C, 62.89; %H, 7.23; %N, 17.42.

EXAMPLE 149

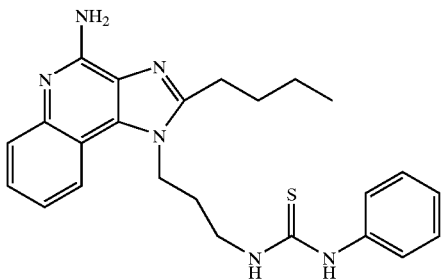

N-[3-(4-amino-2-butyl-1H-imidazo[4,5-c]quinolin-1-yl)propyl]-N'-phenylthiourea

Phenyl isothiocyanate (750 mg, 5.55 mmol) was added dropwise with stirring to a chilled (0° C.) solution of 1-(3-aminopropyl)-2-butyl-1H-imidazo[4,5-c]quinolin-4-amine (1.0 g, 3.36 mmol) in 1-methyl-2-pyrrolidinone (50 mL). The reaction mixture was poured into water (500 mL) and the pH adjusted to 10 with solid potassium carbonate. The resulting precipitate was isolated by filtration and then rinsed with water. This material was slurried with hot methanol and then purified by column chromatography (silica gel eluting with 2% methanol in dichloromethane to 7% methanol in dichloromethane). The purified material was recrystallized from isopropanol to provide 950 mg of N-[3-(4-amino-2-butyl-1H-imidazo[4,5-c]quinolin-1-yl)propyl]-N'-phenylthiourea as a white solid, m.p. 142.8–144.0° C. Analysis: Calculated for $C_{24}H_{28}N_6S \cdot C_3H_8O$: %C, 65.82; %H, 7.37; %N, 17.06; Found: %C, 65.77; %H, 7.41; %N, 17.11.

EXAMPLE 150

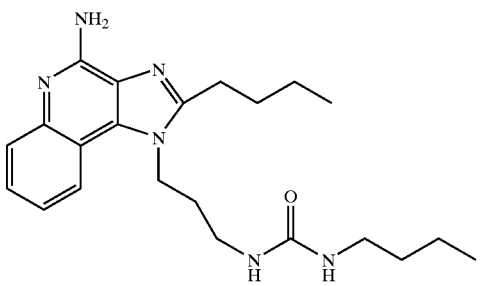

N-[3-(4-amino-2-butyl-1H-imidazo[4,5-c]quinolin-1-yl)propyl]-N'-butylurea

Triethylamine (765 mg, 7.56 mmol) was added to a solution of 1-(3-aminopropyl)-2-butyl-1H-imidazo[4,5-c]quinolin-4-amine (1.5 g, 5.04 mmol) in 1-methyl-2-pyrrolidinone (100 mL). Butyl isocyanate (549 mg, 5.55 mmol) was added dropwise with stirring. The reaction mixture was allowed to stir overnight and then it was poured into water (500 mL). The pH was adjusted to 10 using solid potassium carbonate. The resulting precipitate was isolated by filtration, washed with water and then purified by column chromatography (silica gel eluting with 5% methanol in dichloromethane and then with 10% methanol in dichloromethane. The purified material was recrystallized from acetonitrile to provide 800 mg of N-[3-(4-amino-2-butyl-1H-imidazo[4,5-c]quinolin-1-yl)propyl]-N'-butylurea as a white solid, m.p. 185.5–186.40C. Analysis: Calculated for $C_{22}H_{32}N_6O$: %C, 66.64; %H, 8.13; %N, 21.29; Found: %C, 66.38; %H, 8.19; %N, 21.10.

EXAMPLE 151

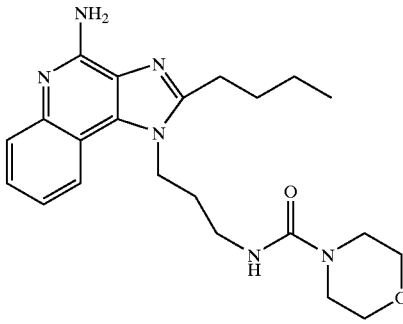

N-[3-(4-amino-2-butyl-1H-imidazo[4,5-c]quinolin-1-yl)propyl]morpholine-4-carboxamide Using the general method of Example 149, 1-(3-aminopropyl)-2-butyl-1H-imidazo[4,5-c]quinolin-4-amine (1.0 g. 3.36 mmol) was reacted with 4-morpholinecarbonyl chloride (830 mg, 5.55 mmol) to provide 650 mg of N-[3-(4-amino-2-butyl-1H-imidazo[4,5-c]quinolin-1-yl)propyl]

morpholine-4-carboxamide as a white powder, m.p. 193.4–194.6° C. Analysis: Calculated for $C_{22}H_{30}N_6O_2$: %C, 64.37; %H, 7.37; %N, 20.47; Found: %C, 64.00; %H, 7.32; %N, 20.16.

EXAMPLE 152

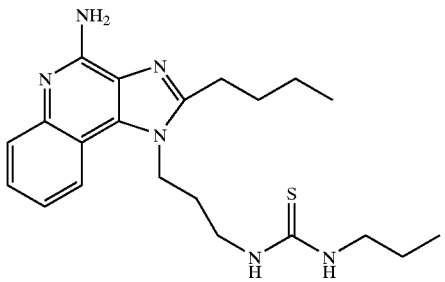

N-[3-(4-amino-2-butyl-1H-imidazo[4,5-c]quinolin-1-yl)propyl]-N'-propylthiourea

Using the general method of Example 150, 1-(3-aminopropyl)-2-butyl-1H-imidazo[4,5-c]quinolin-4-amine (1.5 g, 5.04 mmol) was reacted with propyl isothiocyanate (560 mg, 5.55 mmol) to provide 1.34 g of N-[3-(4-amino-2-butyl-1H-imidazo[4,5-c]quinolin-1-yl)propyl]-N'-propylthiourea as a crystalline solid, m.p. 144.5–145.5° C. Analysis: Calculated for $C_{21}H_{30}N_6S$. $0.56H_2O$: %C, 61.72; %H, 7.68; %N, 20.56; Found: %C, 61.72; %H, 7.67; %N, 20.56.

EXAMPLE 153

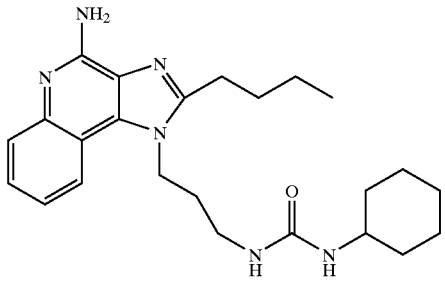

N-[3-(4-amino-2-butyl-1H-imidazo[4,5-c]quinolin-1-yl)propyl]-N'-cyclohexylurea

Part A

Using the general method of Example 146 Part B, 3-(2-butyl-1H-imidazo[4,5-c]quinolin-1-yl)propylamine (2.00 g, 7.08 mmol) was reacted with cyclohexyl isocyanate (1.0 g, 7.98 mmol) to provide 2.62 g of N-[3-(2-butyl-1H-imidazo[4,5-c]quinolin-1-yl)propyl]-N'-cyclohexylurea.

Part B

Using the general method of Example 146 Part C, the material from Part A was oxidized to provide 2.37 g of N-[3-(2-butyl-5-oxido-1H-imidazo[4,5-c]quinolin-1-yl)propyl]-N'-cyclohexylurea as an off white solid.

Part C

Using the general method of Example 146 Part D, the material from Part B was aminated to provide 380 mg of N-[3-(4-amino-2-butyl-1H-imidazo[4,5-c]quinolin-1-yl)propyl]-N'-cyclohexylurea as a white powder, m.p. 200–201° C. Analysis: Calculated for $C_{24}H_{34}N_6O$. $1.19H_2O$: %C, 64.92; %H, 8.26; %N, 18.93; Found: %C, 65.09; %H, 8.39; %N, 18.85.

EXAMPLE 154

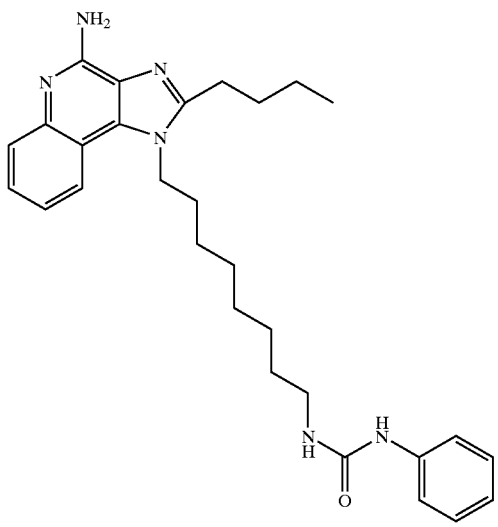

N-[8-(4-amino-2-butyl-1H-imidazo[4,5-c]quinolin-1-yl)octyl]-N'-phenylurea

Using the general method of Example 145, 1-(8-aminooctyl)2-butyl-1H-imidazo[4,5-c]quinolin-4amine (1.2 g, 3.26 mmol) was reacted with phenyl isocyanate to provide 1.59 g of N-[8-(4-amino-2-butyl-1H-imidazo[4,5-c]quinolin-1-yl)octyl]-N'-phenylurea as an off white powder, m.p. 153–155° C. Analysis: Calculated for $C_{29}H_{38}N_6O$. $0.20H_2O$: %C, 71.05; %H, 7.89; %N, 17.14; Found: %C, 70.86; %H, 7.97; %N, 16.87.

$^1H$ NMR (300 MHz, DMSO-$d_6$) δ 8.34 (s, 1H), 8.01 (d, J=7.8 Hz, 1H), 7.61 (dd, J=8.3, 1.0 Hz, 1H), 7.43–7.36 (m, 3H), 7.26–7.17 (m, 3H), 6.87 (t, J=7.3 Hz, 1H), 6.49 (s, 2H), 6.08 (m, 1H), 4.49 (m, 2H), 3.05 (m, 2H), 2.91 (m, 2H), 1.80 (m, 4H), 1.43–1.29 (m, 12 H), 0.95 (t, J=7.3 Hz, 3H);

$^{13}C$ NMR (125 MHz, DMSO-$d_6$) 155.5,153.4, 152.0, 144.9, 141.0, 132.6, 128.9, 126.7, 126.62, 126.57, 121.5, 121.2, 120.2, 117.9, 115.1, 45.1, 39.3,30.1, 30.0, 29.0, 28.9,26.6, 26.5,26.2,22.3, 14.1;

MS m/z 487 (M+1)

EXAMPLE 155

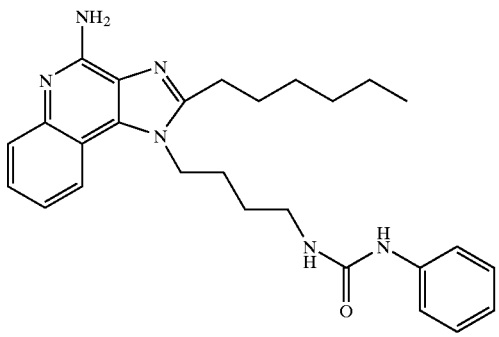

N-[4-(4-amino-2-hexyl-1H-imidazo[4,5-c]quinolin-1-yl)butyl]-N'-phenylurea

Part A

Using the general method of Example 146 Part A, tert-butyl 4(2-hexyl-1H-imidazo[4,5-c]quinolin-1-yl)

butylcarbamate (5.0 g, 11.8 mmol)was hydrolyzed to provide 1.27 g 4(2-hexyl-1H-imidazo[4,5-c]quinolin-1-yl)butylamine as an off-white crystalline solid, m.p. 171.0–172.4° C.

Part B

Using the general method of Example 146 Part B, 4(2-hexyl-1H-imidazo[4,5-c]quinolin-1-yl)butylamine (4.0 g, 12.3 mmol) was reacted with phenyl isocyanate (1.34 mL, 12.3 mmol) to provide 4.77 g of N-[4-(2-hexyl-1H-imidazo[4,5-c]quinolin-1-yl)butyl]-N'-phenylurea.

Part C

Using the general method of Example 146 Part C, the material from Part B was oxidized to provide N-[4-(2-hexyl-5-oxido-1H-imidazo[4,5-c]quinolin-1-yl)butyl]-N'-phenylurea.

Part D

Using the general method of Example 146 Part D, the material from Part C was aminated to provide 2.20 g of N-[4-(4-amino-2-hexyl-]H-imidazo[4,5-c]quinolin-1-yl)butyl]-N'-phenylurea as a light brown solid, m.p. 170.4–171.6° C. Analysis: Calculated for $C_{27}H_{34}N_6O \cdot 0.50H_2O$: %C, 69.35; %H, 7.54; %N, 17.97; Found: %C, 69.02; %H, 7.42; %N, 17.80.

EXAMPLE 156

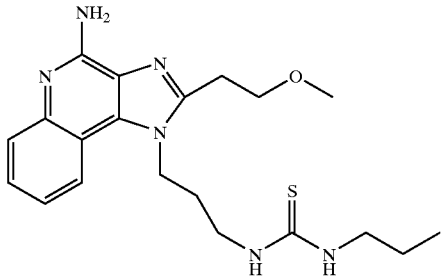

N-{3-[4-amino-2-(2-methoxyethyl)-1H-imidazo[4,5-c]quinolin-1-yl]propyl}-N'-propylthiourea Using the general method of Example 149, 1-(3-aminopropyl)-2-(2-methoxyethyl)-1H-imidazo[4,5-c]quinolin-4amine (1.53 g, 5.11 mmol) was reacted with propyl isothiocyanate (570 mg, 5.62 mmol) to provide 950 mg of N- {3-[4-amino-2-(2-methoxyethyl-1H-imidazo[4,5-c]quinolin-1-yl]propyl)-N'-propylthiourea as a tan powder, m.p. 172–173° C. Analysis: Calculated for $C_{20}H_{28}N_6OS$: %C, 59.97; %H, 7.05; %N, 20.98; Found: %C, 59.83; %H, 7.01; %N, 20.95.

EXAMPLE 157

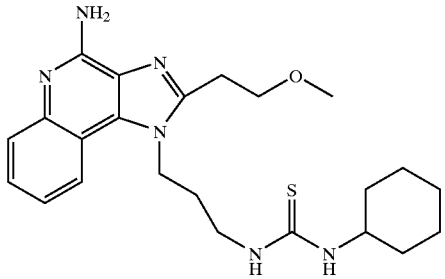

N-{3-[4-amino-2-(2-methoxyethyl)-1H-imidazo[4,5-c]quinolin-1-yl]propyl}-N'-cyclohexylthiourea Using the general method of Example 149, 1-(3-aminopropyl)-2-(2-methoxyethyl)-1H-imidazo[4,5-c]quinolin-4-amine (1.53 g, 5.11 mmol) was reacted with cyclohexyl isothiocyanate (794 mg, 5.62 mmol) to provide 1.35 g of N-(3-[4-amino-2-(2-methoxyethyl)-1H-imidazo[4,5-c]quinolin-1-yl]propyl 1-]-cyclohexylthiourea as a tan powder, m.p. 199–200° C. Analysis: Calculated for $C_{23}H_{32}N_6OS$: %C, 62.70; %H, 7.32; %N, 19.07; Found: %C, 62.37; %H, 7.20; %N, 18.70.

EXAMPLE 158

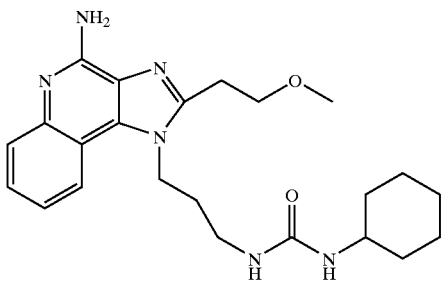

N-{3-(4-amino-2-(2-methoxyethyl)-1H-imidazo[4,5-c]quinolin-1-yl]propyl}-N'-cyclohexylurea Using the general method of Example 149, 1-(3-aminopropyl)-2-(2-methoxyethyl)-1H-imidazo[4,5-c]quinolin4-amine (1.50 g, 5.01 mmol) was reacted with cyclohexyl isocyanate (780 mg, 5.51 mmol) to provide 1.02 g of N-l3-[4amino-2-(2-methoxyethyl)-1H-imidazo[4,5-c]quinolin-1-yl]propyl)-N'-cyclohexylurea as a solid, m.p. 179–180° C. Analysis: Calculated for $C_{23}H_{32}N_6O_2 \cdot 0.75H_2O$: %C, 63.06; %H, 7.71; %N, 19.18; Found: %C, 62.74; %H, 7.57; %N, 19.16.

EXAMPLE 159

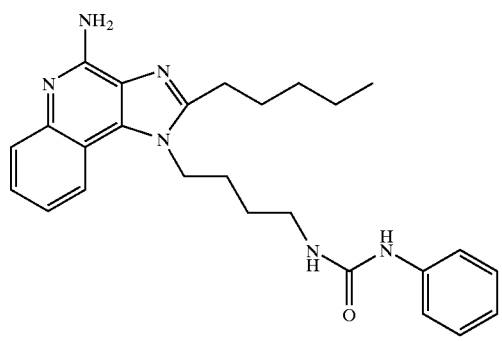

N-[4-(4-amino-2-pentyl-1H-imidazo[4,5-c]quinolin-1-yl)butyl]-N'-phenylurea

Using the general method of Example 149, 1-(4aminobutyl)-2-pentyl-1H-imidazo[4,5-c]quinolin-4-amine (800 mg, 2.5 mmol) was reacted with phenyl isocyanate (0.26 mL, 2.5 mmol) to provide 299 mg of N-[4-(4-amino-2-pentyl-1H-imidazo[4,5-c]quinolin-1-yl)butyl]-N'-phenylurea as an off white solid, m.p. 159.0–160.4° C. Analysis: Calculated for $C_{26}H_{32}N_6O_2 \cdot 1.0H_2O$: %C, 67.5 1; %H, 7.4 1; %N, 18.17; Found: %C, 67.73; %H, 7.33; %N, 17.97.

EXAMPLE 160

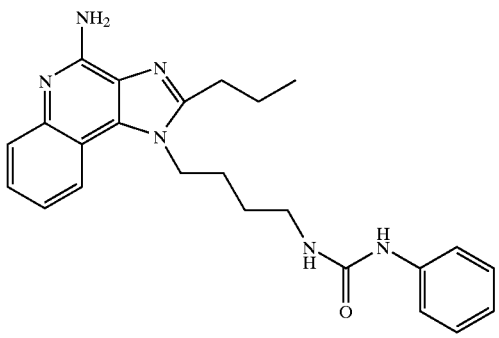

N-[4-(4-amino-2-propyl-1H-imidazo[4,5-c]quinolin-1-yl)butyl]-N'-phenylurea

Part A

Using the general method of Example 146 Part A, tert-butyl 4-(2-propyl-1H-imidazo[4,5-c]quinolin-1-yl)butylcarbamate was hydrolyzed to provide 4-(2-propyl-1H-imidazo[4,5-c]quinolin-1-yl)butan-1-amine.

Part B

Using the general method of Example 146 Part B, 4-(2-propyl-1H-imidazo[4,5-c]quinolin-1-yl)butan-1-amine (2.50 g, 8.9 mmol) was reacted with phenyl isocyanate (1.78 mL, 16.4 mmol) to provide 0.67 g of N-[4-(2-propyl-1H-imidazo[4,5-c]quinolin-1-yl)butyl]-N'-phenylurea as an off white solid.

Part C

Using the general method of Example 146 Part C, material from Part B was oxidized to provide 604 mg of N-[4-(5-oxido-2-propyl-1H-imidazo[4,5-c]quinolin-1-yl)butyl]-N'-phenylurea as a yellow residue.

Part D

Using the general method of Example 146 Part D, material from Part C was aminated to provide 473 mg of N-[4-(4-amino-2-propyl-1H-imidazo[4,5-c]quinolin-1-yl)butyl]-N'-phenylurea as an off white solid, m.p. 182.8–184.0° C. Analysis: Calculated for $C_{24}H_{28}N_6O \cdot 1.0H_2O$: %C, 66.34; %H, 6.96; %N, 19.34; Found: %C, 66.69; %H, 6.91; %N, 19.37.

EXAMPLE 161

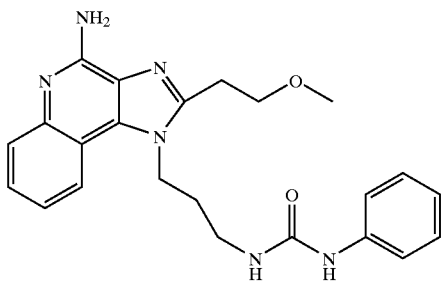

N-{3-[4-amino-2-(2-methoxyethyl)-1H-imidazo[4,5-c]quinolin-1-yl]propyl}-N'-phenylurea Using the general method of Example 149, 1-(3-aminopropyl)-2-(2-methoxyethyl)-1H-imidazo[4,5-c]quinolin-4-amine (1.50 g, 5.01 mmol) was reacted with phenyl isocyanate (660 mg, 5.51 mmol). Recrystallization from acetonitrile provided 670 mg of N-(3-[4-amino-2-(2-methoxyethyl)-1H-imidazo[4,5-c]quinolin-1-yl]propyl}-N'-phenylurea as light orange needles, m.p. ~40° C. Analysis: Calculated for $C_{23}H_{26}N_6O_2 \cdot 1.0\ C_2H_3N$: %C, 65.34; %H, 6.36; %N, 21.34; Found: %C, 65.13; %H, 6.26; %N, 21.35.

EXAMPLE 162

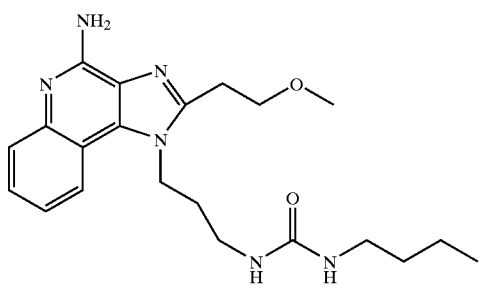

N-{3-[4-amino-2-(2-methoxyethyl)-1H-imidazo[4,5-c]quinolin-1-yl]propyl}-N'-butylurea Using the general method of Example 149, 1-(3-aminopropyl)-2-(2-methoxyethyl)-1H-imidazo[4,5-c]quinolin4-amine (1.50 g, 5.01 mmol) was reacted with butyl isocyanate to provide 1.13 g of N-(3-[4-amino-2-(2-methoxyethyl)-1H-imidazo[4,5-c]quinolin-1-yl]propyl)-N'-butylurea as an off-white powder, m.p. 159–160° C. Analysis: Calculated for $C_{21}H_{30}N_6O_2 \cdot 0.29H_2O$: %C, 62.47; %H, 7.63; %N, 20.82; Found: %C, 62.64; %H %N, 21.17.

EXAMPLE 163

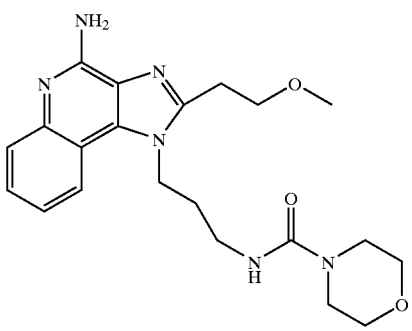

N-{3-[4-amino-2-(2-methozyethyl)-1H-imidazo[4,5-c]quinolin-1-yl]propyl}morpholine-4-carboxamide Using the general method of Example 143, 1-(3-aminopropyl)-2-(2-methoxyethyl)-1-imidazo[4,5-c]quinolin4-amine (1.50 g, 5.01 mmol) was reacted with 4-morpholinecarbonyl chloride (830 mg, 5.51 mmol) to provide 1.6 g of N-{3-[4-amino-2-(2-methoxyethyl)-1H-imidazo[4,5-c]quinolin-1-yl]propyl}morpholine-4-carboxamide as a white powder, m.p. 194–196° C. Analysis: Calculated for $C_{21}H_{28}N_6O_3$: %C, 61.15; %H, 6.84; %N, 20.37; Found: %C, 60.82; %H, 6.94; %N, 20.34.

EXAMPLE 164

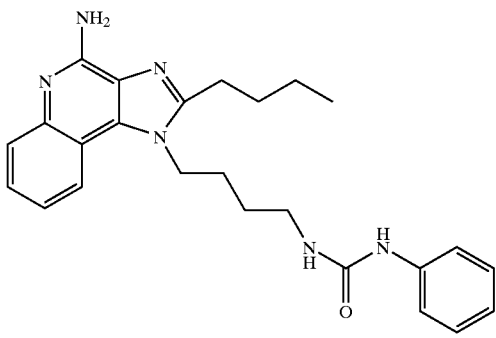

N-[4-(4-amino-2-butyl-1H-imidazo[4,5-c]quinolin-1-yl)butyl]-N'-phenylurea

Using the general method of Example 145, except that the reaction was run at ambient temperature, 1-(4-aminobutyl)-2-butyl-1H-imidazo[4,5-c]quinolin-4-amine (1.0 g, 3.2 mmol) was reacted with phenyl isocyanate (0.35 mL, 3.2 mmol) to provide 0.75 g of N-[4-(4-amino-2-butyl-1H-imidazo[4,5-c]quinolin-1-yl)butyl]-N'-phenylurea as white needles, m.p. 185–187° C. Analysis: Calculated for $C_{25}H_{30}N_6O \cdot H_2O$: %C, 66.94; %H, 7.19; %N, 18.74; Found: %C, 67.31; %H, 7.20; %N, 18.70.

EXAMPLE 165

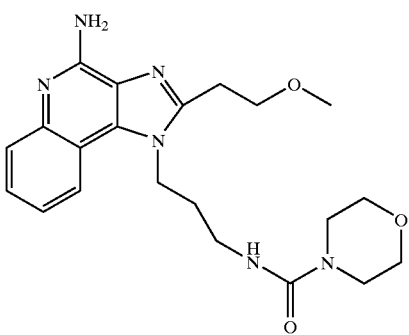

N-{3-[4-amino-2-(2-methoxyethyl)-1H-imidazo[4,5-c]quinolin-1-yl]propyl}morpholine-4-carboxamide Under a nitrogen atmosphere, triethylamine (1.04 mL, 7.51 mmol) was added to a chilled (0°) solution of 1-(3-aminopropyl)-2-(2-methoxyethyl)1H-imidazo[4,5-c]quinolin-4-amine (1.50 g, 5.01 mmol) in chloroform (75 mL). 4-Morpholinecarbonyl chloride (830 mg, 5.51 mmol) was added dropwise. The reaction was allowed to warm to ambient temperature and was maintained over the weekend. An equal volume of aqueous 1% sodium carbonate was added with vigorous stirring. A precipitate was isolated by filtration to provide 1.73 g of crude product as a white powder. This material was purified by column chromatography (silica gel eluting with a 0–5% methanol in chloroform gradient) and then triturated with diethyl ether to provide 1.6 g of N-{3-[4-amino-2-(2-methoxyethyl)-1H-imidazo[4,5-c]quinolin-1-yl]propyl}morpholine-4-carboxamide as a white powder, m.p. 194.0–196.0° C. Analysis: Calculated for $C_{21}H_{28}N_6O_3$: %C, 61.15; %H, 6.84; %N, 20.37; Found: %C, 60.82; %H, 6.94; %N, 20.34.

Example 166

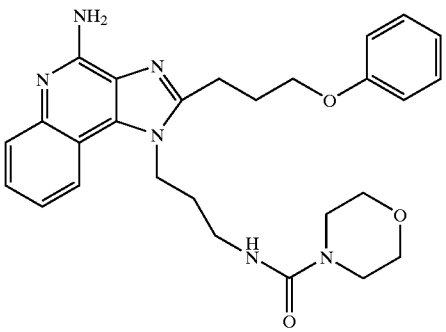

N-{3-[4-amino-2-(2-phenoxypropyl)-1H-imidazo[4,5-c]quinolin-1-yl]propyl}morpholine-4-carboxamide Using the general method of Example 150, 1-(3-aminopropyl)-2-(3-phenoxypropyl)-1H-imidazo[4,5-c]quinolin-4-amine (2.0 g, 5.32 mmol) was reacted with 4-morpholinecarbonyl chloride (880 mg, 5.86 mmol) to provide 1.8 g of N-{3-[4-amino-2-(3-phenoxypropyl)-1H-imidazo[4,5-c]quinolin-1-yl]propyl}morpholine-4-carboxamide as a light yellow crystalline solid, m.p. 198.8–199.9° C. Analysis: Calculated for $C_{27}H_{32}N_6O_3$ %C, 66.37; %H, 6.60; %N, 17.20; Found: %C, 66.31; %H, 6.70; %N, 17.40.

EXAMPLE 167

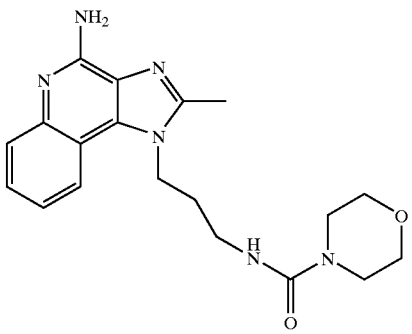

N-[3-(4-amino-2-methyl-1H-imidazo[4,5-c]quinolin-1-yl)propyl]morpholine-4-carboxamide Using the general method of Example 150 except that the reaction was run at 0° C, 1-(3-aminopropyl)-2-methyl-1H-imidazo[4,5-c]quinolin-4-amine (2.0 g, 7.8 mmol) was reacted with 4-morpholinecarbonyl chloride (1.17 g, 7.8 mmol) to provide 1.35 g of N-[3-(4-amino-2-methyl-1H-imidazo[4,5-c]quinolin-1-yl)propyl]morpholine-4-carboxamide as a white solid, m.p. 226.0–228.0° C. Analysis: Calculated for $C_{19}H_{24}N_6O_2$: %C, 61.94; %H, 6.57; %N, 22.81; Found: %C, 61.67; %H, 6.46; %N, 22.74.

Example 168

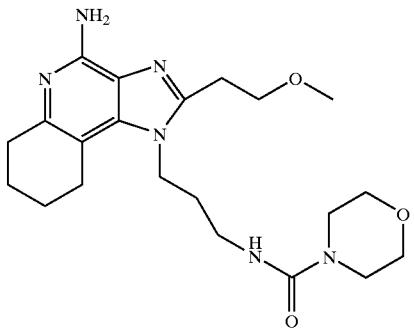

N-{3-[4-amino-2-(2-methoxyethyl)-6,7,8,9-tetrahydro-1H-imidazo[4,5-c]quinolin-1-yl]propyl}morpholine-4-carboxamide Using the general method of Example 167, 1-(3-aminopropyl)-2-(2-methoxyethyl)-6,7,8,9-tetrahydro-1H-imidazo[4,5-c]quinolin-4-amine (2.0 g, 6.59 mmol) was reacted with 4-morpholinecarbonyl chloride (1.08 g, 7.25 mmol) to provide 1.22 g of N-{3-[4-amino-2-(2-methoxyethyl)-6,7,8,9-tetrahydro-1H-imidazo[4,5-c]quinolin-1-yl]propyl}morpholine-4-carboxamide as a white powder, m.p. 171.8–173.2° C. Analysis: Calculated for $C_{21}H_{32}N_6O_3$: %C, 60.56; %H, 7.74; %N, 20.18; Found: %C, 60.30; %H, 7.72; %N, 20.1 1.

EXAMPLE 169

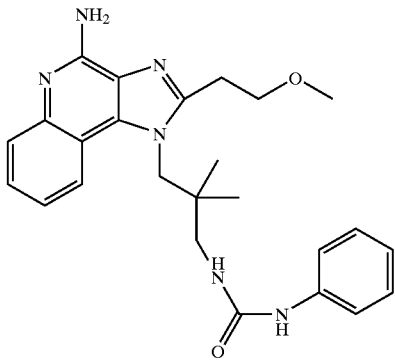

N-{3-[4-amino-2-(2-methoxyethyl)-1H-imidazo[4,5-c]quinolin-1-yl]-2,2-dimethylpropyl}-N'-phenylurea Using the general method of Example 145, 1-(3-amino-2,2-dimethylpropyl)-2-(2-methoxyethyl)-1H-imidazo[4,5-c]quinolin-4-amine (1.0 g, 3.05 mmol) was reacted with phenyl isocyanate to provide 0.45 g of N-(3-[4-amino-2-(2-methoxyethyl)-1H-imidazo[4,5-c]quinolin-1-yl]-2,2-dimethylpropyl)-N'-phenylurea as a white powder, m.p. 125.0–130.0° C. Analysis: Calculated for $C_{25}H_{30}N_6O_2 \cdot 0.40H_2O$: %C, 66.18; %H, 6.84; %N, 18.52; Found: %C, 66.05; %H, 6.61; %N, 18.64. %$H_2O$ calculated: 1.59; found: 1.53 (Karl Fisher);

$^1$H NMR (300 MHz, DMSO-$d_6$) δ 8.60 (s, 1H), 8.30 (d, J=8.3 Hz, 1H), 7.60 (dd, J=8.3, 1.0 Hz, 1H), 7.45–7.36 (m, 3H), 7.26–7.16 (m, 3H), 6.90.(m, 1H), 6.58 (s, 2H), 6.52 (m, 1H),4.81 (br s, 1H),4.40 (brs, 1H), 3.82 (m,2H), 3.39 (br s,2H),3.22 (m, 3H), 0.85 (br s, 6H);

$^{13}$C NMR (125 MHz, DMSO-$d_6$) δ 155.5, 152.1, 151.5, 144.6, 140.3, 133.4, 128.6, 126.3, 126.2, 121.0, 120.9, 120.4, 117.6, 115.3, 70.5, 58.0, 51.5, 47.5, 39.5, 27.8, 24.1, 22.6;

MS n/z 447 (M+H)

EXAMPLE 170

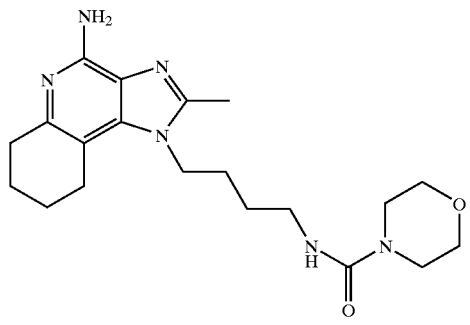

N-[4-(4-amino-2-methyl-6,7,8,9-tetrahydro-1H-imidazo[4,5-c]quinolin-1-yl)butyl]morpholine-4-carboxamide Using the general method of Example 143, 1-(4-aminobutyl)-2-methyl-6,7,8,9-tetrahydro-1H-imidazo[4,5-c]quinolin-4-amine (100 g, 3.7 mmol) was reacted with 4-morpholinecarbonyl chloride (0.43 mL, 3.7 mmol) to provide 1.14 g of N-[4-(4-amino-2-methyl-6,7,8,9-tetrahydro-1H-imidazo[4,5-c]quinolin-1-yl)butyl]morpholine-4-carboxamide as an off white solid, m.p. 133.6–134.6° C. Analysis: Calculated for $C_{20}H_{30}N_6O_2 \cdot 1.1H_2O$: %C, 59.12; %H, 7.99; %N, 20.68; Found: %C, 58.77; %H, 7.53; %N, 20.46.

EXAMPLE 171

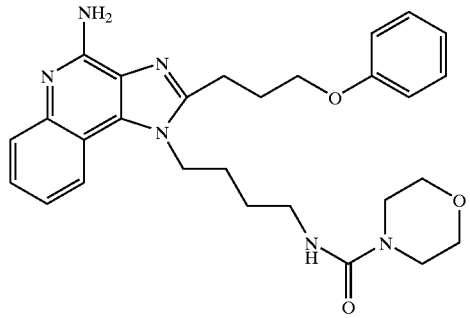

N-{4-[4-amino-2-(3-phenoxypropyl)-1H-imidazo[4,5-c]quinolin-1-yl]butyl}morpholine-4-carboxamide Using the general method of Example 143 except that pyridine was used in place of chloroform, 1-(4-aminobutyl)-2-(3-phenoxypropyl)-1H-imidazo[4,5-c]quinolin-4-amine (1.25 g, 3.2 mmol) was reacted with 4-morpholinecarbonyl chloride (0.41 mL, 3.5 mmol) to provide 0.50 g of N-(4-[4-amino-2-(3-phenoxypropyl)-1H-imidazo[4,5-c]quinolin-1-yl]butyl morpholine-4-carboxamide as a light brown solid, m.p. 71.5–72.1° C. Analysis: Calculated for $C_{28}H_{34}N_6O_3 \cdot 0.5H_2O$: %C, 65.73; %H, 6.90; %N, 16.43; Found; %C, 65.43; %H, 6.90; %N, 16.29.

EXAMPLE 172

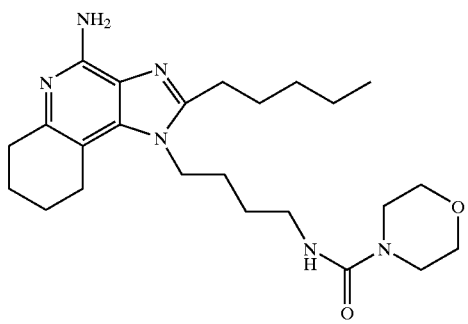

N-[4-(4-amino-2-pentyl-6,7,8,9-tetrahydro-1H-imidazo[4,5-c]quinolin-1-yl)butyl]morpholine-4-carboxamide hydrochloride Using the general method of Example 143, 1-(4-aminobutyl)-2-pentyl-6,7,8,9-tetrahydro-1H-imidazo[4,5-c]quinolin-4-amine (1.50 g, 4.6 mmol) was reacted with 4-morpholinecarbonyl chloride (0.53 mL, 4.6 mmol) to provide 1.6 g of the free base form of the named product. This material was combined with a minimum amount of methanol. The methanol was decanted off from an insoluble residue. The methanol solution was combined with 1N hydrochloric acid (5 mL) then diluted with diethyl ether (~15–20 ml,). The solution was concentrated under reduced pressure. The residue was triturated with diethyl ether, isolated by filtration and then taken up in methanol. The methanol solution was concentrated under reduced pressure. The residue was dried in a vacuum oven to provide 1.42 g of N-[4-(4-amino-2-pentyl-6,1,8,9-tetrahydro-1H-imidazo[4,5-c]quinolin-1-yl)butyl]morpholine-4-carboxamide hydrochloride as a light yellow crystalline solid, m.p. 126.8–127.5° C. Analysis: Calculated for $C_{24}H_{38}N_6O_2 \cdot HCl \cdot 1.25H_2O$: %C, %H, 8.34; %N, 16.75; Found: %C, 57.45; %H, 8.07; %N, 16.62.

EXAMPLE 173

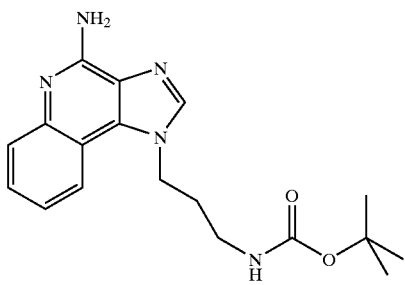

tert-butyl 3-(4-amino-1H-imidazo[4,5-c]quinolin-1-yl)propylcarbamate

Part A

3-Chloroperoxybenzoic acid (3.71 g of ~60%, 13.48 mmol) was added in small portions over a period of 20 minutes to a solution of tert-butyl 3-(1H-imidazo[4,5-c]quinolin-1-yl)propylcarbamate (4.0 g, 12.25 mmol) in chloroform (175 mL). After 1 hour the reaction was quenched with aqueous 1% sodium carbonate solution. The layers were separated. The organic layer was washed with aqueous 1% sodium carbonate solution (3×100 mL). The aqueous layer was extracted with chloroform (2×100 mL). The organic layers were combined and concentrated under reduced pressure to provide crude tert-butyl 3-(5-oxido-1H-imidazo[4,5-c]quinolin-1-yl)propylcarbamate.

Part B

Using the general method of Example 146 Part D, the material from Part A was aminated to provide crude product. A small portion (0.5 g) was purified by recrystallization from acetonitrile to provide 0.22 g of tert-butyl 3-(4amino-1H-imidazo[4,5-c]quinolin-1-yl)propylcarbamate as an off white powder, m.p. 196–198° C. Analysis: Calculated for $C_{18}H_{23}N_5O_2$: %C, 63.32; %H, 6.79; %N, 20.51; Found: %C, 63.05; %H, 6.81; %N, 20.58.

EXAMPLE 174

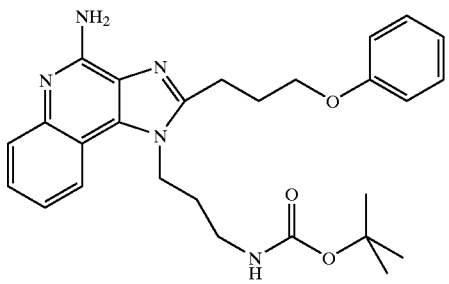

tert-butyl 3-[4-amino-2-(3-phenoxypropyl)-1H-imidazo[4,5-c]quinolin-1-yl]propylcarbamate

Part A

Using the general method of Example 173 Part A, tert-butyl 3-[2-(3-phenoxypropyl)-1H-imidazo[4,5-c]quinolin-1-yl]propylcarbamate was oxidized to provide tert-butyl 3-[5-oxido-2-(3-phenoxypropyl)-1H-imidazo[4,5-c]quinolin-1-yl]propylcarbamate.

Part B

Using the general method of Example 146 Part D, the material from Part A was aminated to provide crude product. A small portion was purified by column chromatography and then recrystallized from acetonitrile to provide 0.19 g of tert-butyl 3-[4-amino-2-(3-phenoxypropyl)-1H-imidazo[4,5-c]quinolin-1-yl]propylcarbamate as a tan powder, m.p. 151.0–153.0° C. Analysis: Calculated for $C_{27}H_{33}N_5O_3 \cdot 0.25H_2O$: %C, 67.55; %H, 7.03; %N, 14.59; Found: %C, 67.54; %H, 6.94; %N, 14.64.

EXAMPLE 175

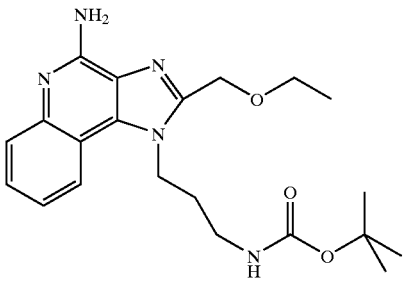

tert-butyl 3-[4-amino-2-(ethoxymethyl)-1H-imidazo[4,5-c]quinolin-1-yl]propylcarbamate

Part A

Using the general method of Example 173 Part A, tert-butyl 3-[2-(ethoxymethyl)-1H-imidazo[4,5-c]quinolin-1-yl]propylcarbamate was oxidized to provide tert-butyl 3-[2-(ethoxymethyl)-5-oxido-1H-imidazo[4,5-c]quinolin-1-yl]propylcarbamate.

Part B

Using the general method of Example 146 Part D, the material from Part A was aminated to provide crude product. A small portion (500 mg) was purified by column chromatography (silica gel eluting with a 1–10% methanol in chloroform gradient) to provide a solid. This material was recrystallized from acetonitrile to provide 150 mg of tert-butyl 3-[4-amino-2-(ethoxymethyl)-1H-imidazo[4,5-c]quinolin-1-yl]propylcarbamate as off white plates, m.p. 124.0–126.0° C. Analysis: Calculated for $C_{21}H_{29}N_5O_3$: %C, 63.14; %H, 7.32; %N, 17.53; Found: %C, 62.87; %H, 7.31; %N, 17.34.

EXAMPLE 176

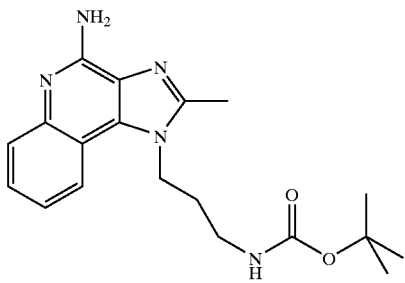

tert-butyl 3-(4-amino-2-methyl-1H-imidazo[4,5-c]quinolin-1-yl)propylcarbamate

Part A

Using the general method of Example 173 Part A, tert-butyl 3-(2-methyl-1H-imidazo[4,5-c]quinolin-1-yl)propylcarbamate (8.0 g, 23.50 mmol) was oxidized to provide tert-butyl 3-(2-methyl-5-oxido-1H-imidazo[4,5-c]quinolin-1-yl)propylcarbamate.

Part B

Using the general method of Example 146 Part D, the material from Part A was aminated to provide crude product. A small portion (0.5 g) was purified by recrystallization from isopropanol to provide 0.15 g of tert-butyl 3-(4amino-2-methyl-1H-imidazo[4,5-c]quinolin-1-yl)propylcarbamate as a white powder, m.p. 112–1 15° C. Analysis: Calculated for $C_{19}H_{25}N_5O_2$. 1.00 $C_3H_8O$: %C, 63.59; %H, 8.00; %N, 11.55; Found: %C, 63.33; %H, 7.95; %N, 16.70.

EXAMPLE 177

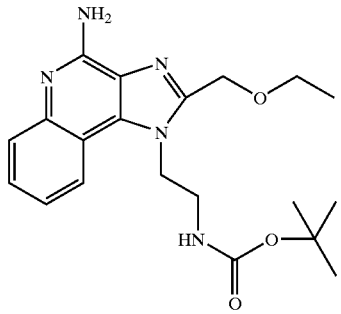

tert-butyl 2-[4-amino-2-(ethoxymethyl)-1H-imidazo[4,5-c]quinolin-1-yl]ethylcarbamate Part A Using the general method of Example 173 Part A, tert-butyl 2-[2-(ethoxymethyl)-1H-imidazo(4,5-c]quinolin-1-yl]ethylcarbamate (18.2 g, 49.1 mmol) was oxidized to provide 17.2 g of tert-butyl 2-[2-(ethoxymethyl)-5-oxido-1H-imidazo[4,5-c]quinolin-1-yl]ethylcarbamate as a solid.

Part B

Using the general method of Example 146 Part D, the material from Part A was aminated to provide ~18 g of crude product. A small portion was purified to provide 0.175 g of tert-butyl 2-[4-amino-2-(ethoxymethyl)-1H-imidazo[4,5-c]quinolin-1-yl]ethylcarbamate as a tan powder, m.p. 201.0–202.0° C.

MS (CI) m/e 386 (M+H).

EXAMPLE 178

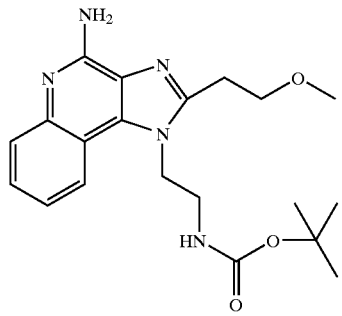

tert-butyl 2-[4-amino-2-(methoxymethyl)-1H-imidazo[4,5-c]quinolin-1-yl]ethylcarbamate Part A Using the general method of Example 173 Part A, tert-butyl 2-[2-(methoxyethyl)-1H-imidazo[4,5-c]quinolin-1-yl]ethylcarbamate (19.0 g, 51.2 mmol) was oxidized to provide 18.0 g of tert-butyl 2-[2-(methoxyethyl)-5-oxido-1H-imidazo[4,5-c]quinolin-1-yl]ethylcarbamate as a solid.

Part B

Using the general method of Example 146 Part D, the material from Part A was aminated to provide ~24 g of crude product. A small portion was purified to provide 0.218 g of tert-butyl 2-[4-amino-2-(methoxyethyl)-1H-imidazo[4,5-c]quinolin-1-yl]ethylcarbamate as a tan powder, m.p. 173.0–175.0° C.

MS (CI) m/e 386 (M+H).

Cytokine Induction in Human Cells

An in vitro human blood cell system was used to assess cytokine induction by compounds of the invention. Activity is based on the measurement of interferon and tumor necrosis factor ($\alpha$) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood is collected by venipuncture into EDTA vacutainer tubes from healthy human donors. Peripheral blood mononuclear cells (PBMCs) are separated from whole blood by density gradient centrifugation using Histopaque®-1077 (Sigma Chemicals, St. Louis, Mo.). The PBMCs are suspended at 3–4×$10^6$cells/mL in RPMI 1640 medium containing 10% fetal bovine serum, 2 mM L-glutamine and 1% penicillin/streptomycin solution (RPMI complete). The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells.

Incubation

The solution of test compound is added at 60 μM to the first well containing RPMI complete and serial (three fold or ten fold) dilutions are made. The PBMC suspension is then added to the wells in an equal volume, bringing the test compound concentrations to the desired range. The final concentration of PBMC suspension is 1.5–2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 5–10 minutes at 1000 rpm (~200× g) at 4° C. The cell culture supernatant is removed with a sterile polypropylene pipet and transferred to sterile polypropylene tubes. Samples are maintained at −30 to −70° C. until analysis. The samples are analyzed for interferon (a) and tumor necrosis factor (a) by ELISA

Interferon (a) and Tumor Necrosis Factor (a) Analysis by ELISA

Interferon (a) concentration is determined by ELISA using a Human Multi-Species kit from PBL Biomedical Laboratories, New Brunswick, N.J.

Tumor necrosis factor (a) (TNF)concentration is determined using ELISA kits available from Genzyme, Cambridge, Mass.; R&D Systems, Minneapolis, Minn.; or Pharmingen, San Diego, Calif.

The table below lists the lowest concentration found to induce interferon and the lowest concentration found to induce tumor necrosis factor for each compound. A "" indicates that no induction was seen at any of the tested concentrations (0.12, 0.37, 1.11, 3.33, 10 and 30 μM). A "*" indicates that no induction was seen at any of the tested concentrations (0.0001, 0.00 0161, 0.1, 1, and 10 μM).

Cytokine Induction in Human Cells

| Example Number | Lowest Effective Concentration (μM) | |
|---|---|---|
| | Interferon | Tumor Necrosis Factor |
| 2 | 0.37 | 3.33 |
| 16 | 1.11 | 10 |
| 2 | 0.37 | 3.33 |
| 4 | ** | ** |
| 17 | ** | 30 |
| 19 | 1.11 | 30 |
| 20 | 1.11 | 30 |
| 21 | ** | ** |
| 22 | ** | 10 |
| 23 | ** | 10 |
| 24 | ** | ** |
| 25 | 3.33 | ** |
| 26 | 10 | ** |
| 27 | ** | ** |
| 28 | 1.11 | 3.33 |
| 29 | ** | 10 |
| 30 | 3.33 | 30 |
| 31 | ** | 10 |
| 32 | 10 | 10 |
| 33 | ** | ** |
| 34 | ** | ** |
| 35 | 1.11 | 10 |
| 36 | 1.11 | 10 |
| 37 | 1.11 | 10 |
| 38 | ** | ** |
| 39 | 1.11 | 10 |
| 40 | 0.37 | 3.33 |
| 41 | 1.11 | 10 |
| 42 | ** | ** |
| 43 | ** | ** |
| 44 | 1.11 | 10 |
| 45 | 3.33 | ** |
| 46 | 1.11 | 3.33 |
| 1 | 3.33 | 30 |
| 47 | 3.33 | 10 |
| 48 | 0.37 | 3.33 |
| 49 | 3.33 | 3.33 |
| 50 | ** | ** |
| 51 | 30 | 30 |
| 52 | 1.11 | 10 |
| 6 | 0.37 | ** |
| 5 | 3.33 | ** |
| 67 | 1 | 10 |
| 69 | 0.1 | 1 |
| 68 | 1 | 1 |
| 137 | 1 | 10 |
| 132 | 0.01 | 1 |
| 133 | 0.1 | 10 |
| 53 | *** | 10 |
| 54 | *** | 10 |
| 55 | 1 | 1 |
| 56 | 1 | 1 |
| 139 | *** | *** |
| 140 | 10 | *** |
| 100 | 0.001 | 10 |
| 125 | 0.0001 | 10 |
| 126 | 0.0001 | 1 |
| 127 | 0.0001 | 1 |
| 120 | 0.0001 | 0.01 |
| 121 | 0.01 | 10 |
| 122 | 0.001 | 1 |
| 71 | 0.001 | 1 |
| 81 | 0.01 | 1 |
| 82 | 0.01 | 0.1 |
| 83 | 0.1 | 1 |
| 84 | 0.1 | 1 |
| 85 | 0.001 | 0.1 |
| 86 | 0.1 | 1 |
| 87 | 1 | *** |
| 88 | 0.1 | 1 |
| 89 | 0.1 | 10 |
| 101 | 0.01 | 1 |
| 102 | 0.001 | 1 |
| 103 | 0.0001 | 0.1 |
| 104 | 0.0001 | 1 |
| 105 | 0.001 | 1 |
| 106 | 0.0001 | 1 |
| 107 | 0.0001 | 1 |
| 108 | 0.0001 | 0.0001 |
| 109 | 0.0001 | 0.1 |
| 141 | *** | 10 |
| 110 | 0.001 | 1 |
| 111 | 0.001 | 1 |
| 112 | 0.0001 | 0.1 |
| 113 | 0.0001 | 1 |
| 114 | 0.0001 | 0.01 |
| 115 | 0.0001 | 1 |
| 116 | 0.0001 | 1 |
| 117 | 10 | 10 |
| 118 | 10 | 10 |
| 119 | 10 | 10 |
| 142 | 0.0001 | 0.1 |
| 134 | 0.001 | 1 |
| 135 | 0.01 | 10 |
| 136 | 0.0001 | 1 |
| 143 | 0.01 | 0.37 |
| 144 | 0.04 | 0.37 |
| 145 | 0.01 | 0.04 |

-continued

Cytokine Induction in Human Cells

| Example Number | Lowest Effective Concentration (μM) | |
|---|---|---|
| | Interferon | Tumor Necrosis Factor |
| 146 | 0.01 | 0.12 |
| 147 | 0.01 | 0.12 |
| 148 | 0.04 | 0.04 |
| 149 | 0.04 | 0.37 |
| 150 | 0.04 | 0.37 |
| 151 | 0.01 | 0.01 |
| 152 | 0.04 | 0.04 |
| 153 | 0.01 | 0.12 |
| 154 | 0.37 | 1.11 |
| 155 | 3.33 | 10 |
| 156 | 0.01 | 1.11 |
| 157 | 0.37 | 1.11 |
| 158 | 0.01 | 1.11 |
| 159 | 1.11 | 10 |
| 160 | 0.12 | 1.11 |
| 161 | 0.01 | 0.01 |
| 162 | 0.01 | 0.04 |
| 163 | 0.01 | 0.01 |
| 164 | 0.04 | 0.12 |
| 165 | 0.01 | 0.01 |
| 169 | 0.01 | 0.01 |
| 170 | 0.12 | 10 |
| 171 | ** | 10 |
| 172 | 0.01 | 0.37 |
| 173 | 1.11 | 10 |
| 174 | ** | ** |
| 175 | 0.04 | 0.37 |
| 176 | 0.12 | 1.11 |
| 177 | 0.04 | 0.37 |
| 178 | 0.12 | 1.11 |

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

What is claimed is:

1. A compound of the formula (I):

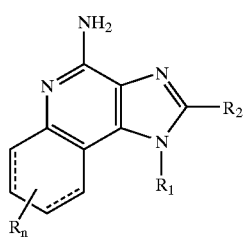

(I)

wherein bonds represented by the dashed lines are present or absent;

$R_1$ is —$C_{2-6}$ alkyl-$NR_3$—CY—$NR_5$—$R_4$ wherein Y is =O;

$R_4$ is alkyl or aryl;

$R_2$ is selected from the group consisting of:
—$C_{1-4}$ alkyl and
—$C_{1-4}$ alkyl-O—$C_{1-4}$ alkyl;

$R_3$ is hydrogen;

$R_5$ is hydrogen; and n is 0;

or a pharmaceutically acceptable salt thereof.

2. A compound or salt according to claim 1 wherein bonds represented by the dashed lines are present; and $R_4$ is phenyl, cyclohexyl, or isopropyl.

3. A compound or salt according to claim 2 wherein $R_4$ is cyclohexyl; and $R_2$ is $C_{1-4}$ alkyl-O—$C_{1-4}$ alkyl.

4. A compound or salt according to claim 2 wherein the compound is N-[4-(4-amino-2-propyl-1H-imidazo[4,5-c]quinolin-1-yl)butyl]-N'-phenylurea.

5. A compound or salt according to claim 1 wherein bonds represented by the dashed lines are present;

$R_1$ is -ethylene-$NR_3$CY$NR_5$—$R_4$; and $R_4$ is $C_{1-10}$ alkyl.

6. A compound or salt according to claim 5 wherein $R_4$ is isopropyl.

7. A compound or salt according to claim 5 wherein $R_2$ is ethoxymethyl.

8. A compound or salt according to claim 1 wherein bonds represented by dashed lines are absent;

$R_2$ is $C_{1-4}$ alkyl-O—$C_{1-4}$ alkyl—; and $R_4$ is $C_{1-10}$ alkyl.

9. A compound or salt according to claim 8 wherein $R_4$ is cyclohexyl.

10. A pharmaceutical composition comprising a therapeutically effective amount of a compound or salt of claim 1 in combination with a pharmaceutically acceptable carrier.

11. A method of inducing cytokine biosynthesis in an animal comprising administering a therapeutically effective amount of a compound or salt of claim 1 to the animal.

12. A method of treating a viral disease in an animal comprising administering an effective amount of a compound or salt of claim 1 to the animal.

13. A method of treating a neoplastic disease in an animal comprising administering an effective amount of a compound or salt of claim 1 to the animal.

* * * * *

UNITED STATES PATENT AND TRADEMARK OFFICE
CERTIFICATE OF CORRECTION

PATENT NO. : 6,784,188 B2
DATED : August 31, 2004
INVENTOR(S) : Crooks, Stephen L.

It is certified that error appears in the above-identified patent and that said Letters Patent is hereby corrected as shown below:

Column 1,
Line 31, delete "1J", insert in place thereof -- 1H --;
Line 40, delete "quinolin4amines", insert in place thereof -- quinolin-4-amines --;

Column 2,
Line 28, delete "Ia)", insert in place thereof -- (Ia) --;

Column 3,
Line 1, after "-heteroaryl" insert -- ; --;
Line 40, delete "R$_4$can", insert in place thereof -- R$_4$ can --;

Column 4,
Line 46, delete "-O-(alkyl)$_{01}$-", insert in place thereof -- -O-(alkyl)$_{0-1}$- --;

Column 5,
Line 52, delete "arc", insert in place thereof -- are --;
Line 55, delete "4chloro", insert in place thereof -- 4-chloro --;

Column 6,
Line 12, delete "R,", insert in place thereof -- R$_2$ --;
Line 58, delete "trichloroaectyl", insert in place thereof -- trichloroacetyl --;
Line 58, delete "isocyanante", insert in place thereof -- isocyanate --;
Line 65, delete "healing", insert in place thereof -- heating --;

Column 9,
Line 37, delete "R4", insert in place thereof -- R$_4$ --;

Column 10,
Line 23, after "above" insert -- . --;
Line 27, delete "quinolin4", insert in place thereof -- quinolin-4 --;

Column 11,
Line 4, after "above" insert -- . --;
Line 7, delete "quinolin4", insert in place thereof -- quinolin-4 --;
Line 52, delete "(I)", insert in place thereof -- (1) --;
Line 53, delete "imidizo", insert in place thereof -- imidazo --;

Column 12,
Line 48, delete "(I)", insert in place thereof -- (1) --;

UNITED STATES PATENT AND TRADEMARK OFFICE
CERTIFICATE OF CORRECTION

PATENT NO.    : 6,784,188 B2                                      Page 2 of 7
DATED         : August 31, 2004
INVENTOR(S)   : Crooks, Stephen L.

It is certified that error appears in the above-identified patent and that said Letters Patent is hereby corrected as shown below:

Column 14,
Line 1, after "and the like", insert new paragraph;
Line 6, delete "e.g.", insert in place thereof -- e.g., --;
Line 24, delete "nitrite", insert in place thereof -- nitrile --;

Column 15,
Line 59, delete "camii", insert in place thereof -- carnii --;
Line 64, delete "cosinophilia", insert in place thereof -- eosinophilia --;
Line 64, delete "thrombocythacmia", insert in place thereof -- thrombocythaemia --;

Column 17,
Line 26, delete "SN", insert in place thereof -- 5N --;
Line 30, delete "[4,5]", insert in place thereof -- [4,5-c] --;
Line 45, after "$C_{17}H_{21}N_5O_2$)" insert -- . --;
Line 65, delete "4chloro", insert in place thereof -- 4-chloro --;
Line 67, delete "4y1", insert in place thereof -- 4-yl --;

Column 18,
Line 13, after "product" insert -- . --;
Line 19, delete "4(1H", insert in place thereof -- 4-(1H --;
Line 21, delete "1-[[4", insert in place thereof -- 1-[4 --;
Line 37, delete "N-(2-(4amino", insert in place thereof -- N-[2-(4-amino --;

Column 19,
Line 9, after "solid" remove new paragraph. The next paragraph starting with "$^1$H NMR..." should all be in the first paragraph;
Line 14, after "J=7Hz,", delete "2 Hz,";
Line 15, delete "Ms", insert in place thereof -- MS --;
Line 31, delete "(4aminobutyl)", insert in place thereof -- (4-aminobutyl) --;
Line 44, delete "(t, J=7H, 2H)", insert in place thereof -- (t, J=7Hz, 2H) --;
Line 63, delete "$N^1$", insert in place thereof -- $N^4$ --;

Column 20,
Line 8, delete "butyl]morpholinecarboxamide", insert in place thereof -- butyl]-4-morpholinecarboxamide --;
Line 10, delete "δ 5 8.22 ", insert in place thereof -- δ 8.22 --;
Line 20, delete "1-y1]butyl", insert in place thereof -- 1-yl)butyl --;
Line 31, delete "phenylurca", insert in place thereof -- phenylurea --;
Line 40, delete "J=6.9H", insert in place thereof -- J=6.9Hz --;

UNITED STATES PATENT AND TRADEMARK OFFICE
CERTIFICATE OF CORRECTION

PATENT NO. : 6,784,188 B2
DATED : August 31, 2004
INVENTOR(S) : Crooks, Stephen L.

It is certified that error appears in the above-identified patent and that said Letters Patent is hereby corrected as shown below:

Column 20 (cont'd),
Line 46-60, delete 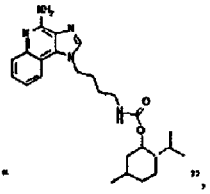 insert in place thereof 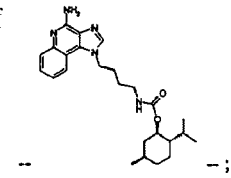

Line 61, delete "[sopropyl", insert in place thereof -- Isopropyl --;

Column 21,
Line 6, delete "5R)2-$^{\alpha}$", insert in place thereof -- 5R)-2- --;
Line 36, delete "[4,5c]", insert in place thereof -- [4,5-c] --;

Column 22,
Line 10, delete "m/c", insert in place thereof -- m/e --;
Line 10, delete "$C_{25}H_{13}N_5O_2$", insert in place thereof -- $C_{25}H_{23}N_5O_2$ --;
Line 42, delete "-N-(4-" insert in place thereof -- N-{4- --;
Line 43, after "butyl", insert -- } --;
Line 47, delete "2H 2H)", insert in place thereof -- 2H), 4.32(s, 2H), --;

Column 23,
Line 20, delete "$N^1$", insert in place thereof -- $N^4$ --;
Line 28, delete "N4", insert in place thereof -- $N^4$ --;
Line 31, delete "750", insert in place thereof -- 7.50 --;
Line 33, after "J=4.9 Hz" insert -- 4H --;
Line 58, delete "I)", insert in place thereof -- yl) --;
Line 66 delete "N-14", insert in place thereof -- N-{4 --;
Line 66, delete "aminoquinolin4", insert in place thereof -- aminoquinolin-4 --;
Line 66, delete "butyl)", insert in place thereof -- butyl} --;

Column 24,
Line 66, delete "%N.", insert in place thereof -- %N, --;

Column 25,
Line 44, delete "quinolin4", insert in place thereof -- quinolin-4 --;

Column 26,
Line 32, delete "tinder", insert in place thereof -- under --;
Line 65, delete "4fluorophenylisocyanate", insert in place thereof -- 4-fluorophenylisocyanate --;
Line 67, delete "($_4$-aminobutyl)2", insert in place thereof -- (4-aminobutyl)-2 --;

UNITED STATES PATENT AND TRADEMARK OFFICE
CERTIFICATE OF CORRECTION

PATENT NO. : 6,784,188 B2
DATED : August 31, 2004
INVENTOR(S) : Crooks, Stephen L.

It is certified that error appears in the above-identified patent and that said Letters Patent is hereby corrected as shown below:

Column 27,
Lines 1 and 22, delete "[4,5c]", insert in place thereof -- [4,5-c] --;

Column 28,
Line 6, delete "BioRad", insert in place thereof -- Bio-Rad --;
Lines 15-16, delete "trifluoroacctic", insert in place thereof -- trifluoroacetic --;

Column 46,
Line 48, delete "quinolin4", insert in place thereof -- quinolin-4 --;
Line 51, delete "al", insert in place thereof -- at --;

Column 66,
Line 40, delete "(4aminobutyl)", insert in place thereof -- (4-aminobutyl) --;

Column 79,
Line 1, delete "m5min", insert in place thereof -- mL/min --;

Column 80,
Line 5, delete "($^4$-aminobutyl)", insert in place thereof -- (4-aminobutyl) --;
Line 50, delete "(4Aminobutyl)", insert in place thereof -- (4-Aminobutyl) --;
Line 51, delete "quinolin4", insert in place thereof -- quinolin-4 --;

Column 83,
Line 66, after "days" insert -- . --;

Column 84,
Line 61, delete "quinolin4", insert in place thereof -- quinolin-4 --;
Line 63, after "4-aminobutyl", insert -- ) --;
Line 63, after "1H" delete "-amino", insert in place thereof -- -imidazo --;
Line 64, delete "-[4,5-c]"; insert in place thereof -- (4,5-c) --;

Column 86,
Line 1, delete "tetrahydro2", insert in place thereof -- tetrahydro-2 --;

Column 90,
Line 58, delete "20 L/min", insert in place thereof -- 20 mL/min --;

Column 91,
Line 25, delete "4amine", insert in place thereof -- 4-amine --;
Line 62, delete "0.59.mL", insert in place thereof -- 0.59 mL --;

UNITED STATES PATENT AND TRADEMARK OFFICE
CERTIFICATE OF CORRECTION

PATENT NO. : 6,784,188 B2
DATED : August 31, 2004
INVENTOR(S) : Crooks, Stephen L.

It is certified that error appears in the above-identified patent and that said Letters Patent is hereby corrected as shown below:

Column 92,
Line 5, delete "$C_{23}H_{26}N_6O..0.6$", insert in place thereof -- $C_{23}H_{26}N_6O\cdot 0.6$ --;

Column 93,
Lines 14, 20 and 24, remove indent;
Line 18, delete "J=6.4 Hz" , insert in place thereof -- J=6.8 Hz --;
Line 18, after "3.05" delete "(mn.2H)", insert in place thereof -- (m, 2H) --;
Line 19, after "1.29" delete "(";
Line 25, delete "m/z489(M+H)", insert in place thereof -- m/z 489 (M+H) --;

Column 94,
Line 37, delete "%C;", insert in place thereof -- %C, --;

Column 96,
Line 40, delete "185.5-186.40C", insert in place thereof -- 185.5-186.4°C --;
Line 65, delete "1.0 g.", insert in place thereof -- 1.0 g, --;

Column 97,
Line 65, delete ".1.19H$_2$O", insert in place thereof -- ·1.19 H$_2$O --;

Column 98,
Line 28, delete ")2-butyl", insert in place thereof -- )-2-butyl --;
Line 28, delete "4amine", insert in place thereof -- 4-amine --;
Lines 35, 40 and 44, remove indent;
Line 67, delete "4(2-hexyl", insert in place thereof -- 4-(2-hexyl --;

Column 99,
Lines 2, 6 and 7, delete "4(2-hexyl", insert in place thereof -- 4-(2-hexyl --;
Line 20, delete "]H-imidazo", insert in place thereof -- 1H-imidazo --;
Line 22, delete "$C27H_{34}N_6O$.", insert in place thereof -- $C_{27}H_{34}N_6O\cdot$ --;
Line 43, delete "4amine", insert in place thereof-- 4-amine --;
Line 45, after "2-methoxyethyl" insert -- ) --;
Line 46, delete "propyl)", insert in place thereof -- propyl} --;

Column 100,
Line 2, delete "N-(3", insert in place thereof -- N-{3 --;
Line 3, delete "propyl 1-]", insert in place thereof -- propyl}-N' --;
Line 30, delete "quinolin4", insert in place thereof -- quinolin-4 --;
Line 32, delete "N-13-[4amino", insert in place thereof -- N-{3-[4-amino --;
Line 33, delete "propyl)", insert in place thereof -- propyl} --;
Line 60, delete "(4aminobutyl)", insert in place thereof -- (4-aminobutyl) --;
Line 66, delete "7.4 1", insert in place thereof -- 7.41 --;

UNITED STATES PATENT AND TRADEMARK OFFICE
CERTIFICATE OF CORRECTION

PATENT NO. : 6,784,188 B2  Page 6 of 7
DATED : August 31, 2004
INVENTOR(S) : Crooks, Stephen L.

It is certified that error appears in the above-identified patent and that said Letters Patent is hereby corrected as shown below:

Column 102,
Line 1, delete "N-(3", insert in place thereof -- N-{3 --;
Lines 30 and 61, delete "quinolin4", insert in place thereof -- quinolin-4 --;
Line 31, delete "N- (3", insert in place thereof -- N-{3 --;
Line 32, delete "propyl)", insert in place thereof -- propyl} --;
Line 35, after "%H", insert -- , 7.58 --;
Line 53, delete "(2-methoxyethyl)", insert in place thereof -- (2-methoxyethyl) --;
Line 60, delete "1-imidazo", insert in place thereof -- 1H-imidazo --;

Column 103,
Line 55, delete "(2-methoxyethyl)1H", insert in place thereof -- (2-methoxyethyl)-1H --;
Line 57, delete "$^4$-Morpholinecarbonyl", insert in place thereof -- 4-Morpholinecarbonyl --;

Column 105,
Line 28, delete "20.1 1", insert in place thereof -- 20.11 --;
Line 51, delete "N-(3", insert in place thereof -- N-{3 --;
Line 53, delete "dimethylpropyl)", insert in place thereof dimethylpropyl} --;
Lines 58, 63 and 67, remove indent;
Line 60, after "6.90" delete ".";
Line 61, after "4.40", delete "(brs, 1H)", insert in place thereof -- (br s, 1H)--;
Line 67, delete "n/z", insert in place thereof -- m/z --;

Column 106,
Line 24, delete "100 g", insert in place thereof -- 1.00 g --;
Line 61, delete "N-(4", insert in place thereof -- N-{4 --;
Line 64, after "butyl" insert --}--;
Line 66, delete "Found;", insert in place thereof -- Found: --;

Column 107,
Line 28, delete "(~15-20 ml,)", insert in place thereof -- "(~15-20 mL) --;
Line 33, delete "6,1,8", insert in place thereof -- 6,7,8 --;
Line 37, after "%C", insert -- 57.47; --;

Column 108,
Line 5, delete "4amino", insert in place thereof -- 4-amino --;

Column 109,
Line 41, delete "4amino", insert in place thereof -- 4-amino --;
Line 43, delete "112-1 15 °C", insert in place thereof -- 112-115°C --;
Line 44, delete "C$_3$H$_8$0", insert in place thereof -- C$_3$H$_8$O --;
Line 66, delete "(4,5-c]", insert in place thereof -- [4,5-c] --;

UNITED STATES PATENT AND TRADEMARK OFFICE
CERTIFICATE OF CORRECTION

PATENT NO. : 6,784,188 B2
DATED : August 31, 2004
INVENTOR(S) : Crooks, Stephen L.

It is certified that error appears in the above-identified patent and that said Letters Patent is hereby corrected as shown below:

Column 110,
Line 10, remove indent;

Column 111,
Line 17, delete "at1000", insert in place thereof -- at 1000 --;
Line 21, after "interferon", delete "(a)" and insert in place thereof -- ($\alpha$) --;
Lines 21 and 28, after "factor", delete "(a)" and insert in place thereof -- ($\alpha$) --;
Lines 23 and 25, after "Interferon", delete "(a)" and insert in place thereof -- ($\alpha$) --;
Line 23, after "Factor", delete "(a)" and insert in place thereof -- ($\alpha$) --;
Line 38, delete "(0.0001, 0.00 0161, 0.1, 1, and 10 $\mu$M).", insert in place thereof
-- (0.0001, 0.001, 0.01, 0.1, 1 and 10 $\mu$M), --;

Column 114,
Line 10, after "hydrogen;" insert -- each R present is independently selected from the group consisting of $C_{1-10}$ alkyl, $C_{1-10}$ alkoxy, halogen and trifluoromethyl; --.

Signed and Sealed this

Seventh Day of December, 2004

JON W. DUDAS
*Director of the United States Patent and Trademark Office*